US007183290B2

(12) United States Patent
Haffner et al.

(10) Patent No.: US 7,183,290 B2
(45) Date of Patent: Feb. 27, 2007

(54) FLUOROPYRROLIDINES AS DIPEPTIDYL PEPTIDASE INHIBITORS

(75) Inventors: Curt Dale Haffner, Durham, NC (US); Darryl Lynn McDougald, Durham, NC (US); James Martin Lenhard, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 483 days.

(21) Appl. No.: 10/481,543

(22) PCT Filed: Jun. 26, 2002

(86) PCT No.: PCT/US02/20470

§ 371 (c)(1),
(2), (4) Date: Dec. 19, 2003

(87) PCT Pub. No.: WO03/002553

PCT Pub. Date: Jan. 9, 2003

(65) Prior Publication Data

US 2004/0242636 A1  Dec. 2, 2004

Related U.S. Application Data

(60) Provisional application No. 60/301,333, filed on Jun. 27, 2001, provisional application No. 60/384,041, filed on May 29, 2002.

(51) Int. Cl.
C07D 401/12 (2006.01)
C07D 401/14 (2006.01)
C07D 403/12 (2006.01)
C07D 413/14 (2006.01)
C07D 451/04 (2006.01)
C07D 207/16 (2006.01)
C07D 207/26 (2006.01)
C07D 207/48 (2006.01)
A61K 31/40 (2006.01)
A61K 31/4025 (2006.01)
A61P 3/10 (2006.01)

(52) U.S. Cl. .................. 514/304; 514/321; 514/326; 514/343; 514/422; 514/423; 546/125; 546/198; 546/208; 546/279.1; 548/518; 548/530; 548/540

(58) Field of Classification Search .............. 546/125, 546/198, 208, 279.1; 548/518, 530, 540; 514/304, 321, 326, 343, 422, 423
See application file for complete search history.

(56) References Cited

U.S. PATENT DOCUMENTS 6,011,155 A    1/2000   Villhauer
6,090,786 A    7/2000   Augustyns et al.
6,124,305 A    9/2000   Villhauer
6,166,063 A   12/2000   Villhauer
2002/0019411 A1  2/2002   Robl et al.
2005/0130981 A1*  6/2005   Aranyl et al. .......... 514/252.03
2005/0176771 A1*  8/2005   Hayakawa et al. ......... 514/326

FOREIGN PATENT DOCUMENTS

| EP | 1 245 568 | 3/2002 |
| EP | 1 333 025 | 8/2003 |
| WO | 98/19998 | 5/1998 |
| WO | 99/38501 | 8/1999 |
| WO | 99/61431 | 12/1999 |
| WO | 00/34241 | 6/2000 |
| WO | 00/56296 | 9/2000 |
| WO | 01/14318 | 3/2001 |
| WO | 01/34594 | 5/2001 |
| WO | 01/40180 | 6/2001 |
| WO | 01/52825 | 7/2001 |
| WO | 01/62266 | 8/2001 |
| WO | 01/81304 | 11/2001 |
| WO | 01/81337 | 11/2001 |
| WO | 01/96295 | 12/2001 |
| WO | 02/02560 | 1/2002 |
| WO | 02/30890 | 4/2002 |
| WO | 02/30891 | 4/2002 |
| WO | 02/38541 | 5/2002 |
| WO | 02/076450 | 10/2002 |
| WO | 02/83128 | 10/2002 |
| WO | 03/000180 | 1/2003 |
| WO | 03/000250 | 1/2003 |
| WO | 03/35067 | 5/2003 |

OTHER PUBLICATIONS

Jiang et al., Res. Virol., 148, 255-266, 1977.*
Sedo et al., Biochimica et Biophysica Acta, 1550, 107-116, 2001.*
Tanaka et al., Int. J. Immunopharmac., 19(1), 15-24, 1997.*
Zhang et al., Current Opinion in Chemical Biology, 4, 461-467, 2000.*
Augustyns, K.J.L. et al., "Pyrrolidides: Synthesis and Structure-activity Relationships as Inhibitors of Dipeptidyl Peptidase IV," *European Journal of Medicinal Chemistry*, 1997, vol. 32, No. 4, pp. 301-309.

* cited by examiner

Primary Examiner—Fiona T. Powers
(74) Attorney, Agent, or Firm—Amy H. Fix

(57) ABSTRACT

The present invention relates to novel compounds, their use for inhibiting post prolin/analine-cleaving proteases, such as serine proteases, such as dipeptidyl peptidases, such as dipeptidyl peptidase IV (DPP-IV), and to methods for their production and their therapeutic utility.

38 Claims, No Drawings

FLUOROPYRROLIDINES AS DIPEPTIDYL PEPTIDASE INHIBITORS

This This application is filed pursuant to 35 U.S.C. § 371 as a United States National Phase Application of International Application No. PCT/US02/20470 filed Jun. 26, 2002, which claims priority from U.S. 60/301,333 filed Jun. 27, 2001 and U.S. 60/384,041 filed May 29, 2002.

FIELD OF INVENTION

The present invention relates to compounds inhibiting dipeptidyl peptidases, such as II (DPP-II) and IV (DPP-IV), to methods for their production, and to their therapeutic utility.

BACKGROUND OF THE INVENTION

Dipeptidyl peptidase IV (DPP-IV) is a post-proline/alanine cleaving serine protease found in various tissues of the body including kidney, liver, and intestine. DPP-IV is thought to regulate the activity of multiple physiologically important peptides, including, but not limited to, GLP1, GIP, GLP2, GRP, vasoactive intestinal peptide, peptide histidine methionine, PYY, substance P, beta-casomorphine, NPY, PACAP38, prolactin, chorionic gonadotropin, aprotinin, corticotropin-like intermediate lobe peptide, pituitary adenylyl cyclase-activating peptide, (Tyr)melanostatin, LD78beta(3-70), RANTES, eotaxin procolipase, enterostatin, vasostatin 1, endomorphin, morphiceptin, stromal cell derived factor, macrophage-derived chemokine, granulocyte chemotactic protein-2, and GHRH/GRF. As examples of the therapeutic value of DPP-IV, DPP-IV is believed to be involved in a variety of metabolic, gastrointestinal, viral, and inflammatory diseases, including, but not limited to, diabetes, obesity, hyperlipidemia, dermatological or mucous membrane disorders, psoriasis, intestinal distress, constipation, autoimmune disorders such as encephalomyelitis, complement mediated disorders such as glomerulonepritis, lipodystrophy, and tissue damage, psychosomatic, depressive, and neuropsychiatric disease such as anxiety, depression, insomnia, schizophrenia, epilepsy, spasm, and chronic pain, HIV infection, allergies, inflammation, arthritis, transplant rejection, high blood pressure, congestive heart failure, tumors, and stress-induced abortions, for example cytokine-mediated murine abortions. For example, DPP-IV, also known as CD26, mediates T-cell activation and HIV infection (Ohtsuki et al., 2000). T-cells expressing DPP-IV/CD26 are preferentially infected and depleted in HIV-infected individuals (Ohtsuki et al., 2000). DPP-IV inhibitors have demonstrated anti-inflammatory effects in animal models of arthritis (Tanaka et al, 1997). Additionally, DPP-IV inhibition has been shown to prolong cardiac transplant survival (Korom et al., 1997). In vitro studies suggest that DPP-IV/CD26 expression correlate with tumor progression of malignant melanomas of the skin (Van den Oord, 1998). Furthermore, DPP-IV is thought to regulate metabolism by cleaving the penultimate proline/alanine at the amino-terminus of polypeptides (Mentlein, 1999), such as glucagon-like peptides (GLP) and neuropeptide Y (NPY).

More specifically, GLPs help metabolize glucose and, thus, regulation of GLPs likely should be beneficial in the treatment of metabolic disorders such as diabetes. Diabetes, for example type 2 (also called noninsulin-dependent diabetes mellitus (NIDDM) or maturity-onset) diabetes, results in elevated blood sugar levels due to absolute or relative insufficiencies of insulin. Type 2 diabetes is the more common form of diabetes, accounting for 90% of cases, or about 16 million Americans. Most type 2 diabetics produce variable, sometimes normal, amounts of insulin, but they have abnormalities in liver and muscle cells that resist its actions. Insulin attaches to the receptors of cells, but glucose does not get inside, a condition known as insulin resistance. Many type 2 diabetics seem to be incapable of secreting enough insulin to overcome insulin resistance. GLP-1 enhances insulin secretion. Thus, regulation of GLP-1 correlates to a regulation of insulin secretion. Moreover, GLP-1 decreases hepatic glucose production, gastric emptying, and food intake (Deacon et al., 1995). Further, GLP-2 maintains the integrity of the intestinal mucosal epithelium via effects on gastric motility, nutrient absorption, crypt cell proliferation and apoptosis, and intestinal permeability (Drucker, 2001).

DPP-IV inhibitors preserve GLP-1 function for a longer time (Balka, 1999). Thus, DPP-IV inhibitors may promote satiety, weight loss, and the antidiabetic effects of GLP-1 (Deacon et al., 1995; Holst and Deacon, 1998). For example, inhibition of DPP-IV with the known compound NVP-DPP728 increases plasma GLP-1 (2-36 amide) concentrations and improves oral glucose tolerance in obese Zucker rats. See, Diabetologia 42: 1324–1331. Both subcutaneously and intravenously administered GLP-1 is rapidly degraded from the $NH_2$-terminus in type II diabetic patients and in healthy subjects. See, Diabetes 44:1126, 1995.

Moreover, DPP-IV inhibitors preserve GLP-2 for longer periods of time and, thus, may be useful for treating intestinal insufficiencies and mucous membrane disorders (Hartmann B et al., 2000).

While DPP-IV is the predominate protease regulating GLP turnover, similar substrate or inhibitor specificity may be observed for related proteases. Related serine proteases include, but are not limited to, dipeptidyl peptidase-II (DPP-II), dipeptidyl peptidase IV beta, dipeptidyl peptidase 8, dipeptidyl peptidase 9, aminopeptidase P, fibroblast activating protein alpha (seprase), prolyl tripeptidyl peptidase, prolyl oligopeptidase (endoproteinase Pro-C), attractin (soluble dipeptidyl-aminopeptidase), acylaminoacyl-peptidase (N-acylpeptide hydrolase; fMet aminopeptidase) and lysosomal Pro-X carboxypeptidase (angiotensinase C, prolyl carboxypeptidase). Proline-cleaving metallopeptidases that may share similar substrate or inhibitor specificity to DPP-IV include membrane Pro-X carboxypeptidase (carboxypeptidase P), angiotensin-converting enzyme [Peptidyl-dipeptidase A multipeptidase], collagenase 1 (interstitial collagenase; matrix metalloproteinase 1; MMP-1; Mcol-A), ADAM 10 (alpha-secretase, myelin-associated disintegrin metalloproteinase), neprilysin (atriopeptidase; CALLA; CD10; endopeptidase 24.11; enkephalinase), Macrophage elastase [metalloelastase; matrix metalloproteinase 12; MMP-12], Matrilysin (matrix metalloproteinase 7; MMP-7), and neurolysin (endopeptidase 24.16; microsomal endopeptidase; mitochondrial oligopeptidase).

Furthermore, beyond mammalian serine peptidases and proline-cleaving metallopeptidases, other non-mammalian proteases may share similar substrate or inhibitor specificity to DPP-IV. Non-limiting examples of such non-mammalian serine proteases include prolyl aminopeptidase (prolyl iminopeptidase), IgA1-specific serine type prolyl endopeptidase (IgA protease, *Neisseria, Haemophilus*), dipeptidyl aminopeptidase A (STE13) (*Saccharomyces cerevisiae*), dipeptidyl aminopeptidase B (fungus), prolyl oligopeptidase homologue (*Pyrococcus* sp.), oligopeptidase B (*Escherichia coli* alkaline proteinase II; protease II), dipeptidyl aminopeptidase B1 (*Pseudomonas* sp.), dipeptidyl-peptidase IV (bacteria), dipeptidyl aminopeptidase (*Aureobacterium*), dipeptidyl-peptidase IV (insect), dipeptidyl-peptidase V, allergen Tri t4 (*Trichophyton tonsurans*), secreted alanyl DPP (*Aspergillus oryzae*), peptidase II-mes (*Prosopis velutina*), and bamboo serine proteinase (*Pleloblastus hindsii*).

Non-limiting examples of such non-mammalian proline-cleaving metallopeptidases include penicillolysin (fungal acid metalloendopeptidase), proline-specific peptidyl-dipeptidase (*Streptomyces*), coccolysin (gelatinase, *Enterococcus faecalis*), aminopeptidase Ey, (hen egg yolk) (apdE g.p.; *Gallus gallus domesticus*), gametolysin (*Chlamydomonas* cell wall degrading protease), and snake venom proline-cleaving metalloproteases as well. for further reference.

Dipeptidyl peptidase II (DPP II) is a serine protease localized to lysosomes in cells and believed to be involved in lysosomal degradation and protein turnover. The order of expression of DPP-II is kidney>>testis>or=heart>brain>or=lung>spleen>skeletal muscle>or=liver (Araki H et al., J Biochem (Tokyo) 2001, 129:279–88). This expression suggests possible utility in kidney or lysosomal-related disorders. Substrate specificity studies indicated that purified DPP-II hydrolyzes specifically alanine or proline residues at acidic pH (4.5–5.5). DPP-II has significant sequence homology and substrate specificity to quiescent cell proline dipeptidase and prolyl carboxypeptidase, suggesting possible overlapping functions between these proteases (Araki H et al., J Biochem (Tokyo) 2001, 129:279–88).

The present invention includes novel DPP-II and/or DPP-IV inhibitors, as well as methods of their therapeutic use and methods of their production. While not being limited thereby, the compounds of the present invention are believed useful for the treatment of a variety of metabolic, gastrointestinal, viral, and inflammatory diseases, including, but not limited to, diabetes, obesity, hyperlipidemia, dermatological or mucous membrane disorders, psoriasis, intestinal distress, constipation, autoimmune disorders such as encephalomyelitis, complement mediated disorders such as glomerulonepritis, lipodystrophy, and tissue damage, psychosomatic, depressive, and neuropsychiatric disease such as anxiety, depression, insomnia, schizophrenia, epilepsy, spasm, and chronic pain, HIV infection, allergies, inflammation, arthritis, transplant rejection, high blood pressure, congestive heart failure, tumors, and stress-induced abortions, for example cytokine-mediated murine abortions.

SUMMARY OF THE INVENTION

The present invention includes novel inhibitors of post proline/analine cleaving proteases, including serine proteases, including dipeptidyl peptidases, including DPP-II and DPP-IV. These compounds exhibit surprising characterisitcs including improved potency, extended duration of action, improved stability, and/or a decrease in toxicity.

One embodiment of the present invention includes compounds of formula (I):

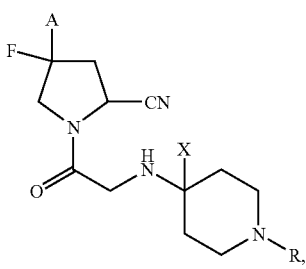

(I)

wherein X is H or alkyl and R is selected from isopropylsulfonyl, benzylsulfonyl, naphthylethylsulfonyl, mesitylsulfonyl, optionally substituted cycloalkylsulfonyl, benzoxazolyl, optionally substituted aryl. Preferably X is H, Preferably when X is alkyl, X is $C_1$–$C_6$ alkyl, more preferably methyl. Preferably the aryl is substituted one or more times with cyano, halogen, nitro, or haloalkyl. Preferably the aryl is phenyl or benzyl. Preferably the cycloalkylsulfonyl is substituted one or more times with oxo or alkyl. More preferably the cycloalkylsulfonyl is dimethyl-oxo-bicyclo [2.2.1]-heptyl methyl sulfonyl.

Another embodiment of the present invention includes compounds of formula (II):

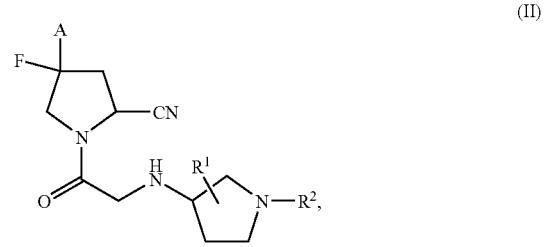

(II)

wherein $R^1$ is H or Oxo, and $R^2$ is alkylsulfonyl, optionally substituted aryl, optionally substituted heteroaryl. In one aspect of this embodiment preferably $R^1$ is oxo. Preferably $R^2$ is aryl, preferably phenyl, and more preferably is substituted one or more times with halogen. In another aspect of this embodiment preferably $R^1$ is H. Preferably $R^2$ is alkylsulfonyl or optionally substituted heteroaryl. Preferably the alkylsulfonyl is $C_1$–$C_6$ alkylsulfonyl, more preferably isopropylsulfonyl. Preferably the optionally substituted heteroaryl is optionally substituted pyridyl, more preferably, substituted one or more times with cyano.

Another embodiment of the present invention includes compounds of formula (III):

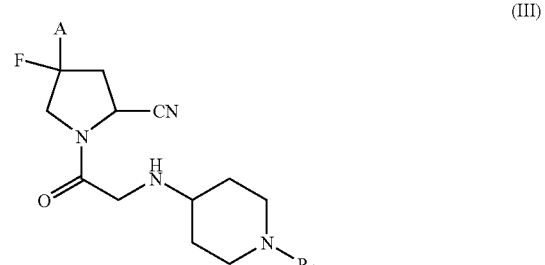

(III)

wherein $R^4$ is selected from optionally substituted aryl or alkyl. Preferably the alkyl is $C_1$–$C_6$ alkyl, more preferably t-butyl. Preferably the aryl is substituted one or more times with halogen or haloalkyl. Preferablly the aryl is phenyl.

Another embodiment of the present invention includes compounds of formula (IV):

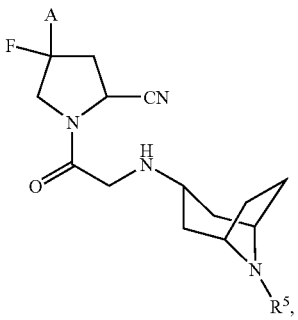

wherein R⁵ is alkoxycarbonyl. Preferably R⁵ is $C_1$–$C_6$ alkoxycarbonyl, more preferably R⁵ is ethyloxycarbonyl.

Another embodiment of the present invention includes compounds of formula (V):

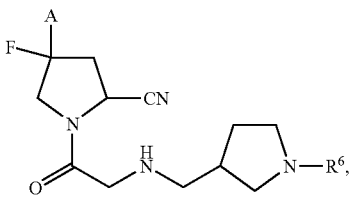

wherein R⁶ is alkylsulfonyl or optionally substituted aryl. Preferably the alkylsulfonyl is $C_1$–$C_6$ alkylsulfonyl, more preferably, isopropylsulfonyl. Preferably the aryl is substituted one or more times with halogen or cyano. Preferably the aryl is phenyl.

Another embodiment of the present invention includes compounds of formula (VI):

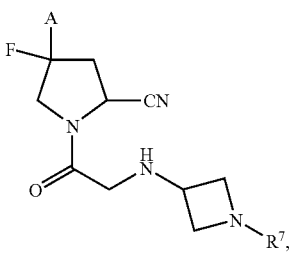

wherein R⁷ is alkylsulfonyl. Preferably R⁷ is $C_1$–$C_6$ alkylsulfonyl, more preferably R⁷ is isopropylsulfonyl.

Particularly preferred compounds of the present invention include:

(2S,4S)-4-Fluoro-1-({[1-(isopropylsulfonyl)-4-piperdinyl]amino}acetyl)-2-pyrrolidinecarbonitrile hydrochloride;

(2S)-4,4-Difluoro-1-({[1-(isopropylsulfonyl)-4-piperidinyl]amino}acetyl)-2-pyrrolidnecarbonitrile;

(2S,4S)-4-Fluoro-1-({[(3S)-1-(4-fluorophenyl)-2-oxopyrrolidinyl]amino}acetyl)-2-pyrrolidinecarbonitrile hydrochloride;

(2S,4S)-4Fluoro-1-({[(3S)-1-(4-fluorobenzyl)-2-oxopyrrolidinyl]amino}acetyl)-2-pyrrolidinecarbonitrile hydrochloride;

(2S,4S)-1-{[(1-Benzylpiperidin-4-yl)amino]acetyl}-4-fluoropyrrolidine-2-carbonitrile hydrochloride;

(2S,4S)-4-Fluoro-1-({[1-(4-fluorophenyl)piperidin-4-yl]amino}acetyl)pyrrolidine-2-carbonitrile hydrochloride;

(2S,4S)-1-({[1-(4-Cyanophenyl)piperidin-4-yl]amino}acetyl)-4-fluoropyrrolidine-2-carbonitrile hydrochloride;

(2S,4S)-1-({[1-(4-Cyano-3-fluorophenyl)piperidin-4-yl]amino}acetyl)-4-fluoropyrrolidine-2-carbonitrile hydrochloride;

(2S,4S)-1-({[1-(4-Cyano-3,5-difluorophenyl)piperidin-4-yl]amino}acetyl)-4-fluoropyrrolidine-2-carbonitrile hydrochloride;

(2S,4S)-1-({[1-(3-Cyano-5-fluorophenyl)piperidin-4-yl]amino}acetyl)-4-fluoropyrrolibine-2-carbonitrile hydrochloride;

(2S,4S)-1-({[1-(3,5-Difluorophenyl)piperidin-4-yl]amino}acetyl)-4-fluoropyrrolidine-2-carbonitrile hydrochloride;

(2S,4S)-4-Fluoro-1-{[(4-phenylcyclohexyl)amino]acetyl}pyrrolidine-2-carbonitrile hydrochloride;

Ethyl 3-({2-[(2S,4S)-2-cyano-4-fluoropyrrolidin-1-yl]-2-oxoethyl}amino)-8-azabicyclo[3.2.1]octane-8-carboxylate hydrochloride;

(2S,4S)-4-Fluoro-1-({[4-(4-fluorophenyl)cyclohexyl]amino}acetyl)pyrrolidine-2-carbonitrile hydrochloride;

(2S,4S)-4-Fluoro-1-[({4-[4-(trifluoromethyl)phenyl]cyclohexyl}amino)acetyl]pyrrolidine-2-carbonitrile hydrochloride;

(2S,4S)-4-Fluoro-1-{[(4-pyridin-2-ylcyclohexyl)amino]acetyl}pyrrolidine-2-carbonitrile hydrochloride (cis et trans);

(2S,4S)-1-{[(4-Tert-butylcyclohexyl)amino]acetyl}-4-fluoropyrrolidine-2-carbonitrile hydrochloride;

(2S,4S)-4-Fluoro-1-[({[(3R)-1-(isopropylsulfonyl)pyrrolidinyl]methyl }amino)acetyl]-2-pyrrolidinecarbonitrile and hydrochloride;

(2S,4S)-4-Fluoro-1-[({[(3S)-1-(isopropylsulfonyl)pyrrolidinyl]methyl}amino)acetyl]-2-pyrrolidinecarbonitrile and hydrochloride;

(2S,4S)-1-[({[(3R)-1-(3-Cyano-5-fluorophenyl)pyrrolidinyl]methyl}amino)acetyl]-4-fluoro-2-pyrrolidinecarbonitrile hydrochloride;

(2S,4S)-4-Fluoro-1-({[1-(4-nitrophenyl)piperidin-4-yl]amino}acetyl)pyrrolidine-2-carbonitrile;

(2S,4S)-4-Fluoro-1-[({1-[4-(trifluoromethyl)phenyl]piperidin-4-yl}amino)acetyl]pyrrolidine-2-carbonitrile hydrochloride;

(2S,4S)-1-({[1-(1,3-Benzoxazol-2-yl)piperidin-4-yl]amino}acetyl)-4-fluoropyrrolidine-2-carbonitrile hydrochloride;

(2S,4S)-1-({[1-({[(1R,4R)-7,7-dimethyl-2-oxobicyclo[2.2.1]hept-1-yl]methyl}sulfonyl) piperidin-4-yl]amino}acetyl)-4-fluoropyrrolidine-2-carbonitrile hydrochloride;

(2S,4S)-1-({[1-(Benzylsulfonyl)piperidin-4-yl]amino}acetyl)-4-fluoropyrrolidine-2-carbonitrile hydrochloride;

(2S,4S)-4-Fluoro-1-{[(1-{[2-(1-naphthyl)ethyl]sulfonyl}piperidin-4-yl)amino]acetyl}pyrrolidine-2-carbonitrile hydrochloride;

(2S,4S)-4-Fluoro-1-({[1-(mesitylsulfonyl)piperidin-4yl]amino}acetyl)pyrrolidine-2-carbonitrile hydrochloride;

(2S,4S)-4-Fluoro-1-({[(3R)-1-(isopropylsulfonyl)pyrrolidinyl]amino}acetyl)-2-pyrrolidinecarbonitrile hydrochloride;

(2S,4S)-4-Fluoro-1-({[(3S)-1-(isopropylsulfonyl)pyrrolidinyl]amino}acetyl)-2-pyrrolidinecarbonitrile hydrochloride;

6-[(3S)-3-({2-[(2S,4S)-2-Cyano-4-fluoropyrrolidin-1-yl]-2-oxoethyl}amino)pyrrolidin-1-yl]nicotinonitrile bis(trifluoroacetate); and (2S,4S)-4-Fluoro-1-({[1-(isopropylsulfonyl)azetidin-3-yl]amino}acetyl)pyrrolidine-2-carbonitrile trifluoroacetate.

Preferably, for each embodiment of the present invention A is H and is located trans to the depicted nitrile warhead.

Another aspect of the present invention includes pharmaceutical formulations comprising a compound of the present invention. Preferably such a pharmaceutical formulation further includes a pharmaceutically acceptable carrier.

Another aspect of the present invention includes a method of inhibiting a post-proline/analine-cleaving protease comprising administering a compound of the present invention. Preferably the post-proline/analine-cleaving protease is a serine protease. More preferably the serine protease is a dipeptidyl peptidase. More preferably the dipeptidyl peptidase is DPP-II or DPP-IV.

Another aspect of the present invention includes a method for the treatment or prophylaxis of metabolic disorders, gastrointestinal disorders, viral disorders, inflammatory disorders, diabetes, obesity, hyperlipidemia, dermatological or mucous membrane disorders, psoriasis, intestinal distress, constipation, autoimmune disorders, encephalomyelitis, complement mediated disorders, glomerulonepritis, lipodystrophy, tissue damage, psychosomatic, depressive, and neuropsychiatric disorders, HIV infection, allergies, inflammation, arthritis, transplant rejection, high blood pressure, congestive heart failure, tumors, and stress-induced abortions comprising administering an effective amount of a compound of the present invention. Preferably the method includes a therapeutically effective amount of a compound of the present invention administered for the treatment or prophylaxis of diabetes.

Another aspect of the present invention includes use of a compound of the present invention in the manufacture of a medicament for the inhibition of a post proline/analine-cleaving protease. Preferably the post proline/analine-cleaving protease is a serine protease. Preferably the serine protease is a dipeptidyl peptidase. Preferably the dipeptidyl peptidase is DPP-II or DPP-IV.

Another aspect of the present invention includes the use of a compound of the present invention in the manufacture of a medicament for the treatment or prophylaxis of metabolic disorders, gastrointestinal disorders, viral disorders, inflammatory disorders, diabetes, obesity, hyperlipidemia, dermatological or mucous membrane disorders, psoriasis, intestinal distress, constipation, autoimmune disorders, encephalomyelitis, complement mediated disorders, glomerulonepritis, lipodystrophy, tissue damage, psychosomatic, depressive, and neuropsychiatric disorders, HIV infection, allergies, inflammation, arthritis, transplant rejection, high blood pressure, congestive heart failure, tumors, and stress-induced abortions.

Another aspect of the present invention includes a compound of the present invention for use as an active therapeutic substance.

Another aspect of the present invention includes a compound of the present invention for use in the manufacture of a medicament for the inhibition of serine protease. Accordingly, another aspect of the present invention includes a compound of the present invention for use in the manufacture of a medicament for the treatment or prophylaxis of metabolic disorders, gastrointestinal disorders, viral disorders, inflammatory disorders, diabetes, obesity, hyperlipidemia, dermatological or mucous membrane disorders, psoriasis, intestinal distress, constipation, autoimmune disorders, encephalomyelitis, complement mediated disorders, glomerulonepritis, lipodystrophy; tissue damage, psychosomatic, depressive, and neuropsychiatric disorders, HIV infection, allergies, inflammation, arthritis, transplant rejection, high blood pressure, congestive heart failure, tumors, and stress-induced abortions.

DETAILED DESCRIPTION OF THE PREFERRED EMBODIMENT

The term "alkyl" refers to a straight or branched chain saturated aliphatic hydrocarbon that may be optionally substituted, with multiple degrees of substitution being allowed. Examples of "alkyl" include, but are not limited to methyl, ethyl, n-propyl, isopropyl, n-butyl, t-butyl, n-pentyl, isobutyl, and the like.

As used throughout this specification, the preferred number of carbon atoms will be represented by, for example, the phrase "$C_x$–$C_y$ alkyl" which refers to an alkyl group, as herein defined, containing the specified number of carbon atoms. Similar terminology will apply for other preferred ranges as well.

The term "alkylene" refers to a divalent straight or branched chain aliphatic hydrocarbon radical that may be optionally substituted, with multiple degrees of substitution being allowed. An example of "alkylene" includes, without limitation, methylene, namely —$CH_2$—.

The term "alkenyl" refers to a straight or branched chain aliphatic hydrocarbon, containing one or more carbon-to-carbon double bonds that may be optionally substituted, with multiple degrees of substitution being allowed. Examples include, but are not limited to, vinyl and the like.

As used herein the term "alkenylene" refers to a divalent straight or branched chain aliphatic hydrocarbon radical, containing one or more carbon-to-carbon double bonds, which may be optionally substituted, with multiple degrees of substitution being allowed. An example of "alkenylene" includes, without limitation, vinylene, namely, —CH=CH—.

As used herein the term "alkynyl" refers to a straight or branched aliphatic hydrocarbon containing one or more triple bond, which may optionally be substituted, with multiple degrees of substitution being allowed. Examples of "alkynyl" as used herein include, but are not limited to, ethynyl and the like.

As used herein the term "alkynylene" refers to a divalent straight or branched chain aliphatic hydrocarbon radical, containing at least one carbon-to-carbon triple bond, that may be further substituted, with multiple degrees of substitution being allowed. An example of "alkynylene" includes, without limitation, ethylene, namely —C≡C—.

The term "aryl" refers to an aromatic ring system, such as an optionally substituted benzene ring system, such as phenyl. The term encompasses fused systems where one or more optionally substituted benzene rings form, for example, anthracene, phenanthrene, or naphthalene ring systems. The term includes ring(s) optionally substituted, with multiple degrees of substitution being allowed, and also includes an optional alkylene linker, such as $C_1$–$C_6$ alkylene, through which the aryl group may be attached. Examples of "aryl" groups include, but are not limited to phenyl, benzyl, 2-naphthyl, 1-naphthyl, biphenyl, as well as substituted derivatives thereof.

The term "heteroaryl" refers to a monocyclic aromatic ring system, or to a fused bicyclic aromatic ring system comprising two or more aromatic rings. These heteroaryl rings contain one or more nitrogen, sulfur, and/or oxygen atoms, where N-oxides, sulfur oxides, and dioxides are permissible heteroatom substitutions. The term includes ring(s) optionally substituted, with multiple degrees of substitution being allowed, and also includes an optional alkylene linker, such as $C_1$–$C_6$ alkylene, through which the heteroaryl group may be attached. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "cycloalkyl" refers to a mono- or bi-cyclic hydrocarbon ring system, which may be further substituted with multiple degrees of substitution being allowed, and which optionally includes an alkylene linker through which the cycloalkyl may be attached. Exemplary "cycloalkyl" groups include, but are not limited to, cyclopropyl, cyclobutyl, cyclopentyl, cyclohexyl, and cycloheptyl. When substituted, one substituent location on cycloalkyl groups of the present invention is at the "1-position." To illustrate, without limitation, a preferred location for a substituent is represented below with the substituent referred to as "R":

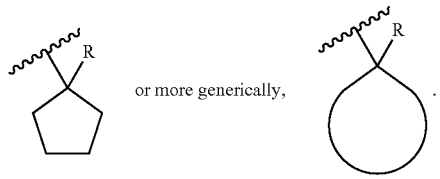

or more generically,

The term "cycloalkyl" includes bridged or fused ring systems, as well, such as hydrindane, decalin, or adamantyl. For ease of reference, also included within the term are cycloalkyl/aryl fused systems where, for example, a cycloalkyl, such as cyclohexyl, is fused with an aromatic ring, such as a benzene ring, to form groups such as

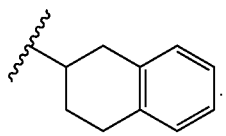

As used herein, the term "heterocyclic" or the term "heterocyclyl" refers to a heterocyclic ring, preferably three to fourteen-membered, that is either saturated or has one or more degrees of unsaturation. These heterocyclic rings contain one or more heteroatom, such as nitrogen, sulfur, and/or oxygen atoms, where N-oxides, sulfur oxides, and dioxides are permissible heteroatom substitutions. As used herein heterocyclic groups optionally may be substituted, with multiple degrees of substitution being allowed, and also includes an optional alkylene linker, such as $C_1$–$C_6$ alkylene, through which the heterocyclyl group may be attached. Such a ring may be optionally fused to one or more of another "heterocyclic" ring(s), aryl ring(s), or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

The term "halogen" refers to fluorine, chlorine, bromine, or iodine.

The term "haloalkyl" refers to an alkyl group, as defined herein that is substituted with at least one halogen. Non-limiting examples of "haloalkyl" groups include methyl, ethyl, propyl, isopropyl, n-butyl, and t-butyl substituted independently with one or more halogens, e.g., fluoro, chloro, bromo, and/or iodo. The term "haloalkyl" should be interpreted to include such substituents as perfluoroalkyl, for example, trifluoromethyl, $CF_3$, and the like.

As used herein, the term "haloalkoxy" refers to the group —$OR_a$, where $R_a$ is haloalkyl as herein defined.

As used herein, the term "alkoxy" refers to the group —$OR_a$, where $R_a$ is alkyl as herein defined.

As used herein, the term "aryloxy" refers to the group —$OR_b$, where $R_b$ is aryl as herein defined.

As an example, and to be applied throughout the specification, since the term "aryl" includes optionally substituted aryl groups, the term "aryloxy" includes optionally substituted aryloxy groups. The optional substitution applies for all applicable terms herein defined. Further, as defined above, the term "aryl" includes alkylene-linked aryl groups. Thus, terms such as "aryloxy" and the like should be considered to include alkylene-linked aryl groups. As an example, therefore, and not meant as limiting, one aryloxy group may be —$OR_b$, where $R_b$ is benzyl, where the benzyl group may be further substituted.

As used herein, the term "heteroaryloxy" refers to the group —$OR_b$, where $R_b$ is heteroaryl as herein defined.

As used herein, the term "alkoxycarbonyl" refers to the group —$C(O)OR_a$, where $R_a$ is alkyl as herein defined.

As used herein, the term "aryloxycarbonyl" refers to the group —$C(O)OR_a$, where $R_a$ is aryl as herein defined.

As used herein, the term "heteroaryloxycarbonyl" refers to the group —$C(O)OR_a$, where $R_a$ is heteroaryl as herein defined.

As used herein, the term "alkoxythiocarbonyl" refers to the group —$C(S)OR_a$, where $R_a$ is alkyl as herein defined.

As used herein, the term "aryloxythiocarbonyl" refers to the group —$C(S)OR_a$, where $R_a$ is aryl as herein defined.

As used herein, the term "heteroaryloxythiocarbonyl" refers to the group —$C(S)OR_a$, where $R_a$ is heteroaryl as herein defined.

As used herein, the term "oxo" refers to the group =O.

As used herein, the term "mercaptol" refers to the group —SH,

As used herein, the term "thio" shall refer to the group —S—.

As used herein, the term "sulfinyl" shall refer to the group —S(O)—.

As used herein, the term "sulfonyl" shall refer to the group —$S(O)_2$—.

As used herein, the term "alkylthio" refers to the group —$SR_a$, where $R_a$ is alkyl as herein defined.

As used herein, the term "arylthio" refers to the group —$SR_b$, where $R_b$ is aryl as herein defined.

As used herein, the term "heteroarylthio" refers to the group —$SR_b$, where $R_b$ is heteroaryl as herein defined.

As used herein, the term "alkylsulfinyl" refers to the group —$S(O)R_a$, where $R_a$ is alkyl as herein defined.

As used herein, the term "arylsulfinyl" refers to the group —S(O)$R_b$, where $R_b$ is aryl as herein defined.

As used herein, the term "heteroarylsulfinyl" refers to the group —S(O)$R_b$, where $R_b$ is heteroaryl as herein defined.

As used herein, the term "alkylsulfonyl" refers to the group —S(O)$_2R_a$, where $R_a$ is alkyl as herein defined.

As used herein, the term "cycloalkylsulfonyl" refers to the group —S(O)$_2R_a$, where $R_a$ is cycloalkyl as herein defined.

As used herein the term "arylsulfonyl" refers to the group —S(O)$_2R_b$, where $R_b$ is aryl as herein defined.

As used herein the term "heteroarylsulfonyl" refers to the group —S(O)$_2R_b$, where $R_b$ is heteroaryl as herein defined.

As used herein, the term "aminosulfonyl" refers to the group —S(O)$_2$NH$_2$.

As used herein, the term "cyano" refers to the group —CN.

As used herein the term "cyanoalkyl" refers to the group —$R_a$CN wherein $R_a$ is an alkylene as herein defined.

As used herein, the term "carboxy" refers to the group —COOH.

As used herein, the term "carbamoyl" refers to the group —C(O)NH$_2$.

As used herein, the term "alkylcarbamoyl" refers to the group —C(O)N($R_a$)$_2$, where one $R_a$ is alkyl and the other $R_a$ is independently H or alkyl.

As used herein, the term "alkylcarbamoyloxy" refers to the group —OC(O)N($R_a$)$_2$, where one $R_a$ is alkyl and the other $R_a$ is independently H or alkyl.

As used herein, the term "arylcarbamoyl" refers to the group —C(O)N($R_a$)$_2$, where one $R_a$ is aryl and the other $R_a$ is independently H or aryl, as herein defined.

As used herein, the term "heteroarylcarbamoyl" refers to the group —C(O)N($R_a$)$_2$, where one $R_a$ is heteroaryl and the other $R_a$ is independently H or heteroaryl, as herein defined.

As used herein, the term "thiocarbamoyl" refers to the group —C(S)NH$_2$.

As used herein, the term "alkylthiocarbamoyl" refers to the group —C(S)N($R_a$)$_2$, where one $R_a$ is alkyl and the other $R_a$ is independently H or alkyl.

As used herein, the term "arylthiocarbamoyl" refers to the group —C(S)N($R_a$)$_2$, where one $R_a$ is aryl and the other $R_a$ is independently H or aryl, as herein defined.

As used herein, the term "heteroarylthiocarbamoyl" refers to the group —C(S)N($R_a$)$_2$, where one $R_a$ is heteroaryl and the other $R_a$ is independently H or heteroaryl, as herein defined.

As used herein, the term "amino" refers to the group —NH$_2$.

As used herein, the term "alkylamino" refers to the group —N($R_a$)$_2$, where one $R_a$ is alkyl and the other $R_a$ independently is H or alkyl, as herein defined.

As used herein, the term "cycloalkylamino" refers to the group —N($R_a$)$_2$, where one $R_a$ is cycloalkyl and the other $R_a$ independently is H or cycloalkyl, as herein defined.

As used herein, the term "arylamino" refers to the group —N($R_a$)$_2$, where one $R_a$ is aryl and the other $R_a$ independently is H or aryl, as herein defined.

As used herein, the term "heteroarylamino" refers to the group —N($R_a$)$_2$, where one $R_a$ is heteroaryl and the other $R_a$ independently is H or heteroaryl, as herein defined.

As used herein, the term "acyl" refers to the group —C(O)$R_a$, where $R_a$ is alkyl, aryl, heteroaryl, cycloalkyl, or heterocyclyl, each as herein defined.

As used herein, the term "thioacyl" refers to the group —C(S)$R_a$ where $R_a$ is alkyl, aryl, heteroaryl, cycloalkyl, or heterocyclyl, each as herein defined.

As used herein, the term "acyloxy" refers to the group —OC(O)$R_a$, where $R_a$ is alkyl, aryl, heteroaryl, cycloalkyl, or heterocyclyl, each as herein defined.

As used herein, the term "thioacyloxy" refers to the group —OC(S)$R_a$, where $R_a$ is alkyl, aryl, heteroaryl, cycloalkyl, or heterocyclyl, each as herein defined.

As used herein, the term "hydroxy" refers to the group —OH.

As used herein the term "hydroxyalkyl" refers to the group —$R_a$OH wherein $R_a$ is an alkylene as herein defined.

The compounds of the present invention may have the ability to crystallize in more than one form, a characteristic known as polymorphism. All polymorphic forms ("polymorphs") are within the scope of the present invention. Polymorphism generally can occur as a response to changes in temperature or pressure, or both, and can also result from variations in the crystallization process. Polymorphs can be distinguished by various physical characteristics that are known in the art such as x-ray diffraction patterns, solubility, and melting point.

Certain of the compounds described herein contain one or more chiral centers, or may otherwise be capable of existing as multiple stereoisomers. The scope of the present invention includes pure stereoisomers as well as mixtures of stereoisomers, such as purified enantiomers/diasteromers or enantiomerically/diastereomerically enriched mixtures. Also included within the scope of the invention are the individual isomers of the compounds per se, as well as any wholly or partially equilibrated mixtures thereof. The present invention covers the individual isomers of the compounds represented by the formulas above as mixtures with isomers thereof in which one or more chiral centers are inverted.

As noted above, the present invention includes salts, solvates, and pharmaceutically functional derivatives of the compounds of the present invention. Salts include addition salts, metal salts, or optionally alkylated ammonium salts. Examples of such salts include hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methane sulphonic, ethane sulphonic, picric, and the like. Further salts include lithium, sodium, potassium, magnesium, and the like. Still further salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, laurate, malate, mandelate, mesylate, methylbromide, methylnitrate, methylsulfate, monopotassium maleate, mucate, napsylate, nitrate, N-methylglucamine, pamoate (embonate), palmitate, pantothenate, phosphate/diphosphate, polygalacturonate, potassium, salicylate, sodium, stearate, subacetate, tannate, tartrate, teoclate, tosylate, triethiodide, trimethylammonium, and valerate salts. Reference is also made to *Journal of Pharmaceutical Science*, 1997, 66, 2, incorporated herein by reference, as relevant to salts.

As used herein, the term "solvate" refers to a complex of variable stoichiometry formed by a solute or a salt or pharmaceutically functional derivative thereof and a solvent. Such solvents for the purpose of the invention should not interfere with the biological activity of the solute. Examples of solvents include, but are not limited to water, methanol, ethanol, and acetic acid. Preferably the solvent used is a pharmaceutically acceptable solvent. Examples of pharmaceutically acceptable solvents include water, ethanol, and acetic acid.

The term "pharmaceutically functional derivative" refers to any pharmaceutically acceptable derivative of a compound of the present invention, for example, an ester or an amide, which upon administration to a mammal is capable of providing (directly or indirectly) a compound of the present invention or an active metabolite or residue thereof. Such derivatives are recognizable to those skilled in the art, without undue experimentation. Nevertheless reference is made to the teaching of *Burger's Medicinal Chemistry and Drug Discovery*, $5^{th}$ Edition, Vol 1: Principles and Practice, which is incorporated herein by reference to the extent of teaching pharmaceutically functional derivatives.

While compounds of the present invention may be administered as the raw chemical, preferably the compounds of the present invention are presented as an active ingredient within a pharmaceutical formulation as known in the art. Accordingly, the present invention further includes a pharmaceutical formulation comprising a compound of the present invention, or salt, solvate, or pharmaceutically functional derivative thereof together with one or more pharmaceutically acceptable carriers. Optionally, other therapeutic and/or prophylactic ("active") ingredients may be included in the pharmaceutical formulation as well. For example, the compounds of the present invention may be combined with other anti-diabetic agents, such as one or more of the following agents: insulin, α-glucosidase inhibitors, biguanides, insulin secretagogue, or insulin sensitizers. Non-limiting examples of α-glucosidase inhibitors include acarbose, emiglitate, miglitol, and voglibose. Non-limiting examples of biguanides include metformin, buformin, and phenformin. Non-limiting examples of insulin secretagogues include sulphonylureas. Non-limiting examples of insulin sensitizers include peroxisome proliferator activated receptor (PPAR) ligands, such as PPAR-γ agonists, for example Actos™ and Avandia™.

Formulations of the present invention include those especially formulated for oral, buccal, parental, transdermal, inhalation, intranasal, transmucosal, implant, or rectal administration. Among the variety of administrations, oral administration typically is preferred. For oral administration tablets, capsules, and caplets may contain conventional excipients such as binding agents, fillers, lubricants, disintegrants, and/or wetting agents. Non-limiting examples of binding agents include syrup, acacia, gelatin, sorbitol, tragacanth, mucilage of starch, or polyvinylpyrrolidone (PVP). Non-limiting examples of fillers include, for example, lactose, sugar, microcrystalline cellulose, maize-starch, calcium phosphate or sorbitol. Non-limiting examples of lubricants include, for example, magnesium sterate, stearic acid, talc, polyethylene glycol or silica. Non-limiting examples of disintegrants include, for example, potato starch or sodium starch glycollate. A non-limiting example of a wetting agent includes sodium lauryl sulfate. The tablets additionally may be coated according to methods known in the art.

Alternatively, the compounds of the present invention may be incorporated into oral liquid preparations such as aqueous or oily suspensions, solutions, emulsions, syrups, or elixirs. Moreover, formulations containing these compounds may be presented as a dry product for constitution with water or other suitable vehicle before use. Liquid preparations may contain conventional additives. Non-limiting examples of such additives include suspending agents such as sorbitol syrup, methyl cellulose, glucose/sugar syrup, gelatin, hydroxyethylcellulose, carboxymethyl cellulose, aluminum sterate gel or hydrogenated edible fats. Additionally, emulsifying agents such as lecithin, sorbitan monooleate or acacia; non-aqueous vehicles (which may include edible oils) such as almond oil, fractionated coconut oil, oily esters, propylene glycol or ethyl alcohol my be included. Further, preservatives such as methyl or propyl p-hydroxybenzoates or sorbic acid, may be incorporated into the preparation. Such preparations may also be formulated as suppositories, for example, containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, for example, sterile, pyrogen-free water, before use.

The formulations according to the invention may also be formulated as a depot preparation. Such long acting formulations may be administered by implantation, for example, subcutaneously or intramuscularly, or by intramuscular injection. Accordingly, the compounds of the invention may be formulated with suitable polymeric or hydrophobic materials, such as an emulsion in an acceptable oil, ion exchange resins, or as sparingly soluble derivatives, such as a sparingly soluble salt.

Pharmaceutical formulations may be presented in unit dose forms containing a predetermined amount of active ingredient per unit dose. Such a unit may contain certain amounts of a compound of the present invention depending on the condition being treated, the route of administration, and the age, weight and condition of the patient. Examples of such amounts include the formulation containing about 0.1 to about 99.9% active ingredient. Preferred unit dosage formulations are those containing a predetermined dose, such as a daily dose, or an appropriate fraction thereof, of an active ingredient. Such pharmaceutical formulations may be prepared by any of the methods well known in the pharmacy art.

As used herein, the term "effective amount" means that amount of a drug or pharmaceutical agent that will elicit the biological or medical response of a tissue, system, animal, or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The therapeutically effective amount of a compound of the present invention will depend upon a number of factors including, for example, the age and weight of the animal, the precise condition requiring treatment and its severity, the nature of the formulation, and the route of administration. Therapeutic effectiveness ultimately will be at the discretion of the attendant physician or veterinarian. An effective amount of a salt or solvate, or pharmaceutically functional derivative thereof, may be determined as a proportion of the effective amount of a compound of the present invention per se. Dosages may vary, depending upon the appropriate inhibition of DPP-IV for purposes of treatment or prophylaxis of a variety of metabolic, gastrointestinal, viral, and inflammatory diseases, including, but not limited to, diabetes, obesity, hyperlipidemia, dermatological or mucous membrane disorders, psoriasis, intestinal distress, constipation, autoimmune disorders such as encephalomyelitis, complement mediated disorders such as glomerulonepritis, lipodystrophy, and tissue damage, HIV infection, allergies, inflammation, arthritis, transplant rejection, high blood pressure, congestive heart failure, tumors, and stress-induced abortions, for example cytokine-mediated murine abortions.

No toxicological effects are indicated/expected when a compound of the present invention is administered in the above mentioned dosage range.

The present invention should be interpreted to cover all combinations of particular and preferred groups herein described. The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims hereto appended.

The following examples illustrate aspects of this invention, but should not be construed as limitations. As used herein the symbols and conventions used in these processes, schemes and examples are consistent with those used in the contemporary scientific literature, for example, the *Journal of the American Chemical Society* or the *Journal of Biological Chemistry*. Unless otherwise noted, all starting materials were obtained from commercial suppliers or through known resources and used without further purification.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FI-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230–400 mesh, Merck). Optical rotations were obtained using a Perkin Elmer Model 241 Polarimeter. Melting points were determined using a Mel-Temp II apparatus and are uncorrected.

IUPAC names are included to further identify particular compounds of the present invention. The IUPAC names stated herein should in no way limit the scope of the present invention.

EXPERIMENTALS

Compounds of the present invention may be prepared according to the preferred scheme detailed below:

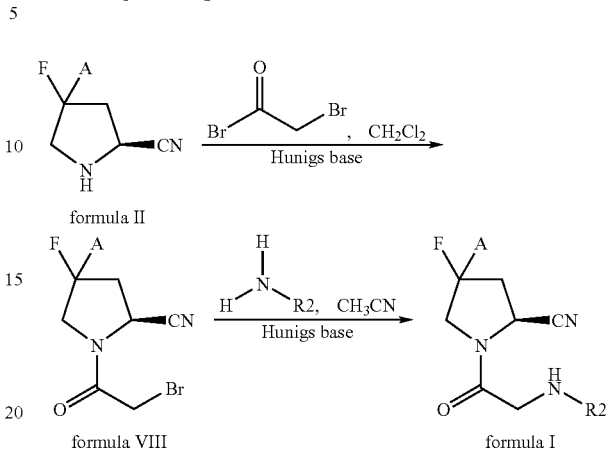

More specifically, a compound of formula (II) can be reacted with an acid halide (for example, bromoacetyl bromide) in an organic solvent (for example methylene chloride) in the presence of an organic base (for example N,N-diisopropylethyl amine) to generate compounds of formula (VIII). Compounds of formula (VIII) can then be reacted with a basic amine in an organic solvent (for example acetonitrile) in the presence of an organic base (for example N,N-diisopropylethyl amine) to generate compounds of formula I.

As an alternative, compounds of the present invention can be generated as outlined below:

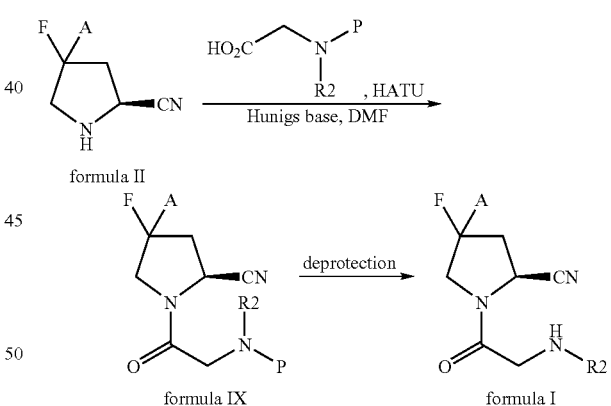

More specifically, a compound of formula (II) can be reacted with a suitably protected amino acid (wherein P designates an appropriate protecting group) in the presence of a coupling agent (for example HATU) with a suitable organic base (for example Hunigs base) in a suitable organic solvent (for example N,N-dimethylformamide) to generate compounds of formula (IX). A compound of formula (IX) can then be deprotected to generate compounds of formula I.

Typical amine protecting groups and their removal can be found in: "Protective Groups in Organic Synthesis" Greene, T. W.; Wuts, P. G. M. Wiley et Sons Third Ed. 1999, herein incorporated by reference as related to amine protecting groups and removal.

Intermediate Example 1

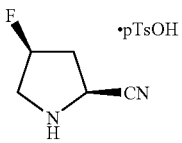

(2S,4S)-4Fluoro-2-pyrrolidinecarbonitrile 4-methylbenzenesulfonate

A. Methyl (2S,4R)-4-hydroxy-2-pyrrolidinecarboxylate hydrochloride.

To a MeOH solution (420 mL) containing L-hydroxyproline (62.67 g, 478 mmol) cooled in an ice water bath was added thionyl chloride (58.6 g, 492.3 mmol) dropwise. Upon complete addition the suspension was stirred at RT for 2 h. The mixture was then heated to reflux for 6 h at which time it was cooled to RT and the solvent removed in vacuo. The residual solid was pumped on under high vacuum yielding 86.03 g (474 mmol, 99% yield) of compound A as a white solid.

$^1$H NMR (d$_4$-MeOH) 400 MHz δ 4.62–4.57 (m, 2H), 3.85 (s, 3H), 3.43 (dd, 1H, J=12.2, 3.7 Hz), 3.30 (m, 1H), 2.41 (dd, 1H, J=13.6, 7.6 Hz), 2.19 (m, 1H) ppm.

B. 1-Tert-butyl-2-methyl (2S,4R)-4-hydroxy-1,2-pyrrolidinedicarboxylate.

To a CH$_2$Cl$_2$ solution (1.4 L) containing compound A (88.67 g, 0.49 mol) and di-t-butyldicarbonate (109.8 g, 0.50 mol) was added, at 0° C., triethylamine (123.6 g, 1.22 mol) dropwise over 1.5 h. The resulting solution was then slowly allowed to warm to RT overnight The solvent was then removed in vacuo and Et$_2$O was added to the residual solid. The solid was collected via vacuum filtration and washed thoroughly with Et$_2$O. The filtrate then had the solvent removed in vacuo and was dissolved in CH$_2$Cl$_2$. The organics were washed with sat. NaCl and sat. NaHCO$_3$ followed by drying over MgSO$_4$. Filtration and removal of the solvent in vacuo yielded a light yellow oil which, after pumping on under high vacuum for ~15 min., solidified. The resulting solid had 500 mL of hexanes added to it and then stirred overnight. The solid was collected via vacuum filtration and pumped on under high vacuum yielding 104.5 g (0.43 mol. 87% yield) compound B as a white solid.

$^1$H NMR (d$_4$-MeOH) 400 MHz δ 4.37–4.32 (m, 2H), 3.72–3.71 (m, 3H), 3.51 (m, 1H), 3.43 (m, 1H), 2.23 (m, 1H), 2.02 (m, 1H), 1.42 (m, 9H) ppm.

C. 1-Tert-butyl 2-methyl (2S,4S)-4-fluoro-1,2-pyrrolidinedicarboxylate.

To a 2 L flask containing compound B (124.25 g, 0.51 mol), in 1.25 L of 1,2-dichloroethane cooled to −30° C., was added DAST neat (125 g, 0.78 mol). The reaction slowly warmed to −10° C. over 1 hr at which time the cold bath was removed. Stirring continued at RT for 24 hr when the dark solution was poured into two 2 L flasks that contained crushed ice and solid NaHCO$_3$. The flasks were periodically swirled and stirred until no CO$_2$ evolution was observed (note: additional solid NaHCO$_3$ was periodically added). The organic layer was separated and the aqueous layer extracted with CH$_2$Cl$_2$. After drying over MgSO$_4$ the solvent was removed in vacuo and the residual dark oil was dissolved in 200 mL of EtOAc and then 800 mL of hexanes was added. To this solution was added 100 g of SiO$_2$. After stirring for 30 min the solution was filtered with the SiO$_2$ being washed with hexanes/EtOAc (4:1,~500 mL). Removal of the solvent in vacuo and pumping on under high vacuum overnight yielded 121.81 g (0.40 mol, 97% yield) of compound C as a dark oil.

$^1$H NMR (CDCl$_3$) 400 MHz δ 5.18 (d(br), 1H, J=53 Hz), 4.53 (d, 1/2H, J=9.7 Hz), 4.40 (d, 1/2H, J=9.4 Hz), 3.87–3.59 (m, 2H), 3.73 (s, 3H), 2.51–2.28 (m, 2H), 1.46 (s, 3H, rotomer), 1.41 (s, 6H, rotomer) ppm.

D. (2S,4S)-1-(Tert-butoxycarbonyl)-4-fluoro-2-pyrrolidinecarboxylic acid.

To a 2 L flask containing compound C (121.8 g, 0.49 mol), in 1.1 L of dioxane, was added 380 mL of H$_2$O followed by lithium hydroxide hydrate (103.6 g, 2.46 mol) at RT. The resulting solution stirred for 23 hr (note: by TLC the reaction appeared to be done after 5 hr.) at which time the bulk of the dioxane was removed in vacuo. The residual material was dissolved in additional H$_2$O and then charcoal was added. After stirring for 15 min., the solution was filtered through a bed of celite. The filtrate had solid NaCl added to it until it didn't dissolve any further. It was then cooled in an ice water bath and was acidified with concentrated HCl to pH 3 whilst maintaining the solution temperature between 5–10° C. The product began to precipitate out at pH 4 and upon reaching pH 3 the tan solid was collected via vacuum filtration. After pumping on under high vacuum overnight the solid was dissolved in CH$_3$CN (1.5 L) and dried over MgSO$_4$. Removal of the solvent in vacuo and drying under high vacuum yielded 92.7 g (0.40 mol. 81% yield) of compound as a tan solid.

$^1$H NMR (d$_6$-DMSO) 400 MHz δ 12.5 (s(br), 1H), 5.22 (d(br), 1H, J=54 Hz), 4.25 (m, 1H), 3.60–3.43 (m, 2H), 2.45 (m, 1H), 2.20 (m, 1H), 1.33 (m, 9H) ppm.

E. Tert-butyl (2S,4S)-2-(aminocarbonyl)-4-fluoro-1-pyrrolidinecarboxylate.

To a 2 L, 3-neck flask equipped with an air-driven stirrer was added compound D (92.7 g, 0.40 mol), CH$_3$CN (1.1 L), di-t-butyidicarbonate (130 g, 0.60 mol), and pyridine (32.4 g, 0.41 mol) at RT. After stirring for 20 min., ammonium hydrogen carbonate (47.2 g, 0.60 mol) was added. The reaction stirred for 23 hr at which time the bulk of the CH$_3$CN was removed in vacuo. The residue was then dissolved in CH$_2$Cl$_2$ and washed with a 1:1 1M HCl/sat NaCl solution. The aqueous layer was then extracted 2× with CH$_2$Cl$_2$. The combined organic layers were dried (MgSO$_4$) and the solvent removed in vacuo. The tan solid was triturated with hexanes (~0.5 L) and collected via vacuum filtration. After pumping under high vacuum, 68.75 g (0.30 mol. 74% yield) compound E was obtained as a light tan solid. The filtrate after removal of the solvent in vacuo gave a dark oil that also appeared to contain additional product by $^1$H NMR.

$^1$H NMR (d$_6$-DMSO) 400 MHz δ 7.21 (s(br), 1/2H), 7.14 (s(br), 1/2H), 6.94 (s(br), 1H), 5.19 (d(br), 1H, J=54 Hz), 4.11 (m, 1H), 3.63–3.47 (m, 2H), 2.38 (m, 1H), 2.11 (m, 1H), 1.39 (s, 3H, rotomer), 1.34 (s, 6H, rotomer) ppm.

F. Tert-butyl (2S,4S)-2-cyano-4-fluoro-1-pyrrolidinecarboxylate.

To a flask containing imidazole (2.93 g, 43.1 mmol), was added pyridine (75 g, 0.9 mol. 15 volumes by weight to the amide). The solution was then cooled to 0° C. and after stirring for 10 min., BOC-4-fluoroproline carboxamide (5.0 g, 21.6 mmol) was added in one portion. The solution was then cooled to −30° C. (note: going below this temperature may lead to a heterogeneous solution) and POCl₃ (13.2 g, 86.4 mmol) was added dropwise over 5 minutes. Upon complete addition the dry-ice acetone bath was replaced with an ice water bath and stirring continued at 0° C. for 1 hr at which time it was poured into a crushed ice, solid NaCl and EtOAc mixture. The organic layer was separated and the aqueous layer was extracted with EtOAc (2×). The solvent was removed in vacuo (note: keep rotovap bath <35° C.) and the residue dissolved in EtOAc. The organics were washed with sat. NaCl and 1.0 M HCl (2×). After drying over MgSO₄ the solvent was removed in vacuo yielding 4.0 g (18.6 mmol, 86% yield) of compound F as a light tan solid.

¹H NMR (d₄-MeOH) 400 MHz δ 5.32 (d(br), 1H, J=52 Hz), 4.78 (m, 1H), 3.74–3.48 (m, 2H), 2.55–2.40 (m, 2H), 1.52–1.43 (m, 9H) ppm.

G. (2S,4S)-4-Fluoro-2-pyrrolidinecarbonitrile4-methylbenzenesulfonate.

To a CH₃CN solution (1 L) containing compound F (56.62 g, 0.26 mol), was added p-toluenesulfonic acid hydrate (75.4 g, 0.40 mol) at RT. After 24 hr the CH₃CN was removed in vacuo and then the residual brown oil was dissolved in 500 mL of EtOAc. Within 1 min a solid precipitated out and the solution was cooled in an ice-water bath and after stirring for 1 hr the solid was collected via vacuum filtration. The collected solid was rinsed with cold (−20° C.) EtOAc (~500 mL) and then pumped on under high vacuum overnight yielding 60.94 g (0.21 mol. 82% yield) of compound G as a light tan solid.

¹H NMR (d₄-MeOH) 400 MHz δ 7.69 (d, 2H, J=8.1 Hz), 7.23 (d, 2H, J=8.0 Hz), 5.52 (dd, 1H, J=51, 3.4 Hz), 4.96 (dd, 1H, J=9.8, 3.6 Hz), 3.78 (m, 1H), 3.55 (m, 1H), 2.84–2.63 (m, 2H), 2.36 (s, 3H) ppm.

Alternative Route for Intermediate Example 1

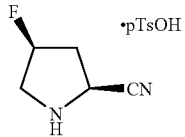

(2S,4S)-4-Fluoro-2-pyrrolidinecarbonitrile 4-methylbenzenesulfonate

A. Tert-butyl (2S,4R)-2-(aminocarbonyl)-4-hydroxypyrrolidine-1-Carboxylate

To a THF solution (420 mL) containing BOC-L-hydroxyproline (30.0 g, 129 mmol) and triethylamine (14.4 g, 141.9 mmol) cooled to −15° C. was added ethyl chloroformate (15.4 g, 141.9 mmol) dropwise. The resulting solution stirred for 10 min when 80 mL of 28% NH₄OH was added. The reaction was allowed to slowly warm to 5° C. over 2 hr at which time sat. NH₄Cl was added until the entire white solid had dissolved. The THF was separated and the aqueous layer extracted with THF. The combined organic layers were dried (MgSO₄) and the solvent removed in vacuo. The residual oil was treated with Et₂O and a small amount of CH₂Cl₂ and MeOH. After storing in the freezer for 1 hr the resulting white solid was collected via vacuum filtration yielding 22.0 g (95.6 mmol, 74% yield) of compound A.

¹H NMR (d₆-DMSO) 400 MHz δ 7.33–7.29 (d(br), 1H, rotomers), 6.88–6.80 (d(br), 1H, rotomers), 4.94 (s(br), 1H), 4.18 (s(br), 1H), 4.04 (m, 1H), 3.35 (m, 1H), 3.21 (m, 1H), 1.99 (m, 1H), 1.77 (m, 1H), 1.36–1.31 (d, 9H, rotomers) ppm.

B. Tert-butyl (2S,4R)-2-cyano-4-hydroxypyrrolidine-1-carboxylate.

To a pyridine solution (180 mL) containing compound A (17.89 g, 77.8 mmol) cooled to −20° C. was added trifluoroacetic anhydride (40.8 g, 194.4 mmol) dropwise. Upon complete addition the reaction was allowed to warm to RT. After 6 hr the reaction was quenched with H₂O and then poured into EtOAc (ca 500 mL). The organics were washed with sat. NaCl, 1.0 M HCl and 2.0 M NaOH followed by drying over MgSO₄. The filtrate had charcoal added to it and after stirring for 10 min the solution was filtered through a bed of celite. The solvent was removed in vacuo (the rotovap temperature was at 34° C.) yielding 13.21 g (62.3 mmol, 80% yield) of compound B as an orange oil.

¹H NMR (d₄-MeOH) 400 MHz δ 4.60 (m, 1H), 4.40 (s(br), 1H), 3.49–3.41 (m, 2H), 2.36–2.34 (m, 2H), 1.51–1.48 (m, 9H, rotomers)

C. Tert-butyl (2S,4S)-2-cyano-4-fluoro-1-pyrrolidinecarboxylate.

To a 1,2-dichloroethane solution (300 mL) containing compound B (13.21 g, 62.3 mmol) cooled to −30° C. was added DAST (15.1 g, 93.4 mmol). After 30 min the cold bath was removed and stirring continued for 24 hr at which time the reaction was quenched carefully with sat. NaHCO₃. The solution was then poured onto crushed ice and the organics extracted with CH₂Cl₂ (2×). After a final washing with sat. NaHSO₄ the organics were dried (MgSO₄) and the solvent removed in vacuo yielding 10.86 g (50.7 mmol, 81% yield) of compound C as a brown semi-solid.

¹H NMR (d₄-MeOH) 400 MHz δ 5.32 (d(br), 1H, J=52 Hz), 4.78 (m, 1H), 3.74–3.48 (m, 2H), 2.55–2.40 (m, 2H), 1.52–1.43 (m, 9H) ppm.

D. (2S,4S)-4-Fluoro-2-pyrrolidinecarbonitrile4-methylbenzenesulfonate.

To an CH₃CN solution (200 mL) containing compound C (10.86 g, 50.7 mmol) was added p-toluenesulfonic acid (14.8 g, 78 mmol) at RT. The resulting solution stirred for 24 hr at which time the CH₃CN was removed in vacuo. The residual brown oil was dissolved in EtOAc (300 mL) and within 1 min a solid precipitated out. The solution was cooled in an ice-bath for 2 hr and then the solid collected via vacuum filtration. It was then washed with 300 mL of cold (−20° C.) EtOAc yielding 10.07 g (35.2 mmol, 69% yield) of compound D.

¹H NMR (d₄-MeOH) 400 MHz δ 7.69 (d, 2H, J=8.1 Hz), 7.23 (d, 2H, J=8.0 Hz), 5.52 (dd, 1H, J=51, 3.4 Hz), 4.96 (dd, 1H, J=9.8, 3.6 Hz), 3.78 (m, 1H), 3.55 (m, 1H), 2.84–2.63 (m, 2H), 2.36 (s, 3H) ppm.

Intermediate Example 2

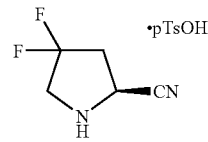

(2S)-4,4-Difluoro-2-pyrrolidinecarbonitrile 4-methylbenzenesulfonate

A. Tert-butyl (2S,4S)-2-(aminocarbonyl)-4-hydroxy-1-pyrrolidinecarboxylate.

To a THF solution (420 mL) containing BOC-L-hydroxyproline (30.0 g, 129 mmol) and $Et_3N$ (14.4 g, 141.9 mmol) cooled to −15° C. was added ethyl chloroformate (15.4 g, 141.9 mmol) dropwise. The resulting white solution stirred at −15° C. for 30 min when 80 mL of a 28% $NH_4OH$ solution was added via syringe. Upon complete addition the cold bath was removed and stirring continued for 19 hr. The homogeneous solution was poured into sat $NH_4Cl$ and the organic layer separated. The aqueous layer was extracted with THF and then the combined organic layers dried ($MgSO_4$). The solvent was removed in vacuo and the semisolid pumped on under high vacuum for 2 hr. The resulting white solid was collected via vacuum filtration with $Et_2O$ yielding 15.86 g (68.9 mmol, 53% yield) of compound A.

$^1$H NMR (d6-DMSO) 400 MHz δ 7.34 (s(br), 1H, rotomer), 7.31 (s(br), 1H, rotomer), 6.90 (s(br), 1H, rotomer), 6.82 (s(br), 1H, rotomer), 4.95 (d, 1H, J=3.1 Hz), 4.05 (m, 1H), 3.36 (m, 1H), 3.22 (m, 1H), 2.03 (m, 1H), 1.78 (m, 1H), 1.37 (s, 3H, rotomer), 1.32 (s, 6H, rotomer) ppm.

B. Tert-butyl (2S)-2-(aminocarbonyl)-4-oxo-1-pyrrolidinecarboxylate.

To a $CH_2Cl_2$ solution (12 mL) containing oxalylchloride (607 mg, 4.78 mmol) cooled to −78° C. was added a $CH_2Cl_2$ solution (3 mL) containing DMSO. After 5 min tert-butyl (2S,4S)-2-(aminocarbonyl)-4-hydroxy-1-pyrrolidinecarboxylate (1.0 g, 4.35 mmol, as described in step E above) in a $CH_2Cl_2$/THF solution (20 mL/15 mL) was added dropwise. Upon complete addition the reaction stirred for 20 min when $Et_3N$ (2.20 g, 21.7 mmol) was added. After 10 min the cold bath was removed and stirring continued for 1 hr. The solution was poured into sat. $NaHCO_3$ and the organics extracted with $CH_2Cl_2$. After drying over $MgSO_4$ the solvent was removed in vacuo and the residual yellow oil purified via column chromatography ($CH_2Cl_2$/MeOH (15:1)) yielding 560 mg (2.45 mmol, 56% yield) of compound B as a white solid.

$^1$H NMR (d$_6$-DMSO) 400 MHz δ 7.58 (s(br), 1H), 7.15 (s(br), 1H, rotomer), 7.09 (s(br), 1H, rotomer), 4.51 (d, 1H, J=9.7 Hz, rotomer), 4.46 (d, 1H, J=8.8 Hz, rotomer), 3.76–3.64 (m, 2H), 3.02 (m, 1H), 2.28 (m, 1H), 1.39 (s, 3H, rotomer), 1.37 (s, 6H, rotomer)ppm.

C. Tert-butyl (2S)-2-(aminocarbonyl)-4,4-difluoro-1-pyrrolidinecarboxylate.

To a $CH_2Cl_2$ solution (10 mL) containing compound B (423 mg, 1.85 mmol) cooled to −70° C. was added DAST (889 mg, 5.50 mmol). The resulting solution stirred at −70 ° C. for 30 min and then at RT for 2 hr. The reaction was quenched with sat. $NaHCO_3$ and the organics extracted with $CH_2Cl_2$. After drying over $MgSO_4$ the residual yellow solid was purified via column chromatography ($CH_2Cl_2$/MeOH (15:1)) yielding 211 mg (0.84 mmol, 46% yield) of compound C.

$^1$H NMR (d$_4$-MeOH) 400 MHz δ 4.38 (m, 1H), 3.84–3.75 (m, 2H), 2.76 (m, 1H), 2.41 (m, 1H), 1.44 (s(br), 9H) ppm.

D. Tert-butyl (2S)-2-cyano-4,4-difluoro-1-pyrrolidinecarboxylate.

To a pyridine solution (20 mL) containing compound C (658 mg, 2.63 mmol) and imidazole (358 mg, 5.26 mmol) cooled to −35° C. was added $POCl_3$ (1.61 g, 10.5 mmol). The resulting slurry stirred for 1.5 hr at which time it had warmed to 10° C. The solution was diluted with EtOAc and them washed 3× with 1 M HCl. After drying over $MgSO_4$ the solvent was removed in vacuo yielding 610 mg (2.63 mmol, 100% yield) of compound D which was taken directly on.

$^1$H NMR (d$_4$-MeOH) 400 MHz δ 4.88 (s(br), 1H), 3.79–3.72 (m, 2H), 2.87 (m, 1H), 2.69 (m, 1H), 1.50 (s, 9H) ppm.

E. (2S)-4,4-Difluoro-2-pyrrolidinecarbonitrile4-methylbenzenesulfonate.

To an $CH_3CN$ solution (15 mL) containing compound D (512 mg, 2.21 mmol) was added p-toluenesulfonic acid hydrate (839 mg, 4.42 mmol) at RT. The resulting solution stirred for 2 hr at which time the $CH_3CN$ was removed in vacuo. To the residual oil was added EtOAc (~10 mL) and this was then removed in vacuo. The resulting solid was triterated with $Et_2O$ followed by addition of EtOAc. The solid was collected via vacuum filtration yielding 375 mg (1.23 mmol, 56% yield) of compound E as a white solid.

$^1$H NMR (d$_4$-MeOH) δ 400 MHz 7.70 (d, 2H, J=8.2 Hz), 7.23 (d, 2H, J=7.9 Hz), 5.12 (t, 1H, J=7.9 Hz), 3.91–3.78 (m, 2H), 3.08–2.89 (m, 2H), 2.89 (s, 3H), 2.36 (s, 9H)ppm.

Intermediate Example 3

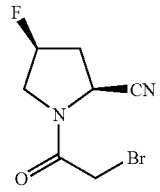

(2S,4S)-1-(Bromoacetyl)-4-fluoro-2-pyrrolidinecarbonitrile

Bromoacetyl bromide (503 μL, 5.77 mmol, 1.1 eq) was taken up in $CH_2Cl_2$ (12 mL) and cooled to 0° C. (2S,4S)-4-Fluoro-2-pyrrolidinecarbonitrile 4-methyl-benzenesulfonate (compound G as described earlier) (1.5 g, 5.24 mmol, 1.0 eq) and diisopropylethylamine (1.0 mL, 5.77 mmol, 1.1 eq) taken up in $CH_2Cl_2$ (7 mL) were added to the bromide solution dropwise over 10 min. The resulting mixture stirred at 0° C. for 2 hr and was then quenched with $H_2O$ and extracted with $CH_2Cl_2$. The organics were dried over $MgSO_4$ and concentrated in vacuo affording 1.2 g (5.24 mmol, 100% yield) of compound A as purple solid which was taken on crude.

$^1$H NMR (d$_4$-MeOH) 400 MHz δ 5.57 (dt(br), 1H, J=51.7 et 3.1 Hz), 5.00 (d, 1H, J=8.6 Hz), 4.20–3.80 (m(br), 4H), 2.61–2.39 (m(br), 2H) ppm.

Intermediate Example 4

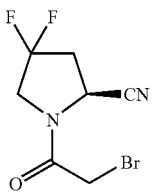

(2S)-1-(Bromoacetyl)-4,4-difluoro-2-pyrrolidinecarbonitrile

To a CH$_2$Cl$_2$ solution (5 mL) containing bromoacetyl bromide (365 mg, 1.80 mmol) cooled to −10° C. was added dropwise (2S)-4,4-difluoro2-pyrrolidinecarbonitrile 4-methylbenzenesulfonate (described earlier) (500 mg, 1.64 mmol) and triethylamine (199 mg, 1.97 mmol) in CH$_2$Cl$_2$ (5 mL). After stirring for 2 hours at 10° C. the reaction was quenched with H$_2$O and the organics extracted with CH$_2$Cl$_2$ and washed with 1.0 M HCl. After drying over MgSO$_4$ the solvents were reduced in vacuo yielding 400 mg (1.57 mmol, 96% yield) of the title compound as a yellow oil.

$^1$H NMR (d$_4$-MeOH) 400 MHz δ 5.06 (d, 1H, J=3.2 Hz), 4.21–4.04 (m, 2H), 4.02 (s, 1H), 2.97–2.72 (m, 2H) ppm.

Example 1

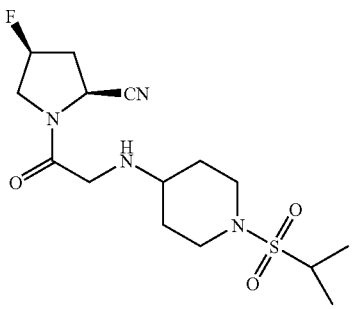

(2S,4S)-4-Fluoro-1-({[1-(isopropylsulfonyl)-4-piperdinyl]amino}acetyl)-2-pyrrolidinecarbonitrile hydrochloride A. Tert-butyl 1-(isopropylsulfonyl)-4-piperdinylcarbamate.

4-N—BOC-aminopiperidine (5.0 g, 25.0 mmol), triethylamine (3.8 mL 27.5 mmol), and 50 mL of dry CH$_3$CN were added to a 100 mL round bottom flask. The resulting mixture was cooled to 0–5° C. and mixed with 2-propanesulfonyl chloride (3.9 g, 27.5 mmol). The reaction was allowed to stir at room temperature for a period of 1.5 hours. The reaction was concentrated to dryness and the resulting solid was partitioned between saturated NaHCO$_3$ and EtOAc. The organics were washed with sat. NaCl and concentrated to dryness to give 6.9 g (91% yield) of compound A as a tan solid which was used without further purification.

$^1$H NMR (CDCl$_3$) 400 MHz δ 4.45 (s(br), 1H), 3.79 (d, 2H, J=13 Hz), 3.58 (s(br), 1H), 3.19–3.12 (m, 1H), 2.96 (t, 2H, J=13.4 Hz), 1.99 (d, 2H, J=12.8 Hz), 1.48–1.38 (m, 11H), 1.32 (d, 6H, J=6.8 Hz) ppm.

B. 1-(Isopropylsulfonyl)-4-piperidinamine hydrochloride.

Compound B (6.5 g, 21.0 mmol) was dissolved into 65 mL of 1,4-dioxane. The mixture was cooled to 0–5° C. and mixed with 4.0 N HCl in 1,4-dioxane (52.5 mL, 0.21 mol). The reaction was stirred at RT for a period of 16.0 hours and was concentrated to dryness in vacuo. The resulting off white solid was triterated in ether and filtered in vacuo. The product was dried under high vacuum to afford 4.9 g (94% yield) of compound B.

$^1$H NMR (d$_4$-MeOH) 400 MHz δ 3.89 (d, 2H, J=13.5 Hz), 3.33–3.26 (m, 2H), 3.05 (t, 2H, J=12.1 Hz), 2.05 (d, 2H, J=12.1 Hz), 1.65–1.55 (m, 2H), 1.31 (d, 6H, J=6.7 Hz)ppm.

C. (2S,4S)-4-Fluoro-1-({[1-(isopropylsulfonyl)-4-piperidinyl]amino}acetyl)-2-pyrrolidinecarbonitrile.

(2S,4S)-1-(Bromoacetyl)-4fluoro-2-pyrrolidinecarbonitrile (described earlier) (1.2 g, 5.24 mmol, 1.0 eq) and compound B (1.4 g, 5.76 mmol, 1.1 eq) were taken up in CH$_3$CN (50 mL, 0.1 M). Diisopropylethylamine (4.6 mL, 26.2 mmol, 5.0 eq) was then added and the resulting mixture stirred at RT overnight The reaction was quenched with 1.0 M NaOH (ca 10 mL) and then was poured into H$_{2O}$. The organics were extracted with EtOAc (3×), combined and dried over Na$_2$SO$_4$. The solvent was concentrated in vacuo and then the residue purified via flash chromatography using an initial mobile phase of 1% MeOH (with 0.1% NH$_3$) in CH$_2$Cl$_2$ then ramping to 5% MeOH (with 0.1% NH$_3$) in CH$_2$Cl$_2$ affording 833 mg (2.3 mmol, 44% yield) of a white fluffy solid. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum yielding compound C as a white solid.

$^1$H NMR (d$_6$-DMSO) 400 MHz δ 9.16 (s(br), 2H), 5.60 (d(br), 1H, J=51.8 Hz), 5.06 (d, 1H, J=8.8 Hz), 4.26 (d, 2H, J=16.5 Hz), 4.02 (t, 2H, J=11.2 Hz), 3.71 (d, 2H, J=12.3 Hz), 3.34–3.22 (m, 1H), 3.21 (t(br), 1H, J=8.3 Hz), 2.95 (t, 2H, J=12.2 Hz), 2.52 (d, 2H, J=15.2 Hz), 2.09 (d, 2H, J=11.2 Hz), 1.58–1.50 (m, 2H), 1.20 (d, 6H, J=6.9 Hz) ppm.

Example 2

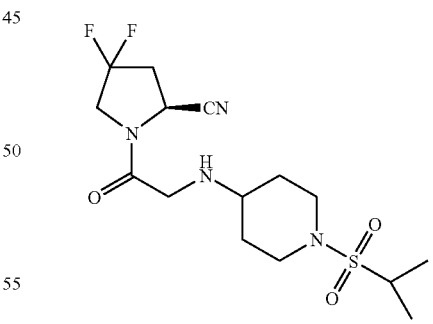

(2S)-4,4-Difluoro-1-({[1-(isopropylsulfonyl)-4-piperidinyl]amino}acetyl)-2-pyrrolidnecarbonitrile A. (2S)-4,4-Difluoro-1-({[1-(isopropylsulfonyl)-4-piperidinyl]amino}acetyl)-2-pyrrolidnecarbonitrile hydrochloride.

To a CH$_2$Cl$_2$ solution (4 mL) containing 1-(isopropylsulfonyl)-4-piperidinamine hydrochloride (described earlier) (300 mg, 1.2 mmol) was added Et$_3$N (249 mg, 2.46 mmol).

The solution was added dropwise to a CH$_2$Cl$_2$ solution (4 mL) containing (2S)-1-(bromoacetyl)-4,4difluoro-2-pyrrolidinecarbonitrile (250 mg, 0.98 mmol) cooled to 0° C. After stirring for 15 min the cold bath was removed and the solution allowed to reach ambient temperature at which it stirred for 4 hours. The solution was quenched with H$_2$O the organics extracted with CH$_2$Cl$_2$ (3×) and combined. After drying over MgSO$_4$ the solvents were reduced in vacuo and the product purified via column chromatography (MeOH/CH$_2$Cl$_2$ (19:1)) yielding 220 mg (581 mmol, 59% yield) of compound A as the free base as a beige solid. To a dioxane solution (2 mL) containing compound A (100 mg, 0.26 mmol) was added 4.0 M HCl in dioxane (0.66mL, 2.64 mmol). After stirring for 2 hours the solvents were reduced in vacuo and the solution triterated with Et$_2$O. A white precipitate crashed out which was collected by vacuum filtration and dried on the high vacuum pump yielding 8.0 mg (0.019 mmol, 7.0% yield) of compound A as a white solid.

$^1$H NMR (d$_4$-MeOH) 400 MHz δ 5.15 (d, 1H, J=9.4 Hz), 4.16 (d, 1H, J=8.6 Hz), 4.09–3.98 (m, 2H), 3.92 (d, 2H, J=13.2 Hz), 3.39–3.26 (m, 3H), 3.04 (t, 2H, J=12.3 Hz), 2.91–2.78 (m, 2H), 2.19 (d, 2H, J=10.7 Hz), 1.71–1.61 (m, 2H), 1.30 (d, 6H, J=6.8 Hz)ppm.

Example 3

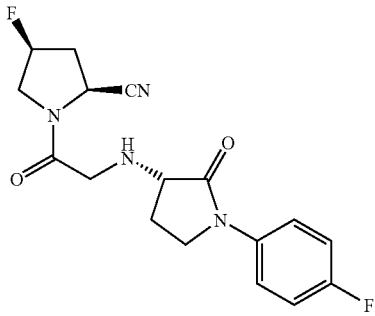

(2S,4S)-4-Fluoro-1-({[(3S)-1-(4-fluorophenyl)-2-oxopyrrolidinyl]amino}acetyl)-2-pyrrolidinecarbonitrile hydrochloride A. Tert-butyl (1S)-1-[(4-fluoroanilino)carbonyl]-3-(methylsulfanyl)propylcarbamate.

To a DMF solution (80 mL) containing BOC—L-methionine (5.0 g, 20.0 mmol) and diisopropylethyl amine (3.89 g, 30.1 mmol) was added HATU (7.6 g, 20.0 mmol) at RT. After 15 min 4-fluoroaniline (2.22 g, 20.0 mmol) in 10 mL of DMF was added. The resulting solution stirred for 2 days at which time the solution was poured into EtOAc and the organics were washed with H$_2$O (3×), 1 M HCl and sat. NaHCO$_3$. After drying over MgSO$_4$ the solvent was removed in vacuo and the residual dark oil purified via column chromatography (hexanes/EtOAc (7:3)) yielding 5.13 g (15.0 mmol, 75% yield) of compound A as a yellow foam.

$^1$H NMR (CDCl$_3$) 400 MHz δ 8.56 (s(br), 1H), 7.45–7.42 (m, 2H), 6.98–6.94 (m, 2H), 5.35 (d(br), 1H, J=7.6 Hz), 4.42 (s(br), 1H), 2.63–2.58 (m, 2H), 2.17 (m, 1H), 2.11 (s, 3H), 2.00 (m, 1H), 1.44 (s, 9H) ppm.

B. Tert-butyl (1S)-3-(dimethylsulfonio)-1-[(4-fluoroanilino)carbonyl]propylcarbamate iodode.

A flask containing compound A (1.73 g, 5.06 mmol) had 22 mL of iodomethane added to it. After stirring overnight the iodomethane was removed in vacuo yielding 2.28 g (4.71 mmol, 93% yield) of compound B which was taken on crude.

$^1$H NMR (d$_6$-DMSO) 400 MHz δ 10.1 (s, 1H), 7.60–7.57 (m, 2H), 7.26 (d, 1H, J=8.1 Hz), 7.17–7.12 (m, 2H), 4.16 (m, 1H), 3.32–3.28 (m, 3H), 2.87 (s, 3H), 2.86 (s, 3H), 2.14–2.00 (m, 2H), 1.37 (s, 9H) ppm.

C. Tert-butyl (3S)-1-(4-fluorophenyl)-2-oxopyrrolidinylcarbamate.

To a THF solution (90 mL) containing compound B (2.28 g, 4.71 mmol) cooled to 0 ° C. was added 4.94 mL of a 1 M THF solution of LiHMDS (4.94 mmol). After 2 hr the reaction was quenched with sat. NaHSO$_4$ and the organics were extracted with EtOAc. The organic layer was then washed with sat. NaHCO$_3$ and sat. NaCl. After drying over MgSO$_4$ the solvent was removed in vacuo and the residual solid was triterated with Et$_2$O. The solid was collected via vacuum filtration and the filtrate also then had the solvent removed in vacuo. After triteration with Et$_2$O the solids were combined yielding 954 mg (3.24 mmol, 69% yield) of compound C as a beige solid.

$^1$H NMR (CDCl$_3$) 400 MHz δ 7.60–7.56 (m, 2H), 7.08–7.04 (m, 2H), 5.22 (s(br), 1H), 4.33 (s(br), 1H), 3.79–3.74 (m, 2H), 2.77 (s(br), 1H), 2.00 (m, 1H), 1.46 (s, 9H) ppm.

D. (3S)-3-Amino-1-(4-fluorophenyl)-2-pyrrolidine trifluoroacetate.

To a CH$_2$Cl$_2$ solution (15 mL) containing compound C (954 mg, 3.24 mmol) was added 1.25 mL of TFA (5 eq). After 30 min an additional 1.25 mL of TFA was added and after 2 hr the solvent was removed in vacuo yielding 998 mg (3.24 mmol, 100% yield) of crude compound D which was taken on.

$^1$H NMR (d$_4$-MeOH) 400 MHz δ 7.69–7.66 (m, 2H), 7.18–7.13 (m, 2H), 4.24 (dd, 1H, J=10.9, 8.7 Hz), 3.99–3.88 (m, 2H), 2.67 (m, 1H), 2.15 (m, 1H) ppm.

E. (2S,4S)-4-Fluoro-1-({[(3S)-1-(4fluorophenyl)-2-oxopyrrolidinyl]amino}acety)-2-pyrrolidinecarbonitrile To a CH$_3$CN solution (12 mL) containing compound D (1.47 g. 4.77 mmol) and diisopropylethyl amine (1.02 g, 7.86 mmol) was added (2S,4S)-1-(bromoacetyl)-4-fluoro-2-pyrrolidinecarbonitrile (described earlier) (560 mg, 2.38 mmol) in 12 mL of CH$_3$CN at RT. After 5 hr the CH$_3$CN was reomved in vacuo and the residual oil dissolved in EtOAc. The organics were washed with sat. NaHCO$_3$, dilute NH$_4$Cl and sat. NaCl. Upon drying over MgSO$_4$ the solvent was removed in vacuo and the residual foam was purified via column chromatography (initially 1% NH$_3$in EtOH/2% MeOH/CH$_2$Cl$_2$ followed by 1% NH$_3$ in EtOH/5% MeOH/CH$_2$Cl$_2$) yielding 211 mg (0.60 mmol, 25% yield) of compound E.

$^1$H NMR (d$_4$-MeOH) 400 MHz δ 7.64–7.60 (m, 2H), 7.13–7.09 (m, 2H), 5.43 (dt, 1H, J=51.5 et 3.1 Hz), 4.98 (d, 1H, J=9.3 Hz), 3.93 (m, 1H), 3.84–3.57 (m, 7H), 2.65–2.31 (m, 3H), 1.95 (m, 1H) ppm.

F. (2S,4S)-4-Fluoro-1-({[(3S)-1-(4-fluorophenyl)-2-oxopyrrolidinyl]amino}acetyl)-2-pyrrolidinecarbonitrile.

To a flask containing compound E (211 mg, 0.60 mmol) dissolved in 2 mL of dioxane was added 2 mL of a 4.0 M dioxane solution of HCl. After 5 min the solvent was removed in vacuo and the residue triterated with Et$_2$O. The Et₂O was then removed in vacuo and the resulting solid triterated with Et₂O and collected via vacuum filtration yielding 218 mg (0.57 mmol, 93% yield) of compound F as an off-white solid.

¹H NMR (d₄-MeOH) 400 MHz δ 7.70–7.67 (m, 2H), 7.18–7.14 (m, 2H), 5.49 (d(br), 1H, J=51.3 Hz), 5.05 (d, 1H, J=9.1 Hz), 4.47 (d, 1H, J=16.3 Hz), 4.40 (m, 1H), 4.22 (d, 1H, J=16.2 Hz), 4.04–3.74 (m, 6H), 2.75–2.40 (m, 2H), 2.27 (m, 1H) ppm.

Example 4

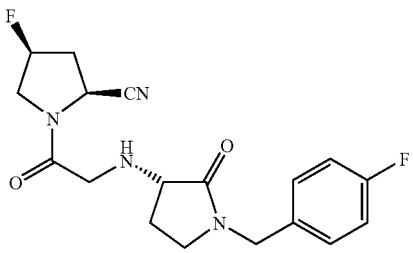

(2S,4S)-4Fluoro-1-({[(3S)-1-(4-fluorobenzyl)-2-oxopyrrolidinyl]amino}acetyl)-2-pyrrolidinecarbonitrile hydrochloride A. Tert-butyl (1S)-1-{[(4-fluorobenzyl)amino]carbonyl}-3-(methylsulfanyl) propylcarbamate.

To a DMF solution (80 mL) containing BOC-L-methionine (5.0 g, 20.0 mmol) was added diisopropylethyl amine (3.89 g, 30.1 mmol) followed by HATU (7.6 g, 20.0 mmol) at RT. After 15 min 4-fluorobenzylamine (2.51 g, 20.0 mmol) was added. The resulting solution stirred overnight at which time the solution was poured into EtOAc. The organics were washed with H₂O (3×), 1.0 M HCl and sat. NaHCO₃. After drying over MgSO₄ the solvent was removed in vacuo and the residual solid triterated with hexanes. Upon pumping on under high vacuum 6.27 g, (17.6 mmol, 88% yield) of compound A was obtained as a tan solid.

¹H NMR (CDCl₃) 400 MHz δ 8.33 (s(br), 1H), 7.27–7.24 (m, 2H), 7.12–7.07 (m, 2H), 7.00 (d, 1H, J=7.7 Hz), 4.23–4.22 (m, 2H), 3.99 (m, 1H), 2.48–2.37 (m, 2H), 1.99 (s, 3H), 1.84–1.74 (m, 2H), 1.36 (s, 9H) ppm.

B. Tert-butyl (1S)-3-(dimethylsulfonio)-1-{[(4-fluorobenzyl)amino]carbonyl}propylcarbamate iodide.

To a flask containing compound A (2.0 g, 5.62 mmol) was added 25 mL of iodomethane at RT. The resulting solution was then gently heated until all the solid was dissolved. The reaction stirred overnight and then the iodomethane was removed in vacuo. The resulting yellow foam was triterated with Et₂O and then the Et₂O removed in vacuo. After pumping on under high vacuum 2.80 g (5.62 mmol, 100% yield) of salt B was obtained as a yellow solid which was taken on crude.

¹H NMR (d₆-DMSO) 400 MHz δ 8.46 (t(br), 1H, J=5.6 Hz), 7.29–7.26 (m, 2H), 7.17 (d, 1H, J=8.3 Hz), 7.13–7.09 (m, 2H), 4.28–4.24 (m, 2H), 4.04 (m, 1H), 3.35–3.27 (m, 2H), 2.87 (s, 3H), 2.86 (s, 3H), 2.08–1.95 (m, 2H), 1.37 (s, 9H) ppm.

C. Tert-butyl (3S)-1-(4-fluorobenzyl)-2-oxopyrrolidinylcarbamate.

To a THF solution (110 mL) containing compound B (2.80 g, 5.62 mmol) cooled to 0° C. was added 6.18 mL of a 1.0 M THF solution of LiHMDS. After stirring for 4 hr at 0° C. the reaction was quenched with sat. NaHSO₄. The organics were extracted with EtOAc and then washed with sat NaHCO₃ and sat. NaCl. After drying over MgSO₄ the solvent was removed in vacuo and the residual orange oil purified via column chromatography (hexanes/EtOAc (1:1)) yielding 1.43 g (4.64 mmol, 83% yield) of compound C.

¹H NMR (CDCl₃) 400 MHz δ 7.21–7.18 (m, 2H), 7.03–6.99 (m, 2H), 5.14 (s(br), 1H), 4.46 (d, 1H, J=14.6 Hz), 4.39 (d, 1H, J=14.6 Hz), 4.18 (s(br), 1H), 3.20–3.17 (dd, 1H, J=9.55, 3.9 Hz), 2.60 (m, 1H), 1.82 (m, 1H), 1.44 (s, 9H) ppm.

D. (3S)-3-Amino-1-(4-fluorobenzyl)-2-pyrrolidine trifluoroacetate.

To a CH₂Cl₂ solution (20 mL) containing compound C (1.42 g, 4.61 mmol) was added 1.8 mL of TFA at RT. After 30 min an additional 1.8 mL of TFA was added. Stirring continued for a total of 1 hr at which time the solvent was removed in vacuo yielding 1.48 g (4.61 mmol, 100% yield) of compound D which was taken on crude.

¹H NMR (CDCl₃) 400 MHz δ 11.2 (s(br), 1H), 8.27 (s(br), 1H), 7.17–7.13 (m, 2H), 7.03–6.99 (m, 2H), 4.46 (d, 1H, J=14.6 Hz), 4.38 (d, 1H, J=14.6 Hz), 4.24 (t(br), 1H J=8.9 Hz), 3.39–3.30 (m, 2H), 2.57 (m, 1H), 2.24 (m, 1H) ppm.

E. (2S,4S)-4Fluoro-1-({[(3S)-1-(4-fluorobenzyl)-2-oxopyrrolidinyl]amino}acetyl)-2-pyrrolidinecarbonitrile.

To an CH₃CN solution (10 mL) containing compound D (1.26 g, 3.90 mmol) and diisopropylethyl amine (756 mg, 5.85 mmol) was added and CH₃CN solution (10 mL) containing (2S,4S)-1-(bromoacetyl)-4-fluoro-2-pyrrolidinecarbonitrile (described earlier) (459 mg, 1.95 mmol) at RT. The resulting solution stirred for 4.5 hr at which time the bulk of the CH₃CN was removed in vacuo. The residual oil was purified via column chromatography (initially 2% NH₃ in EtOH/CH₂Cl₂ to 10% NH₃ in EtOH/CH₂Cl₂) yielding 330 mg (0.91 mmol, 47% yield) of compound E.

¹H NMR (d₄-MeOH) 400 MHz δ 7.30–7.26 (m, 2H), 7.08–7.04 (m, 2H), 5.43 (d, t, 1H, J=51.5, 3.2 Hz), 4.97 (d, 1H, J=9.3 Hz), 4.48–4.38 (m, 2H), 3.98–3.56 (m, 4H), 3.27–3.22 (m, 2H), 2.51 (m, 1H), 2.36 (m, 1H), 1.79 (m, 1H) ppm.

F. (2S,4S)-4Fluoro-1-({[(3S)-1-(4-fluorobenzyl)-2-oxopyrrolidinyl]amino}acetyl)-2-pyrrolidinecarbonitrile hydrochloride.

To a Et₂O (1 mL)/dioxane (2 mL)/MeOH (0.5 mL) solution containing compound E (218 mg, 0.60 mmol) was added 2.0 mL of a 4.0 M dioxane solution of HCl. After 10 min the solvent was removed in vacuo and the residue triterated with Et₂O. The Et₂O was removed in vacuo and the residual solid pumped on under high vacuum. The solid was triturated with Et₂O and collected via vacuum filtration yielding 189 mg (0.47 mmol, 79% yield) of compound F as an off-white solid.

¹H NMR (d₄-MeOH) 400 MHz δ 7.35–7.31 (m, 2H), 7.10–7.06 (m, 2H), 5.48 (d(br), 1H, J=51.5 Hz), 5.03 (d, 1H, J=9.3 Hz), 4.86–4.44 (m, 2H), 4.33–4.16 (m, 2H), 3.98 (m, 1H), 3.79 (ddd, 1H, J=37.2, 12.1, 3.3 Hz), 3.39–3.34 (m, 2H), 2.71–2.39 (m, 2H), 2.07 (m, 1H) ppm.

Example 5

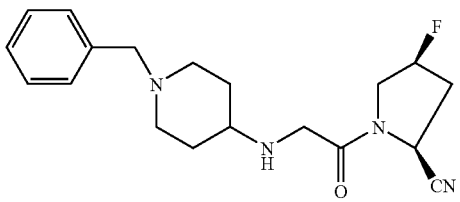

(2S,4S)-1-{[(1-Benzylpiperidin-4-yl)amino]acetyl}-4-fluoropyrrolidine-2-carbonitrile hydrochloride A. (2S,4)-1-{[(1-Benzylpiperidin-4-yl)amino]acetyl}-4-fluoropyrrolidine-2-carbonitrile (2S,4S)-1-(Bromoacetyl)-4-fluoropyrrolidine-2-carbonitrile (described earlier) (411 mg, 1.75 mmol, 1.0 eq) and 4-amino-1-benzylpiperidine (393 µL, 1.93 mmol, 1.1 eq) were taken up in $CH_3CN$ (20 mL, 0.1 M). N,N-diisopropylethylamine (610 µL, 3.5 mmol, 2.0 eq) was then added and the resulting mixture stirred at RT overnight. The reaction was quenched with 1.0 M NaOH (ca 5 mL) and then poured into $H_2O$. The organics were extracted with EtOAc (3×), combined and dried over $Na_2SO_4$. The solvent was concentrated in vacuo and then the residue purified via flash chromatography using an initial mobile phase of 1% MeOH (with 0.1% $NH_3$) in $CH_2Cl_2$ then ramping to 5% MeOH (with 0.1% $NH_3$) in $CH_2Cl_2$ affording 202 mg (0.586 mmol, 33% yield) of a white fluffy solid. To form the HCl salt, the free base was taken up in $Et_2O$ and acetone added until all solids were in solution. 2.0 M HCl in ether was added dropwise until no more precipitate formed. The precipitate was then filtered and washed several times with $Et_2O$. The resulting salt was dried under high vacuum.

$^1$H NMR ($D_2O$) 400 MHz δ 7.38–7.33 (m, 5H), 5.45 (d, 1H, J=50.5 Hz), 4.91 (d, 1H, J=9.4 Hz), 4.19 (s, 2H), 4.05 (ABq, 2H, J=43.6, 16.4 Hz), 3.83 (m, 1H), 3.63 (m, 1H), 3.52 (d, 2H, J=12.6 Hz), 3.41 (m, 1H), 3.04 (t, 2H, J=12.5 Hz), 2.60 (t, 1H, J=15.3 Hz), 2.37 (m, 1H), 2.27 (d, 2H, J=13.8 Hz), 1.85–1.74 (m, 2H) ppm.

Example 6

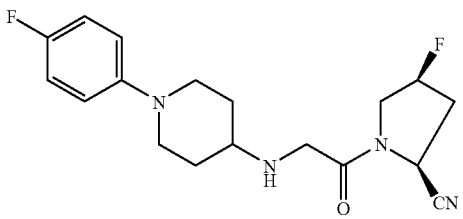

(2S,4S)-4-Fluoro-1-({[1-(4-fluorophenyl)piperidin-4-yl]amino}acetyl)pyrrolidine-2-carbonitrile hydrochloride A. Tert-butyl 1-(4-fluorophenyl)piperidin-4-ylcarbamate.

To a p-xylene (25 mL) solution containing 4-fluorobromobenzene (275 µL, 2.5 mmol, 1.0 eq), 4-N—BOC-aminopiperidine (1.0 g, 4.99 mmol, 2.0 eq), and potassium t-butoxide (393 mg, 3.5 mmol, 1.4 eq) was added palladium (II) acetate (6 mg, 1 mol %) and tri-t-butylphosphine (20 mg, 4 mol %). The resulting mixture was then heated to 120° C. for 4 h at which time it was poured into a sat. $NaHCO_3$ solution and extracted (2×) with EtOAc. The combined extracts were dried over $MgSO_4$ and concentrated in vacuo. The resulting oil was purified via column chromatography using 1:1 hexanes/EtOAc as the mobile phase. Isolated 485 mg (1.65 mmol, 67% yield).

$^1$H NMR ($CDCl_3$) 400 MHz δ 6.96–6.84 (m, 4H), 4.48 (s(br), 1H), 3.58 (s(br), 1H), 3.48 (d, 2H, J=12.8 Hz), 2.81 (t, 2H, J=12.3 Hz), 2.06 (d, 2H, J=12.0 Hz), 1.58–1.52 (m, 11H) ppm.

B. 1-(4-Fluorophenyl)piperidin-4-amine.

Compound A (485 mg, 1.65 mmol, 1.0 eq) was added to a stirred mixture of 4.0 M HCl in dioxane (2.9 mL) and 2.0 M HCl in $Et_2O$ (2.9 mL). The resulting mixture was stirred at RT for 18 h at which time $Et_2O$ was added, the resulting white precipitate filtered, and washed several times with $Et_2O$. The resulting salt was dried under high vacuum. Isolated 285 mg (1.24 mmol, 75% yield) of a tan solid. Used in next step without further purification.

C. (2S,4S)-4-Fluoro-1-({[1-(4-fluorophenyl)piperidin-4-yl]amino}acetyl)pyrrolidine-2-carbonitrile (2S,4S)-1-(Bromoacetyl)-4-fluoropyrrolidine-2-carbonitrile (described earlier) (265 mg, 1.13 mmol, 1.0 eq) and compound B (285 mg, 1.24 mmol, 1.1 eq) were taken up in $CH_3CN$ (15 mL, 0.1M). N,N-diisopropylethylamine (433 µL, 2.49 mmol, 2.2 eq) was then added and the resulting mixture stirred at RT overnight. The reaction was quenched with 1.0 M NaOH (ca 5 mL) and then poured into $H_2O$. The organics were extracted with EtOAc (3×), combined and dried over $Na_2SO_4$. The solvent was concentrated in vacuo and then the residue purified via flash chromatography using an initial mobile phase of 1% MeOH (with 0.1% $NH_3$) in $CH_2Cl_2$ then ramping to 3% MeOH (with 0.1% $NH_3$) in $CH_2Cl_2$ affording 112 mg (0.321 mmol, 28% yield) of a tan fluffy solid. To form the HCl salt, the free base was taken up in $Et_2O$ and acetone added until all solids were in solution. 2.0 M HCl in ether was added dropwise until no more precipitate formed. The precipitate was then filtered and washed several times with $Et_2O$. The resulting salt was dried under high vacuum.

$^1$H NMR ($d_4$-MeOH) 400 MHz δ 7.49 (s(br), 2H), 7.24 (t, 2H, J=8.1 Hz), 5.56 (d, 1H, J=50.8 Hz), 5.07 (d, 1H, J=9.3 Hz), 4.32 (Abq, 2H, J=64.9, 16.4 Hz), 4.03 (m, 1H), 3.88–3.75 (m, 3H), 3.55 (m, 1H), 3.41 (t, 2H, J=12.3 Hz), 2.67–2.39 (m, 4(m, 4), 2.19–2.09 (m, 2H) ppm.

Example 7

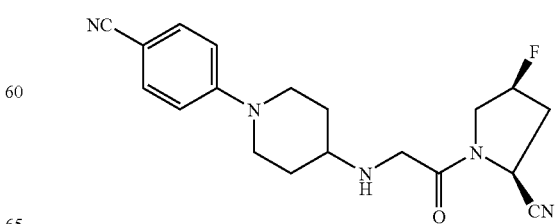

(2S,4S)-1-({[1-(4-Cyanophenyl)piperidin-4-yl]amino}acetyl)4-fluoropyrrolidine-2-carbonitrile hydrochloride A. Tert-butyl 1-(4-cyanophenyl)piperidin-4-ylcarbamate.

A DMSO (25 mL, 0.1M) solution containing 4-N—BOC-aminopiperidine (500 mg, 2.5 mmol, 1.0 eq), 4-fluorobenzonitrile (303 mg, 2.5 mmol, 1.0 eq), and potassium carbonate (691 mg, 5.0 mmol, 2.0 eq) was heated to 100° C. for 18 h. The resulting mixture was cooled to RT, poured in H$_2$O (ca 50 mL), and extracted (3×) with EtOAc. The combined extracts were washed (2×) with H$_2$O, dried over MgSO$_4$, and concentrated in vacuo. The resulting solid was used in the next step without further purification. Isolated 642 mg (2.13 mmol, 85% yield).

$^1$H NMR (CDCl$_3$) 400 MHz δ 7.48 (d, 2H, J=9.1 Hz), 6.86 (d, 2H, J=9.2 Hz), 4.46 (s(br), 1H), 3.79 (d, 2H, J=13.1 Hz), 3.68 (s(br), 1H), 3.01 (t, 2H, J=14.3 Hz) 2.06 (d, 2H, J=13.6 Hz), 1.51–1.41 (m, 11H) ppm.

B. 4-(4-Aminopiperidin-1-yl)benzonitrile.

To a CH$_2$Cl$_2$ (50 mL) solution containing trifluoroacetic acid (2.5 mL) was added compound A (642 mg, 2.13 mmol, 1.0 eq). The resulting pale yellow solution was stirred at RT for 18 h at which time the solvent was removed in vacuo. The resulting TFA salt was used in the next step without further purification. Isolated 618 mg (2.13 mmol, 100% yield) of an amber semi-solid.

$^1$H NMR (d$_6$-DMSO) 400 MHz δ 7.83 (s(br), 2H), 7.58 (d, 2H, J=9.1 Hz), 7.03 (d, 2H, J=9.3 Hz), 3.98 (d, 2H, J=13.3 Hz), 3.28 (m, 1H), 2.96 (t, 2H, J=12.2 Hz), 1.91 (d, 2H, J=15.2 Hz), 1.51–1.41 (m, 2H) ppm.

C. (2S,4S)-1-({[1-(4-Cyanophenyl)piperidin-4-yl]amino}acetyl)-4-fluoropyrrolidine-2-carbonitrile.

(2S,4S)-1-(Bromoacetyl)-4-fluoropyrrolidine-2-carbonitrile (described earlier) (501 mg, 2.13 mmol, 1.0 eq) and compound B (618 mg, 2.13 mmol, 1.0 eq) were taken up in CH$_3$CN (25 mL, 0.1M). N,N-diisopropylethylamine (779 μL, 4.47 mmol, 2.1 eq) was then added and the resulting mixture stirred at RT overnight. The reaction was quenched with 1.0 M NaOH (ca 10 mL) and then poured into H$_2$O. The organics were extracted with EtOAc (3×), combined and dried over Na$_2$SO$_4$. The solvent was concentrated in vacuo and then the residue purified via flash chromatography using an initial mobile phase of 1% MeOH (with 0.1% NH$_3$) in CH$_2$Cl$_2$ then ramping to 3% MeOH (with 0.1% NH$_3$) in CH$_2$Cl$_2$ affording 276 mg (0.777 mmol, 36% yield) of a tan fluffy solid. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum.

$^1$H NMR (D$_2$O) 400 MHz δ 7.51 (d, 2H, J=9.2 Hz), 6.97 (d, 2H, J=9.2 Hz), 5.47 (d, 1H, J=50.7 Hz), 4.92 (d, 1H, J=9.5 Hz), 4.08 (Abq, 2H, J=46.7, 16.6 Hz), 3.89–3.81 (m, 3H), 3.65 (m, 1H), 3.38 (m, 1H), 2.86 (t, 2H, J=11.9 Hz), 2.61 (t, 1H, J=16.2 Hz), 2.38 (m,1H), 2.08 (d, 2H, J=16.7 Hz), 1.65–1.54 (m, 2H) ppm.

Example 8

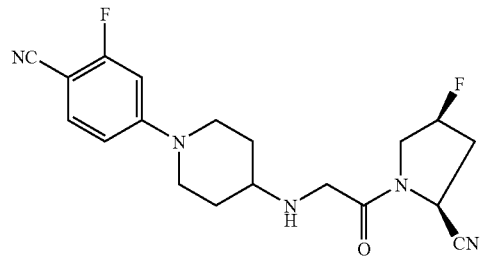

(2S,4S)-1-({[1-(4-Cyano-3-fluorophenyl)piperidin-4-yl]amino}acetyl)-4-fluoropyrrolidine-2-carbonitrile hydrochloride A. Tert-butyl 1-(4-cyano-3-fluorophenyl)piperidin-4-ylcarbamate.

A DMSO (25 mL, 0.1 M) solution containing 4-N—BOC-aminopiperidine (500 mg, 2.5 mmol, 1.0 eq), 2,4-difluorobenzonitrile (348 mg, 2.5 mmol, 1.0 eq), and potassium carbonate (691 mg, 5.0 mmol, 2.0 eq) was heated to 100° C. for 18 h. The resulting mixture was cooled to RT, poured in H$_2$O (ca 50 mL), and extracted (3×) with EtOAc. The combined extracts were washed (2×) with H$_2$O, dried over MgSO$_4$, and concentrated in vacuo. The resulting solid was purified via flash chromatography using 1:1 hexanes/EtOAc as the mobile phase. Isolated 530 mg (1.66 mmol, 66% yield).

$^1$H NMR (CDCl$_3$) 400 MHz δ 7.40 (t, 1H, J=8.8 Hz), 6.62 (d, 1H, J=9.0 Hz), 6.56 (d, 1H, J=13.0 Hz), 4.45 (s(br), 1H), 3.78–3.66 (m, 3H), 3.04 (t, 2H, J=11.7 Hz), 2.06 (d, 2H, J=12.6 Hz), 1.49–1.39 (m, 11H) ppm.

B. 4-(4-Aminopiperidin-1-yl)-2-fluorobenzonitrile.

To a CH$_2$Cl$_2$ (40 mL) solution containing trifluoroacetic acid (4 mL) was added compound A (530 mg, 1.66 mmol, 1.0 eq). The resulting pale yellow solution was stirred at RT for 18 h at which time the solvent was removed in vacuo. The resulting TFA salt was used in the next step without further purification. Isolated 553 mg (1.66 mmol, 100% yield) of an amber semi-solid.

$^1$H NMR (d$_4$-MeOH) 400 MHz δ 7.50 (t, 1H, J=8.3 Hz), 6.86–6.83 (m, 2H), 4.08 (d, 2H, J=13.8 Hz), 3.39 (m, 1H), 3.06 (t, 2H, J=12.3 Hz), 2.08 (d, 2H, J=11.9 Hz), 1.67–1.58 (m, 2H) ppm.

C (2S,4S)1-({[1-(4-Cyano-3-fluorophenyl)piperidin-4-yl]amino}acetyl)-4-fluoropyrrolidine-2-carbonitrile.

(2S,4S)-1-(Bromoacetyl)-4-fluoropyrrolidine-2-carbonitrile (described earlier) (449 mg, 1.91 mmol, 1.0 eq) and compound B (700 mg, 2.1 mmol, 1.1 eq) were taken up in CH$_3$CN (25 mL, 0.1M). N,N-diisopropylethylamine (699 μL, 4.01 mmol, 2.1 eq) was then added and the resulting mixture stirred at RT overnight. The reaction was quenched with 1.0 M NaOH (ca 10 mL) and then poured into H$_2$O. The organics were extracted with EtOAc (3×), combined and dried over Na$_2$SO$_4$. The solvent was concentrated in vacuo and then the residue purified via flash chromatography using an initial mobile phase of 1% MeOH (with 0.1% NH$_3$) in CH$_2$Cl$_2$ then ramping to 30% MeOH (with 0.1% NH$_3$) in CH$_2$Cl$_2$ affording 266 mg (0.712 mmol, 37% yield) of a tan fluffy solid. To form the HCl salt, the free base was taken up in Et₂O and acetone added until all solids were in solution. 2.0 M HCl in ether was added dropwise until no more precipitate formed. The precipitate was then filtered and washed several times with Et₂O. The resulting salt was dried under high vacuum.

¹H NMR (d₄-MeOH) 400 MHz δ 7.50 (t, 1H, J=7.7 Hz), 6.86–6.83 (m, 2H), 5.55 (d, 1H, J=51.3 Hz), 5.05 (d, 1H, J=9.5 Hz), 4.26–3.73 (m, 6H), 3.46 (m, 1H), 3.04 (t, 2H, J=12.8 Hz), 2.71–2.39 (m, 2H), 2.22 (d, 2H, J=10.5 Hz), 1.74–1.63 (m, 2H) ppm.

Example 9

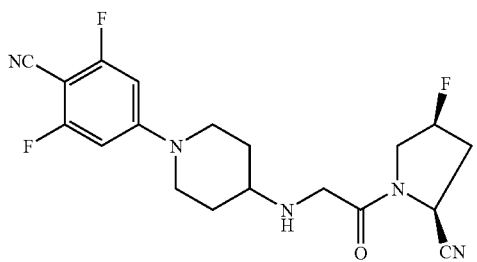

(2S,4S)-1-({[1-(4-Cyano-3,5-difluorophenyl)piperidin-4-yl]amino}acetyl)-4-fluoropyrrolidine-2-carbonitrile hydrochloride A. Tert-butyl 1-(4-cyano-3,5-difluorophenyl)piperidin-4-ylcarbamate A DMSO (25 mL, 0.1M) solution containing 4-N—BOC-aminopiperidine (500 mg, 2.5 mmol, 1.0 eq), 2,4,6-trifluorobenzonitrile (393 mg, 2.5 mmol, 1.0 eq), and potassium carbonate (691 mg, 5.0 mmol, 2.0 eq) was heated to 100° C. for 18 h. The resulting mixture was cooled to RT, poured in H₂O (ca 50 mL), and extracted (3×) with EtOAc. The combined extracts were washed (2×) with H₂O, dried over MgSO₄, and concentrated in vacuo. The resulting solid was purified via flash chromatography using 1:1 hexanes/EtOAc as the mobile phase. Isolated 594 mg (1.76 mmol, 70% yield).

¹H NMR (CDCl₃) 400 MHz δ 6.37 (d, 2H, J=11.3 Hz), 4.46 (s(br), 1H), 3.76–3.69 (m, 3H), 3.07 (t, 2H, J=11.4 Hz), 2.08 (d, 2H, J=12.8 Hz), 1.48–1.38 (m, 11H) ppm.

B. 4-(4-Aminopiperidin-1-yl)-2,6-difluorobenzonitrile.

To a CH₂Cl₂ (40 mL) solution containing trifluoroacetic acid (4 mL) was added compound A (594 mg, 1.76 mmol, 1.0 eq). The resulting pale yellow solution was stirred at RT for 18 h at which time the solvent was removed in vacuo. The resulting TFA salt was used in the next step without further purification. Isolated 620 mg (1.76 mmol, 100% yield) of an amber semi-solid.

¹H NMR (d₄-MeOH) 400 MHz δ 6.75 (d, 2H, J=12.1 Hz), 4.08 (d, 2H, J=13.9 Hz), 3.40 (m, 1H), 3.10 (t, 2H, J=12.2 Hz), 2.09 (d, 2H, J=11.9 Hz), 1.65–1.55 (m, 2H) ppm.

C. (2S,4S)-1-({[1-(4-Cyano-3,5-difluorophenyl)piperidin-4-yl]amino}acetyl)-4-fluoropyrrolidine-2-carbonitrile.

(2S,4S)-1-(Bromoacetyl)-4-fluoropyrrolidine-2-carbonitrile (described earlier) (376 mg, 1.60 mmol, 1.0 eq) and compound B (620 mg, 1.76 mmol, 1.1 eq) were taken up in CH₃CN (20 mL, 0.1M). N,N-diisopropylethylamine (585 μL, 3.36 mmol, 2.1 eq) was then added and the resulting mixture stirred at RT overnight. The reaction was quenched with 1.0 M NaOH (ca 5 mL) and then poured into H₂O. The organics were extracted with EtOAc (3×), combined and dried over Na₂SO₄. The solvent was concentrated in vacuo and then the residue purified via flash chromatography using an initial mobile phase of 1% MeOH (with 0.1% NH₃) in CH₂Cl₂ then ramping to 3% MeOH (with 0.1% NH₃) in CH₂Cl₂ affording 235 mg (0.6 mmol, 38% yield) of a tan fluffy solid. To form the HCl salt, the free base was taken up in Et₂O and acetone added until all solids were in solution. 2.0 M HCl in ether was added dropwise until no more precipitate formed. The precipitate was then filtered and washed several times with Et₂O. The resulting salt was dried under high vacuum.

¹H NMR (d₄-MeOH) 400 MHz δ 6.76 (d, 2H, J=11.9 Hz), 5.55 (d, 1H, J=51.2 Hz), 5.05 (d, 1H, J=9.3 Hz), 4.26–3.73 (m, 6H), 3.47 (m, 1H), 3.09 (t, 2H, J=14.5 Hz), 2.66–2.40 (m, 2H), 2.22 (d, 2H, J=10.0 Hz), 1.71–1.61 (m, 2H) ppm.

Example 10

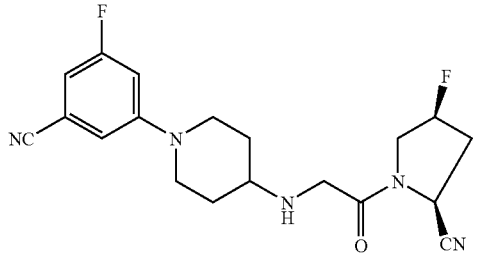

(2S,4S)-1-({[1-(3-Cyano-5-fluorophenyl)piperidin-4-yl]amino}acetyl)-4-fluoropyrrolidin-2-carbonitrile hydrochloride A. Tert-butyl 1-(3-cyano-5-fluorophenyl)piperidin-4-ylcarbamate A DMSO (25 mL, 0.1M) solution containing 4-N—BOC-aminopiperidine (500 mg, 2.5 mmol, 1.0 eq), 3,5-difluorobenzonitrile (348 mg, 2.5 mmol, 1.0 eq), and potassium carbonate (691 mg, 5.0 mmol, 2.0 eq) was heated to 100° C. for 18 h. The resulting mixture was cooled to RT, poured in H₂O (ca 50 mL), and extracted (3×) with EtOAc. The combined extracts were washed (2×) with H₂O, dried over MgSO₄, and concentrated in vacuo. The resulting solid was purified via flash chromatography using 1:1 hexanes/EtOAc as the mobile phase. Isolated 677 mg (2.12 mmol, 85% yield).

¹H NMR (CDCl₃) 400 MHz δ 6.88 (s, 1H), 6.76–6.72 (m, 2H), 4.46 (s(br), 1H), 3.69–3.58 (m, 3H), 2.95 (t, 2H, J=11.4 Hz), 2.06 (d, 2H, J=11.5 Hz), 1.52–1.40 (m, 11H) ppm.

B. 3-(4-Aminopiperidin-1-yl)-5-fluorobenzonitrile.

To a CH₂Cl₂ (40 mL) solution containing trifluoroacetic acid (4 mL) was added compound A (677 mg, 2.12 mmol, 1.0 eq). The resulting pale yellow solution was stirred at RT for 18 h at which time the solvent was removed in vacuo. The resulting TFA salt was used in the next step without further purification. Isolated 707 mg (2.12 mmol, 100% yield) of an amber semi-solid.

¹H NMR (d₆-DMSO) 400 MHz δ 7.82 (s(br), 2H), 7.22 (s, 1H), 7.14 (d, 1H, J=13.0 Hz), 7.04 (d, 1H, J=8.1 Hz), 3.90

(d, 2H, J=13.5 Hz), 3.24 (m, 1H), 2.90 (t, 2H, J=12.3 Hz), 1.88 (d, 2H, J=13.6 Hz), 1.52–1.42 (m, 2H) ppm.

C. (2S,4S)-1-({[1-(3-Cyano-5-fluorophenyl)piperidin-4-yl]amino}acetyl)-4-fluoropyrrolidine-2-carbonitrile.

(2S,4S)-1-(Bromoacetyl)-4-fluoropyrrolidine-2-carbonitrile (described earlier) (454 mg, 1.93 mmol, 1.0 eq) and compound B (707 mg, 2.12 mmol, 1.1 eq) were taken up in CH$_3$CN (25 mL, 0.1M). N,N-diisopropylethylamine (706 µL, 4.05 mmol, 2.1 eq) was then added and the resulting mixture stirred at RT overnight. The reaction was quenched with 1.0 M NaOH (ca 5 mL) and then poured into H$_2$O. The organics were extracted with EtOAc (3×), combined and dried over Na$_2$SO$_4$. The solvent was concentrated in vacuo and then the residue purified via flash chromatography using an initial mobile phase of 1% MeOH (with 0.1% NH$_3$) in CH$_2$Cl$_2$ then ramping to 2% MeOH (with 0.1% NH$_3$) in CH$_2$Cl$_2$ affording 269 mg (0.721 mmol, 37% yield) of a tan fluffy solid. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum.

$^1$H NMR (d$_6$-DMSO) 400 MHz δ 9.15 (s(br), 1H), 7.26 (s, 1H), 7.17 (d, 1H, J=13.1 Hz), 7.07 (d, 1H, J=8.0 Hz), 5.61 (d, 1H, J=52.1 Hz), 5.06 (d, 1H, J=9.0 Hz), 4.28–3.77 (m, 6H), 3.23 (m, 1H), 2.82 (t, 2H, J=12.8 Hz), 2.56–2.31 (m, 2H), 2.09 (d, 2H, J=11.4 Hz), 1.65–1.54 (m, 2H) ppm.

Example 11

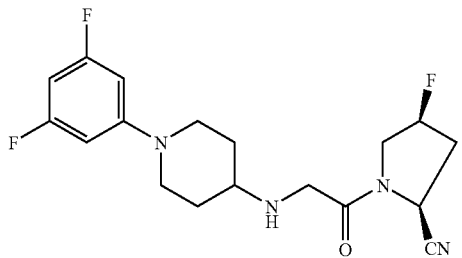

(2S,4S)-1-({[1-(3,5-Difluorophenyl)piperidin-4-yl]amino}acetyl)-4-fluoropyrrolidine-2-carbonitrile hydrochloride A. Tert-butyl 1-(3,5-difluorophenyl)piperidin-4-ylcarbamate A DMSO (25 mL, 0.1M) solution containing 4-N—BOC-aminopiperidine (500 mg, 2.5 mmol, 1.0 eq), 1,3,5-trifluorobenzene (256 µL, 2.5 mmol, 1.0 eq), and potassium carbonate (691 mg, 5.0 mmol, 2.0 eq) was heated to 100° C. for 18 h. The resulting mixture was cooled to RT, poured in H$_2$O (ca 50 mL), and extracted (3×) with EtOAc. The combined extracts were washed (2×) with H$_2$O, dried over MgSO$_4$, and concentrated in vocuo. The resulting solid was purified via flash chromatography using 1:1 Hexane/EtOAc as the mobile phase. Isolated 572 mg (1.83 mmol, 73% yield).

$^1$H NMR (CDC$_3$) 400 MHz δ 6.36 (d, 2H, J=8.8 Hz), 6.24 (t, 1H, J=9.0 Hz), 4.45 (s(br), 1H), 3.68–3.58 (m, 3H), 2.91 (t, 2H, J=13.2 Hz), 2.04 (d, 2H, J=13.0 Hz), 1.52–1.42 (m, 11H) ppm.

B. 1-(3,5-Difluorophenyl)piperidin-4-amine.

To a CH$_2$Cl$_2$ (40 mL) solution containing trifluoroacetic acid (4 mL) was added compound A (572 mg, 1.83 mmol, 1.0 eq). The resulting pale yellow solution was stirred at RT for 18 h at which time the solvent was removed in vacuo. The resulting TFA salt was used in the next step without further purification. Isolated 597 mg (1.83 mmol, 100% yield) of an amber semi-solid.

$^1$H NMR (d$_6$-DMSO) 400 MHz δ 7.80 (s(br), 2H), 6.63 (d, 2H, J=9.4 Hz), 6.46 (t, 1H, J=9.2 Hz), 3.83 (d, 2H, J=13.3 Hz), 3.23 (m, 1H), 2.87 (t, 2H, J=13.8 Hz), 1.8 (d, 2H, J=12.2 Hz), 1.52–1.46 (m, 2H) ppm.

C. (2S,4S)-1-({[1-(3,5-Difluorophenyl)piperidin-4-yl]amino}acetyl)-4-fluoropyrrolidine-2-carbonitrile.

(2S,4S)-1-(Bromoacetyl)-4-fluoropyrrolidine-2-carbonitrile (described earlier) (280 mg, 1.19 mmol, 1.0 eq) and compound B (429 mg, 1.31 mmol, 1.1 eq) were taken up in CH$_3$CN (20 mL). N,N-diisopropylethylamine (435 µL, 2.5 mmol, 2.1 eq) was then added and the resulting mixture stirred at RT overnight. The reaction was quenched with 1.0 M NaOH (ca 5 mL) and then poured into H$_2$O. The organics were extracted with EtOAc (3×), combined and dried over Na$_2$SO$_4$. The solvent was concentrated in vacuo and then the residue purified via flash chromatography using an initial mobile phase of 1% MeOH (with 0.1% NH$_3$) in CH$_2$Cl$_2$ then ramping to 2% MeOH (with 0.1% NH$_3$) in CH$_2$Cl$_2$ affording 174 mg (0.475 mmol, 40% yield) of a tan fluffy solid. To form the HCl salt, the free base was taken up in Et$_2$O and acetone added until all solids were in solution. 2.0 M HCl in ether was added dropwise until no more precipitate formed. The precipitate was then filtered and washed several times with Et$_2$O. The resulting salt was dried under high vacuum.

$^1$H NMR (D$_2$O) 400 MHz δ 6.59 (d, 2H, J=8.2 Hz), 6.43 (t, 1H, J=9.2 Hz), 5.48 (d, 1H, J=50.8 Hz), 4.93 (d, 1H, J=9.3 Hz), 4.10 (Abq, 2H, J=46.3, 16.3 Hz), 3.86 (m, 1H), 3.73–3.59 (m, 3H), 3.38 (m, 1H), 2.85 (t, 2H, J=13.5 Hz), 2.63 (t, 1H, J=15.8 Hz), 2.38 (m, 1H), 2.12 (d, 2H, J=13.4 Hz), 1.72–1.63 (m, 2H) ppm.

Example 12

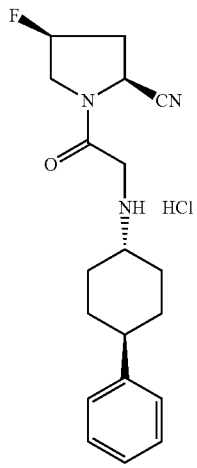

(2S,4S)-4-Fluoro-1-{[(4-phenylcyclohexyl)amino]acetyl}pyrrolidine-2-carbonitrile hydrochloride A. [(4-Phenylcyclohexyl)amino]acetic acid.

To a MeOH solution (130 mL) containing glycine (5.0 g, 66.6 mmol) and 4-phenylcyclohexanone (12.76 g, 73.3 mmol) was added NaCNBH$_3$ (3.34 g, 53.1 mmol). After stirring for 12 hrs the white slurry was collected via vacuum filtration and washed with MeOH. The precipitate was dried on the high vacuum line to yield 10.4 g (44.5 mmol, 66% yield) of the product A as a pure white solid.

$^1$H NMR (d$_6$-DMSO) 400 MHz δ 7.29–7.08 (m, 5H), 3.17 (s, 1H), 2.85 (s, 2H), 2.46–2.35 (m, 1H), 2.35–2.23 (m, 1H), 1.87 (d, 2H, J=14.6 Hz), 1.73 (d, 2H, J=11.5 Hz), 1.48–1.30 (m, 2H), 1.21–1.00 (m, 2H) ppm.

B. [(Tert-butoxycarbonyl)(4-phenylcyclohexyl)amino]acetic acid.

To a (1:1) dioxane/H$_2$O solution (12 mL) containing compound A (0.5 g, 2.14 mmol) and NaOH (0.21 g, 5.35 mmol) was added di-tert-butyldicarbonate(1.17 g, 5.35 mmol). After stirring for 12 hr the pH of the solution was reduced to 3 with 1.0 M HCl. The organics were extracted with EtOAc (3×) and the combined organics washed with H$_2$O (3×). After drying over MgSO$_4$ the solvents were reduced in vacuo to yield 312 mg (0.94 mmol, 44% yield) of the product B as a pure white solid.

$^1$H NMR (d$_4$-MeOH) 400 MHz δ 7.31–7.06 (m, 5H), 4.16–3.98 (m, 1H), 3.98–3.88 (m, 2H), 2.57–2.43 (m, 1H), 1.98–1.81 (m, 4H), 1.73–1.34 (m, 13H) ppm.

C. Tert-butyl 2-[(2S,4S)-2-cyano-4-fluoropyrrolidin-1-yl]-2-oxoethyl(4-phenylcyclohexyl)carbamate.

To a DMF solution (2 mL) containing compound B (0.2 g, 0.60 mmol) was added diisopropylethylamine (70 mg, 0.60 mmol) and HATU (0.23 g, 0.60 mmol). After stirring at RT for 1 hr a DMF solution (2 mL) containing (2S,4S)-4fluoro-2-pyrrolidinecarbonitrile 4-methylbenzenesulfonate (0.16 g, 0.544 mmol) and diisopropylethyl amine (70 mg, 0.60 mmol) was added. The reaction stirred for 12 hr after which it was poured into H$_2$O and the organics extracted with EtOAc (3×). The combined organics were washed with NaHCO$_3$, dried over MgSO$_4$ and the solvent reduced in vacuo. The product was purified via column chromatography (CH$_2$Cl$_2$/MeOH (19:1)) yielding 0.14 g (0.34 mmol, 63% yield) of the product C as a white solid.

$^1$H NMR (d$_4$-MeOH) 400 MHz δ 7.28–7.09 (m, 5H), 5.52 (d, 1H, J=51.7 Hz), 4.97 (d, 1H, J=8.8 Hz), 4.20–3.71 (m, 6H), 2.74–2.31 (m, 4H), 2.02–1.81 (m, 4H), 1.71–1.35 (m, 13H) ppm.

D. (2S,4S)-4-Fluoro-1-{[(4-phenylcyclohexyl)amino]acetyl}pyrrolidine-2-carbonitrile hydrochloride.

To a dioxane solution (3 mL) containing compound C (50 mg, 0.12 mmol) was added 4.0 M HCl in dioxane (0.3 mL, 1.12 mmol). After stirring for 1 hr the solvents were reduced in vacuo and the solution triterated with Et$_2$O. A white precipitate crashed out which was collected by vacuum filtration and dried on the high vacuum pump yielding 32 mg (0.09 mmol, 76% yield) of the product D as a pale yellow solid.

$^1$H NMR (d$_4$-MeOH) 400 MHz δ 7.36–7.10 (m, 5H), 5.58 (d, 1H, J=51.5 Hz), 5.06 (d, 1H, J=9.5 Hz), 4.37–3.65 (m, 5H), 3.30–3.20 (m, 1H), 2.73–2.41 (m, 3H), 2.35–2.20 (m, 2H), 2.14–1.93 (m, 2H), 1.76–1.49 (m, 3H) ppm.

Example 13

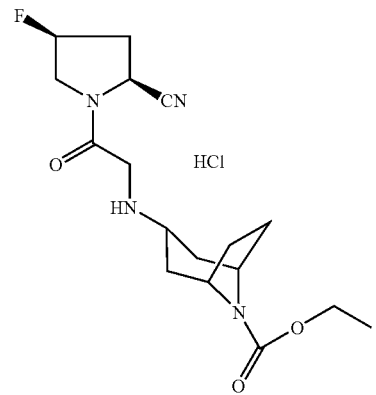

Ethyl 3-({2-[(2S,4S)-2-cyano-4-fluoropyrrolidin-1-yl]-2-oxoethyl}amino)-8-azabicyclo[3.2.1]octane-8-carboxylate hydrochloride A. N-[8-(Ethoxycarbonyl)-8-azabicyclo[3.2.1]oct-3-yl]glycine.

A MeOH solution (310 mL) containing glycine (10.0 g, 133.2 mmoL) and ethyl 3-oxo-8-azabicyclo[3.2.1]-8-carboxylate (28.9 g, 146.5 mmoL) had sodium cyanoborohydride (6.70 g, 106.6 mmoL) added to it. After 2 days the bulk of the MeOH was removed in vacuo and the beige tacky oil triterated repeatedly with ether to yield an extremely hydroscopic tan solid that was taken on crude.

$^1$H NMR (d$_4$-MeOH) 400 MHz δ 4.31 (s(br), 1H), 4.21 (s(br), 1H), 4.17–4.05 (m, 2H), 3.22 (s, 2H), 2.95–2.87 (m, 1H), 2.20–2.04 (m, 2H), 2.04–1.88 (m, 3H), 1.79–1.54 (m, 3H), 1.30–1.19 (m, 3H) ppm.

B. {(Tert-butoxycarbonyl)[8-(ethoxycarbonyl)-8-azabicyclo[3.2.1]oct-3-yl]amino}acetic acid.

To a (1:1) dioxane/H$_2$O solution (15 mL) containing compound A (2.0 g, 7.80 mmol) and NaOH (0.78 g, 19.5 mmol) was added di-tert-butyldicarbonate (4.23 g, 19.5 mmol). After stirring for 12 hr the pH of the solution was reduced to 3 with 1.0 M HCl. The organics were extracted with EtOAc (3×) and the combined organics washed with H$_2$O (3×). After drying over MgSO$_4$ the solvent was reduced in vacuo to yield 1.93 g (5.41 mmol, 70% yield) of the product B as a tan solid.

$^1$H NMR (d$_4$-MeOH) 400 MHz δ 4.29 (s(br), 2H), 4.20–4.07 (m, 2H), 3.89–3.63 (m, 3H), 2.34 (s(br), 1H), 1.98 (s(br), 2H), 1.86–1.62 (m, 3H), 1.53–1.32 (m, 11H), 1.21–1.21 (m, 3H) ppm.

C. Ethyl 3-((Tert-butoxycarbonyl){2-[(2S,4S)-2-cyano-4-fluoropyrrolidin-1-yl]-2-oxoethy}amino)-8-azabicyclo[3.2.1]octane-8-carboxylate.

To a DMF solution (7 mL) containing compound B (0.68 g, 1.92 mmol) was added diisopropylethyl amine (0.25 g, 1.92 mmol) and HATU (0.73 g, 1.92 mmol). After stirring at RT for 30 min a DMF solution (3 mL) containing (2S,4S)-4-fluoro-2-pyrrolidinecarbonitrile 4-methylbenzenesulfonate (0.5 g, 1.75 mmol) and diisopropylethyl amine (0.25 g, 1.92 mmol) was added. The reaction stirred for 12 hr after which it was poured into H$_2$O and the organics extracted with EtOAc (3×). The combined organics were washed with NaHCO₃, dried over MgSO₄ and the solvent reduced in vocuo. The brown oil was purified via column chromatography (CH₂Cl₂/MeOH (9:1)) yielding 0.35 g (0.77 mmol, 43% yield) of the product C as a white tacky solid.

¹H NMR (d₄-MeOH) 400 MHz δ 5.51 (d, 1H, J=51.3 Hz), 4.96 (d, 1H, J=9.5 Hz), 4.30 (s(br), 2H), 4.24–3.62 (m, 7H), 2.80 (s, 2H), 2.73–2.25 (m, 4H), 2.07–1.88 (m, 2H), 1.88–1.58 (m, 2H), 1.54–1.33 (m, 9H), 1.33–1.17 (m, 3H) ppm.

D. Ethyl 3-({2-[(2S,4S)-2-cyano-4-fluoropyrrolidin-1-yl]-2-oxoethyl}amino)-8-azabicyclo[3.2.1]octane-8-carboxylate hydrochloride.

To a dioxane solution (2 mL) containing compound C (0.35 g, 0.77 mmol) was added 4.0 M HCl in dioxane (2 mL, 7.7 mmol). After stirring for 1 hr the solvents were reduced in vacuo and the solution triturated with Et₂O. A white precipitate crashed out which was collected by vacuum filtration and dried on the high vacuum pump yielding 50 mg (0.13 mmol, 17% yield) of the product D as a pale yellow solid.

¹H NMR (d₄-MeOH) 400 MHz δ 5.54 (d, 1H, J=52 Hz), 5.04 (d, 1H, J=9 Hz), 4.39 (s(br), 2H), 4.25–3.69 (m, 6H), 3.27–3.13 (m, 1H), 2.71–2.37 (m, 4H), 2.12–2.03 (m, 2H), 1.86–1.76 (m, 2H), 1.70–1.54 (m, 2H), 1.26 (t, 3H, J=7.2 Hz) ppm.

Example 14

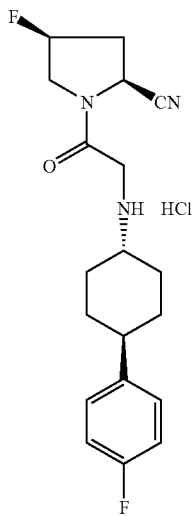

(2S,4S)-4-Fluoro-1-({[4-(4-fluorophenyl)cyclohexyl]amino}acetyl)pyrrolidine-2-carbonitrile hydrochloride A. {[4-(4-Fluorophenyl)cyclohexyl]amino}acetic acid.

To a MeOH solution (5 mL) containing glycine (0.18 g, 2.37 mmol) and 4(4-fluorophenyl)cyclohexanone (see *J. Med. Chem.*, 15, 1235 (1972); Lednicer, D. et al. for preparation of this compound) (0.5 g, 2.6 mmol) was added NaCNBH₃ (0.12 g, 1.89 mmol). After stirring for 12 hrs the solvents were reduced in vacuo and the residue triterated with Et₂O and hexanes resulting in the precipitation of a white solid which was collected via vacuum filtration. The solid was purified via column chromatography (CH₂Cl₂/MeOH (19:1)) yielding 0.45 g (1.79 mmol, 76% yield) of the product A as a 3:1 mixture of diastereomers.

¹H NMR (d₄-MeOH) 400 MHz δ 7.38–7.27 (m, 2H minor), 7.27–7.18 (m, 2H major), 7.08–6.93 (m, 4H major+minor), 3.52 (s, 4H major+minor), 3.45–3.35 (m, 1H minor), 3.23–3.06 (m, 1H major), 2.83–2.71 (m, 1H minor), 2.64–2.51 (m, 1H major), 2.29–2.14 (m, 2H major), 2.07–1.76 (m, 8H major+minor), 1.66–1.48 (m, 6H major+minor) ppm.

B. {(Tert-butoxycarbonyl)[4-(4-fluorophenyl)cyclohexyl]amino}acetic acid.

To a (3:2) dioxane/H₂O solution (5 mL) containing a 3:1 diastereomeric mixture of compound A (0.45 g, 1.79 mmol) and NaOH (0.18 g, 4.48 mmol) was added di-tert-butyidicarbonate (0.98 g, 4.48 mmol). After stirring for 12 hrs the pH of the solution was reduced to 3 with 1.0 M HCl. The organics were extracted with EtOAc (3×) and the combined organics washed with H₂O (3×). After drying over MgSO₄ the solvents were reduced in vacuo to yield 0.27 g (0.77 mmol, 43% yield) of product B as a 3:1 mixture of diastereomers.

¹H NMR (d₄-MeOH) 400 MHz δ 7.4–7.34 (m, 2H minor), 7.26–7.18 (m, 2H major), 7.07–6.93 (m, 4H major+minor), 4.10–4.00 (m, 1H major), 3.92 (s, 2H minor), 3.86 (s, 2H major), 3.68–3.65 (m, 1H minor), 3.00–2.97 (m, 1H minor), 2.55–2.44 (m, 1H major), 2.32–2.23 (m, 2H minor), 1.97–1.82 (m, 6H major+minor), 1.68–1.51 (m, 8H major+minor), 1.51–1.38 (m, 18H major+minor) ppm.

C. Tert-butyl 2-[(2S,4S)-2-cyano-4-fluoropyrrolidin-1-yl]-2-oxoethyl[4-(4-fluorophenyl)cyclohexyl]carbamate.

To a CH₂Cl₂ solution (3 mL) containing a 3:1 mixture of compound B (0.27 g, 0.76 mmol) was added HOBT (0.16 g, 1.15 mmol) and EDC (0.16 g, 0.85 mmol). After stirring at RT for 30 min a CH₂Cl₂solution (2 mL) containing (2S,4S)-4fluoro-2-pyrrolidinecarbonitrile4-methylbenzenesulfonate 0(.24 g, 0.85 mmol) and diisopropylethyl amine (0.11 g, 0.85 mmol) were added. The reaction stirred for 12 hrs after which it was poured into H₂O and the organics extracted with EtOAc (3×). The combined organics were washed with NaHCO₃, dried over MgSO₄ and the solvent reduced in vacuo. The colorless oil was recrystallized from Et₂O yielding 145 mg of the product which underwent further purification via semi-prep HPLC yielding 90 mg (0.20 mmol, 26% yield) of the trans product C.

¹H NMR (d₄-MeOH) 400 MHz δ 7.26–7.16 (m, 2H), 7.02–6.91 (m, 2H), 5.53 (d, 1H, J=52 Hz), 4.98 (d, 1H, J=9.3 Hz), 4.19–3.71 (m, 5H), 2.30–2.72 (m, 3H), 2.03–1.80 (M, 4H), 1.69–1.51 (m, 4H), 1.51–1.35 (m, 9H) ppm.

D. (2S,4S)-4-Fluoro-1-({[4-(4-fluorophenyl)cyclohexyl]amino}acetyl)pyrrolidine-2-carbonitrile hydrochloride.

To a dioxane solution (1 mL) containing compound C (0.09 g, 0.20 mmol) was added 4.0 M HCl in dioxane (0.5 mL, 1.98 mmol) and 2.0 M HCl in Et₂O (0.5 mL, 0.99 mmol. After stirring for 1 hr the solvents were reduced in vacuo and the solution triterated with Et₂O. A white precipitate crashed out which was collected by vacuum filtration and dried on the high vacuum pump yielding 15 mg (.039 mmol, 20% yield) of the product D as a white solid.

¹H NMR (d₄-MeOH) 400 MHz δ 7.26–7.20 (m, 2H), 7.04–6.97 (m, 2H), 5.55 (d, 1H, J=52 Hz), 5.06 (d, 1H, J=9.3 Hz), 4.25–3.73 (m, 5H), 3.24 (s(br), 1H), 2.72–2.40 (m, 3H), 2.27 (s(br), 2H), 2.62 (s(br), 2H), 1.67–1.55 (m, 4H) ppm.

Example 15

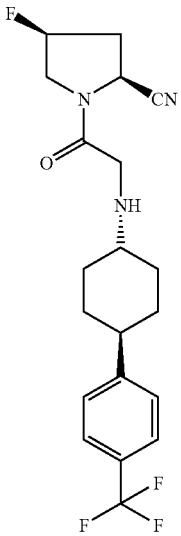

(2S,4S)-4-Fluoro-1-[({4-[4-(trifluoromethyl)phenyl] cyclohexyl}amino)acetyl]pyrrolidine -2-carbonitrile hydrochloride A. ({4-[4-(Trifluoromethyl)phenyl]cyclohexyl}amino)acetic acid.

To a MeOH solution (10 mL) containing glycine (0.2 g, 2.75 mmol) and 4-trifluoromethyl phenylcyclohexanone (see *J. Med. Chem.*, 15, 1235 (1972); Lednicer, D. et al. for preparation of this compound) (1.0 g, 3.99 mmol) was added NaCNBH₃ (0.13 g, 2.2 mmol). After stirring for 12 hrs the white precipitate was collected via vacuum filtration and washed with MeOH. The solid was dried on the high vacuum line to yield 0.4 g (1.32 mmol, 50% yield) of the product A as a white solid.

¹H NMR (d₄-MeOH) 400 MHz δ 7.59 (d, 2H, J=8.3 Hz), 7.44 (d, 2H, J=8.1 Hz), 3.52 (s, 2H), 3.23–3.15 (m, 1H), 2.7–2.64 (m, 1H), 2.25 (d, 2H, J=10.7 Hz), 2.03 (d, 2H, J=12 Hz), 1.69–1.53 (m, 4H) ppm.

B. (Tert-butoxycarbonyl){-[4-(trifluoromethyl)phenyl] cyclohexyl}amino)acetic acid.

To a (1:1) dioxane/H₂O solution (10 mL) containing compound A (0.37 g, 1.22 mmol) and NaOH (60 mg, 1.46 mmol) was added di-tert-butyldicarbonate (0.32 g, 1.46 mmol). After stirring for 12 hrs the pH of the solution was reduced to 3 with 1.0 M HCl. The organics were extracted with EtOAc (3×) and the combined organics washed with H₂O (3×). After drying over MgSO₄ the solvents were reduced in vacuo to yield 0.49 g (1.21 mmol, 55% yield) of the product B as a pure white solid.

¹H NMR (d₄-MeOH) 400 MHz δ 7.57 (d, 2H, J=8.3 Hz), 7.43 (d, 2H, J=8.2 Hz), 4.12–4.04 (m, 1H), 3.87 (s, 2H), 2.63–2.58 (m, 1H), 2.00–1.87 (m, 4H), 1.7–1.55 (m, 4H), 1.43 (s, 9H) ppm.

C. Tert-butyl 2-[(2S,4S)-2-cyano-4-fluoropyrrolidin-1-yl]-2-oxoethyl{4-[4-(trifluoromethyl)phenyl] cyclohexyl}carbamate.

To a THF solution (3 mL) containing compound B (0.27 g, 0.67 mmol) was added diisopropylethylamine (0.10 g, 0.74 mmol) and HATU (0.28 g, 0.74 mmol). After stirring at RT for 1 hr a THF solution (2 mL) containing (2S,4S)-4-fluoro-2-pyrrolidinecarbonitrile 4-methylbenzenesulfonate (0.21 g, 0.74 mmol) and diisopropylethyl amine (0.10 g, 0.74 mmol) was added. The reaction stirred for 12 hrs after which it was poured into H₂O and the organics extracted with EtOAc (3×). The combined organics were washed with NaHCO₃, dried over MgSO₄ and the solvent reduced in vacuo. The product was purified via column chromatography (CH₂Cl₂/MeOH (19:1)) yielding 0.13 g (0.26 mmol, 41% yield) of product C as a white solid.

¹H NMR (d₄-MeOH) 400 MHz δ 7.57 (d, 2H, J=8.3 Hz), 7.42 (d, 2H, J=8.3 Hz), 5.53 (d, 1H, J=51.7 Hz), 4.98 (d, 1H, J=9.5 Hz), 4.21–3.62 (m, 5H), 2.73–2.33 (m, 3H), 2.06–1.84 (m, 4H), 1.75–1.53 (m, 4H), 1.49–1.43 (m, 9H) ppm.

D. (2S,4S)-4-Fluoro-1-[({[4-(trifluoromethyl)phenyl] cyclohexyl}amino)acetyl]pyrrolidine-2-carbonitrile hydrochloride.

To a dioxane solution (1 mL) containing compound C (0.13 g, 0.26 mmol) was added 4.0 M HCl in dioxane (0.78 mL, 3.12 mmol) and 2.0 M HCl in Et₂O (0.78 mL, 1.56 mmol). After stirring for 1 hr the solvents were reduced in vocuo and the solution triterated with Et₂O. A white precipitate crashed out which was collected by vacuum filtration and dried on the high vacuum pump. The product was purified via semi-prep HPLC yielding 48 mg (0.11 mmol, 42% yield) of the product D as a white solid.

¹H NMR (d₄-MeOH) 400 MHz δ 7.60 (d, 2H, J=8.1 Hz), 7.44 (d, 2H, J=7.9 Hz), 5.56 (d, 1H, J=51.2 Hz), 5.06 (d, 1H, J=9.3 Hz), 4.29–3.71 (m, 5H), 2.76–2.41 (m, 3H), 2.37–2.23 (m, 2H), 2.10–2.0 (m, 2H), 1.73–1.58 (m, 4H) ppm.

Examples 16 and 17

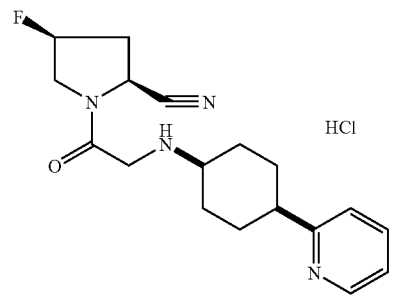

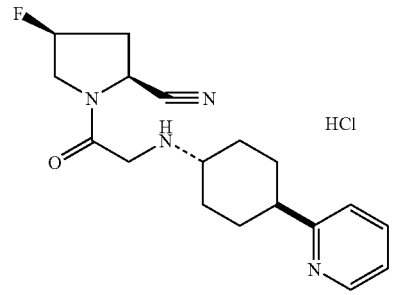

(2S,4S)-4-Fluoro-1-{[(4-pyridin-2-ylcyclohexyl)amino]acetyl}pyrrolidine-2-carbonitrile hydrochloride (cis et trans, respectively)

A. 8-Pyridin-2-yl-1,4-dioxaspiro[4.5]decan-8-ol.

To a $Et_2O$ solution (70 mL) containing 2-bromopyridine (7.62 g, 48.2 mmoL) cooled to −78° C. was added 18.3 mL of a 2.7 M heptane solution of n-BuLi (49.7 mmoL). The resulting dark solution stirred for 15 min at −78° C. when 1,4-cyclohexanedione monoethylene ketal (7.16 g, 45.8 mmoL) in 40 mL of THF was added. The solution stirred for 1 hr at −78° C. and was then quenched with $H_2O$. Upon warming the solution was poured into additional $H_2O$ and the organics were extracted with EtOAc. After drying over $MgSO_4$ the solvent was removed in vacuo and the residual dark oil was purified via column chromatography (hexanes/EtOAc (3:2)) yielding 4.51 g (20.2 mmoL, 44% yield) of compound A.

$^1$H NMR ($CDCl_3$) 400 MHz δ 8.50 (d, 1H, J=4.7 Hz), 7.68 (t, 1H, J=7.7 Hz), 7.39 (d, 1H, J=8.0 Hz), 7.18 (m, 1H), 5.19 (s, 1H), 4.02–3.96 (m, 4H), 2.22–2.05 (m, 4H), 1.73–1.67 (m, 4H) ppm.

B. 2-(1,4-Dioxaspiro[4.5]dec-7-en-8-yl)pyridine.

To a pyridine solution (50 mL) containing compound A (5.69 g, 25.5 mL) cooled to 0° C. was added thionyl chloride (15.2 g, 127.6 mmoL) dropwise. The resulting solution stirred for 2 hr at 0° C. and was then poured onto crushed ice. The organics were extracted with $CH_2Cl_2$ and the aqueous layer made basic with 2.0 M NaOH and extracted again with $CH_2Cl_2$. The combined organic layers were dried ($MgSO_4$) and the solvent removed in vacuo yielding 4.86 g (23.7 mmoL, 93% yield) of compound B as an orange oil which was taken on crude.

$^1$H NMR ($CDCl_3$), 400 MHz δ 8.53 (d, 1H, J=4.6 Hz), 7.61 (t, 1H, J=7.7 Hz), 7.38 (d, 1H, J=8.0 Hz), 7.10 (m, 1H), 6.57 (s(br), 1H), 4.01 (s, 4H), 2.80–2.76 (m, 2H), 2.51 (s(br), 2H), 1.93 (t, 2H, J=6.5 Hz) ppm.

C. 2-(1,4-Dioxaspiro[4.5]dec-8-yl)pyridine.

A 2-neck flask containing compound B (4.86 g, 23.7 mmoL) and 610 mg of 10% Pd/C in 60 mL of EtOAc was evacuated three times under vacuum followed by filling with hydrogen via balloon (3×). After stirring under a balloon of hydrogen for 5 hr. The solution was filtered through a bed of celite with the celite being rinsed thoroughly with $CH_2Cl_2$. The solvent was removed in vacuo and the crude material resubjected to the reaction conditions yielding 4.11 g (19.8 mmoL, 84% yield) of compound C as a yellow oil which was taken on crude.

$^1$H NMR ($CDCl_3$) 400 MHz δ 8.53 (d, 1H, J=4.5 Hz), 7.71 (t, 1H, J=7.7 Hz), 7.25 (d, 1H, J=2.9 Hz), 7.19 (m, 1H), 3.96 (s, 4H), 2.90 (m, 1H), 2.01–1.97 (m, 2H), 1.86–1.80 (m, 4H), 1.74–1.67 (m, 2H) ppm.

D. 4-Pyridin-2-ylcyclohexanone.

To a flask containing compound C (4.10 g, 19.8 mmoL) cooled to 0° C. was added 30 mL of TFA followed by 2 mL of $H_2O$. After 2.5 hr the solution was carefully poured into sat. $NaHCO_3$. The organics were extracted with $CH_2Cl_2$ (2×) and then the aqueous layer made basic with 2.0 M NaOH. After extracting with $CH_2Cl_2$ the combined organic layers were dried ($MgSO_4$) and the solvent removed in vacuo. The residual yellow solid was purified via column chromatography (hexanes/EtOAc (1:1)) yielding 2.58 g (14.7 mmoL, 74% yield) of compound D.

$^1$H NMR ($CDCl_3$) 400 MHz δ 8.53 (d, 1H, J=4.6 Hz), 7.61 (m, 1H), 7.18 (d, 1H, J=7.8 Hz), 7.13 (m, 1H), 3.18 (m, 1H), 2.52–2.48 (m, 4H), 2.31–2.27 (m, 2H), 2.11–2.03 (m, 2H) ppm.

E. [(4-Pyridin-2-ylcyclohexyl)amino]acetic acid.

To a MeOH solution (10 mL) containing glycine (0.19 g, 2.59 mmol) and compound D (0.5 g, 2.78 mmol) was added $NaCNBH_3$ (0.13 g, 2.02 mmol). After stirring for 12 hrs the white precipitate was collected via vacuum filtration and washed with MeOH. The precipitate was dried on the high vacuum line to yield 0.12 g (0.51 mmol, 47% yield) of the product E as a 3:2 mixture of diastereomers.

$^1$H NMR ($d_4$-MeOH) 400 MHz δ 8.45 (d, 2H major+minor, J=4.7 Hz), 7.90–7.40 (m, 2H major+minor), 7.34 (d, 2H major+minor, J=7.8 Hz), 7.27–7.24 (m, 2H major+minor), 3.52 (s, 4H major+minor), 3.20–3.14 (m, 2H major+minor), 2.78–2.70 (m, 2H major+minor), 2.62 (d, 4H major+minor, J=11.8 Hz), 2.08 (d, 4H major+minor, J=12.6 Hz), 1.75–1.53 (m, 8H major+minor) ppm.

F. [(Tert-butoxycarbonyl)(4-pyridin-2-ylcyclohexyl)amino]acetic acid.

To a (1:1) dioxane/$H_2O$ solution (10 mL) containing compound E as a 3:2 mixture of diastereomers (0.5 g, 2.13 mmol) and NaOH (0.17 g, 4.26 mmol) was added di-tert-butyldicarbonate (0.93 g, 4.26 mmol). After stirring for 12 hrs the pH of the solution was reduced to 3 with 1.0 M HCl. The organics were extracted with EtOAc (3×) and the combined organics washed with $H_2O$ (3×). After drying over $MgSO_4$ the solvents were reduced in vacuo to yield 0.46 g (1.37 mmol, 65% yield) of the product F as a 3:2 mixture of diastereomers.

$^1$H NMR ($d_4$-MeOH) 400 MHz δ 8.51 (d, 1H minor, J=3.9 Hz), 8.43 (d, 1H major, J=4.8 Hz), 7.85–7.74 (m, 2H major+minor), 7.50 (d, 1H major, J=8 Hz), 7.40–7.34 (m, 1H minor), 7.31–7.21 (m, 2H), 4.13–4.01 (m, 1H major), 3.95–3.82 (m, 4H major+minor), 3.8 (s, 1H minor), 3.09 (s, 1H minor), 2.76–2.64 (m, 1H major), 2.43–2.40 (m, 2H minor), 2.07–1.81 (m, 6H major+minor), 1.81–1.52 (m, 8H), 1.52–1.37 (m, 18H major+minor) ppm.

G. Tert-butyl 2-[(2S,4S)-2-cyano-4-fluoropyrrolidin-1-yl]-2-oxoethyl(4-pyridin-2-ylcyclohexy)carbamate.

To a THF solution (6 mL) containing compound F as a 3:2 mixture of diastereomers (0.46 g, 1.37 mmol) was added diisopropylethylamine (0.2 g, 1.37 mmol) and HATU (0.57 g, 1.37 mmol). After stirring at RT for 1 hr a THF solution (2 mL) containing (2S,4S)-4-fluoro-2-pyrrolidinecarbonitrile 4-methylbenzenesulfonate (0.43 g, 1.37 mmol) and diisopropylethyl amine (0.2 g, 1.37 mmol) was added. The reaction stirred for 12 hrs after which it was poured into $H_2O$ and the organics extracted with EtOAc (3×). The combined organics were washed with $NaHCO_3$, dried over $MgSO_4$ and the solvents reduced in vacuo. The product was purified via column chromatography ($CH_2Cl_2$/MeOH (19:1)) yielding 0.48 g (1.12 mmol, 80% yield) of the isomeric product as a white solid which underwent further purification via semi-prep HPLC yielding diastereomer 1 (trans) (0.18 g, 0.4 mmol) and diastereomer 2 (cis) (0.15 g, 0.32 mmol).

Diastereomer 1: $^1$H NMR ($d_4$-MeOH) 400 MHz δ 8.48 (d, 1H, J=6.7 Hz), 7.76 (t, 1H, J=8.1 Hz), 7.46 (d, 1H, J=6.1 Hz), 7.22–7.15 (m, 1H), 5.47 (d, 1H, J=51.3 Hz), 4.92 (d, 1H, J=9.4 Hz), 4.01–3.58 (m, 4H), 3.26–3.17 (m, 1H), 3.07 (s, 1H), 2.65–2.29 (m, 4H), 1.98–1.83 (m, 2H), 1.76–1.48 (m, 4H), 1.43–1.32 (m, 9H) ppm.

Diastereomer 2: $^1$H NMR ($d_4$-MeOH) 400 MHz δ 8.42 (d, 1H, J=5.9 Hz), 7.78 (t, 1H, J=9.1 Hz), 7.34 (d, 1H, J=7.8

Hz), 7.26–7.19 (m, 1H), 5.53 (d, 1H, J=51.3 Hz), 4.98 (d, 1H, J=9.3 Hz), 4.26–3.62 (m, 5H), 2.75–2.34 (m, 3H), 2.06–1.85 (m, 4H), 1.79–1.54 (m, 4H), 1.54–1.32 (m, 9H) ppm.

H. (2S,4S)-4-Fluoro-1-{[(4-pyridin-2-ylcyclohexyl)amino]acetyl}pyrrolidine-2-carbonitrile hydrochloride (trans).

To a Et$_2$O solution (2 mL) containing compound G (diastereomer 1) (0.18 g, 0.35 mmol) was added 4.0 M HCl in dioxane (2.12 mL, 8.5 mmol). After stirring for 40 min the solvents were reduced in vacuo and the solution triturated with EtOAc. A white precipitate crashed out of solution which was then collected by vacuum filtration and dried on the high vacuum pump yielding 0.13 g (0.35 mmol, 100% yield) of the product H as a white solid.

$^1$H NMR (d$_4$-MeOH) 400 MHz δ 8.78 (d, 1H, J=6.1 Hz), 8.65 (t, 1H, J=7.9 H), 8.17 (d, 1H, J=8.1 Hz), 8.00 (t, 1H, J=7.4 Hz), 5.55 (d, 1H, J=51.2 Hz), 5.06 (d, 1H, J=9.4 Hz, 4.29–3.68 (m, 5H), 3.58 (s, 1H), 3.33–3.27 (m, 1H), 2.72–2.41 (m, 2H), 2.28–2.00 (m, 7H) ppm.

I. (2S,4S)-4-Fluoro-1-{[(4-pyridin-2-ylcyclohexyl)amino]acetyl}pyrrolidine-2-cabonitrile hydrochloride (cis).

To an Et$_2$O solution (2 mL) containing compound G (diastereomer 2) (0.15 g, 0.35 mmol) was added 4.0 M HCl in dioxane (1.80 mL, 7 mmol). After stirring for 40 min the solvent were reduced in vacuo and the solution triterated with EtOAc. A white precipitate crashed out of solution which was then collected by vacuum filtration and dried on the high vacuum pump yielding 30 mg (0.08 mmol, 21% yield) of the product I as a white solid.

$^1$H NMR (d$_4$-MeOH) 400 MHz δ 8.76 (d, 1H, J=5.9 Hz), 8.62–8.57 (m, 1H), 8.07 (d, 1H, J=8.1 Hz), 7.98 (t, 1H, J=6.9 Hz), 5.56 (d, 1H, J=51.4 Hz), 5.06 (d, 1H, J=9.2 Hz), 4.28–3.70 (m, 4H), 3.39–3.30 (m, 1H), 3.23–3.12 (m, 1H), 2.62–2.37 (m, 4H), 2.25 (d, 2H, J=12.9 Hz), 1.87–1.69 (m, 4H) ppm.

Example 18

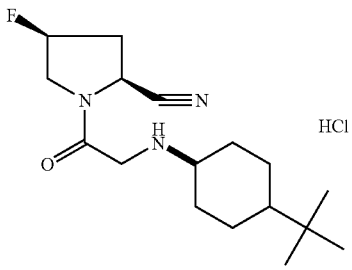

(2S,4S)-1-{[(4-Tert-butylcyclohexyl)amino]acetyl}-4-fluoropyrrolidine-2-carbonitrile hydrochloride A. [(4-Tert-butylcyclohexyl)amino]acetic acid.

To a MeOH solution (100 mL) containing glycine (5.0 g, 66.6 mmol) and 4-tert-butylcyclohexanone (11.30 g, 73.3 mmol) was added NaCNBH$_3$ (3.34 g, 53.3 mmol). After stirring for 12 hrs the white slurry was collected via vacuum filtration and washed with MeOH. The precipitate was dried on the high vacuum pump to yield 10.4 g (44.5 mmol, 66% yield) of the product A as a 3:1 mixture of diastereomers.

$^1$H NMR (d$_4$-MeOH) 400 MHz δ 3.47 (s, 2H minor), 3.46 (s, 2H major), 3.37 (s, 1H minor), 3.02–2.91 (m, 1H major), 2.18–2.03 (m, 4H major+minor), 1.96–1.88 (m, 2H major), 1.76–1.64 (m, 3H major+minor), 1.41–1.20 (m, 4H major+minor), 1.20–1.00 (m, 5H major+minor), 0.92–0.84 (m, 18H major+minor) ppm.

B. [(Tert-butoxycarbonyl)(4-tert-butylcyclohexyl)amino]acetic acid.

To a (1:1) dioxane H$_2$O solution (10 mL) containing compound A as a 3:1 mixture of diastereomers (1 g, 4.70 mmol) and NaOH (0.47 g, 11.78 mmol) was added di-tert-butyldicarbonate (2.56 g, 11.8 mmol). After stirring for 12 hrs the pH of the solution was reduced to 3 with 1.0 M HCl. The organics were extracted with EtOAc (3×) and the combined organics washed with H$_2$O (3×). After drying over MgSO$_4$ the solvents were reduced in vacuo to yield 1.28 g (4.08 mmol, 87% yield) of the product B as a 3:1 mixture of diastereomers.

$^1$H NMR (d$_4$-MeOH) 400 MHz δ 4.04–3.65 (m, 6H major+minor), 1.86–1.66 (m, 6H major+minor), 1.64–1.57 (m, 2H major+minor), 1.50–1.27 (m, 22H major+minor), 1.21–1.09 (m, 4H major+minor), 1.005–0.98 (m, 2H), 0.87–0.70 (m, 18H) ppm.

C. Tert-butyl 4-tert-butylcyclohexyl{2-[(2S,4S)-2-cyano-4-fluoropyrrolidin-1-yl]-2-oxoethyl}carbamate.

To a THF solution (2 mL) containing compound B as a 3:1 mixture of diastereomers (0.44 g, 1.41 mmol) was added diisopropylethylamine (0.2 g, 1.54 mmol) and HATU (0.59 g, 1.54 mmol). After stirring at RT for 1 hr a THF solution (1 mL) containing (2S,4S)-4-fluoro-2-pyrrolidinecarbonitrile 4-methylbenzenesulfonate (0.44 g, 1.54 mmol) and diisopropylethyl amine (0.2 g, 1.54 mmol) was-added. The reaction stirred for 12 hrs after which it was poured into H$_2$O and the organics extracted with EtOAc (3×). The combined organics were washed with NaHCO$_3$, dried over MgSO$_4$ and the solvent reduced in vacuo. The product was purified via column chromatography (CH$_2$Cl$_2$/MeOH (19:1)) and underwent further purification by semi-prep HPLC yielding 0.4 g (0.98 mmol, 70% yield) of the product C as a white solid.

$^1$H NMR (d$_4$-MeOH) 400 MHz δ 5.51 (d, 1H, J=51.5 Hz), 4.96 (d, 1H, J=9.3 Hz), 4.20–3.67 (m, 5H), 2.72–2.31 (m, 2H), 1.95–1.72 (m, 4H), 1.50–1.37 (m, 9H), 1.37–091 (m, 5H), 0.90–0.82 (m, 9H) ppm.

D. (2S,4S)-1-{[(4-Tert-butylcyclohexy)amino]acetyl}-4-fluoropyrrlidine-2-carbonitrile hydrochloride.

To a dioxane solution (1 mL) containing compound C (0.4 g, 0.98 mmol) was added 4.0 M HCl in dioxane (4.8 mL, 19.2 mmol). After stirring for 30 min the solvents were reduced in vacuo and the solution triturated with Et$_2$O. A white precipitate crashed out of solution which was then collected by vacuum filtration and dried on the high vacuum pump yielding 0.27 g (0.77 mmol, 79% yield) of the product D as a white solid.

$^1$H NMR (d$_4$-MeOH) 400 MHz δ 5.54 (d, 1H, J=51.3 Hz), 5.04 (d, 1H, J=9.5 Hz), 4.32–3.70 (m, 4H), 3.13–2.99 (m, 1H), 2.73–2.37 (m, 2H), 2.21 (d, 2H, J=12.7 Hz), 1.97 (d, 2H, J=13.1 Hz), 1.46–1.30 (m, 2H), 1.21–1.03 (m, 3H), 0.93–0.85 (m, 9H) ppm.

Example 19

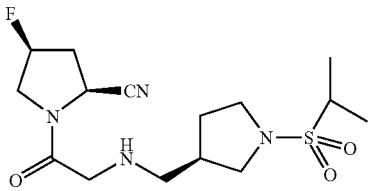

(2S,4S)-4-Fluoro-1-[({[(3R)-1-(isopropylsulfonyl)
pyrrolidinyl]methyl}amino)acetyl]-2-pyrrolidinecarbonitrile and hydrochloride A. [(3S)-1-(Isopropylsulfonyl)pyrrolidinyl]methyl2-propanesulfonate.

Potassium carbonate 1.6 g (11.6 mmol) was added to a stirred solution of 505 mg (5 mmol) (3S)-pyrrolidinylmethanol (J. Med. Chem. 1987, 30, 1711) and 1.42 g (10 mmol) i-propylsulfonyl chloride in 10 mL acetonitrile. The mixture was stirred at room temperature for 12 hours, then filtered. The filtrate was concentrated under reduced pressure and the residue was chromatographed on silica gel (hexanes-EtOAc 1:1) to obtain 740 mg (47% yield) of compound A.

$^1$H NMR (CDCl$_3$) 400 MHz δ 4.22 (dd, J=6.2, 10.2 Hz, 1H), 4.14 (dd, J=7.6, 10.2 Hz, 1H), 3.58 (dd, J=7.2, 10.2 Hz, 1H), 3.55 (m, 1H), 3.43 (m, 1H), 3.16–3.36 (m, 3H), 2.70 (m, 1H), 2.12 (m, 1H), 1.78 (m, 1H), 1.43 (d, J=6.9 Hz, 6H), 1.35 (dd, J=1.8, 6.9 Hz, 6H) ppm.

B. (3R)-3-(Azidomethyl)-1-(isopropylsulfonyl)pyrrolidine.

A mixture of 740 mg (2.35 mmol) of compound A, (1.49 g, 10 mmol) of sodium iodode and 0.65 g (10 mmol) of sodium azide in 5 mL DMF was stirred at 70° C. for 12 hours, then cooled to 20° C. Ethyl acetate (50 mL) was added to the reaction mixture and then the salts were filtered. Filtrate was concentrated under reduced pressure and the residue was purified by silica gel chromatography (hexanes-EtOAc 1:1) to obtain 467 mg of compound B (Yield: 85%).

$^1$H NMR (CDC$_3$) 400 MHz δ 3.56 (dd, J=7.1, 9.8 Hz, 1H), 3.52 (m, 1H), 3.30–3.45 (m, 3H), 3.22 (m, 1H), 3.16 (dd, J=1.7 Hz, 4.8 Hz, 1H), 2.49 (m, 1H), 2.08 (m, 1H), 1.75 (m, 1H), 1.35 (dd, J=2.1, 6.8 Hz, 6H) ppm.

C. [(3R)-1-(Isopropylsulfonyl)pyrrolidinyl]methanamine.

Compound B (467 mg, 2.0 mmol) dissolved in 10 mL of ethanol. palladium (250 mg 10% on activated carbon) was added to the solution and the mix was stirred for an hour under 1 atm hydrogen at 20° C. The mixture was filtered to remove the catalyst and the filtrate was concentrated under reduced pressure to obtain 389 mg of compound C (Yield: 94%).

$^1$H NMR (CDCl$_3$) 400 MHz δ 3.56 (dd, J=7.4, 9.6 Hz, 1H), 3.52 (m, 1H), 3.38 (m, 1H), 3.22 (m, 1H), 3.13 (dd, J=7.3, 9.7 Hz, 1H), 2.75 (m, 1H), 2.32 (m, 1H), 2.07 (m, 1H), 1.65 (m, 3H), 1.34 (dd, J=2.2, 6.9 Hz, 6H) ppm.

D. (2S,4S)-4-Fluoro-1-[({[(3R)-1-(isopropylsulfonyl)pyrrolidinyl]methyl}amino)acetyl]-2-pyrrolidinecarbonitrile.hydrochloride.

A solution of 1-N-bromoacetyl-(2S)-cyano-(4S)-fluoropyrrolidine (described earlier) (389 mg, 1.65 mmol) in 5 mL acetonitrile was added to a stirred solution of 389 mg (1.88 mmol) of compound C and N,N-diisopropyl-ethylamine (258 mg, 2 mmol) in 5 mL acetonitrile at 50° C. The mixture was stirred at 50° C. for two hours and then cooled to room temperature. The solvent was evaporated under reduced pressure. The residue was purified by silica gel chromatography (5% methanol in CH$_2$Cl$_2$) affording compound D. This compound was dissolved in CH$_2$Cl$_2$, acidified to pH ~1 with 2.0 M HCl in ether and then the solution concentrated under reduced pressure to obtain the hydrochloride salt of compound D as a white foam (350 mg, Yield: 53%).

$^1$H NMR (DMSO-d$_6$) 400 MHz δ 9.22 (s (broad), 2H), 5.51 (d, J=51.6, 1H), 5.04 (d, J=9.6 Hz, 1H), 4.20 (m, 1H), 3.95 (m, 2H), 3.70 (m, 1H), 3.55 (m, 2H), 3.35 (m, 2H), 3.08 (m, 3H), 3.00 (d, J=12 Hz, 1H), 2.60 (m, 1H), 2.06 (m, 1H), 1.70 (m, 1H), 1.22 (m, 6H) ppm.

E. (2S,4S)-4-Fluoro-1-[({[(3R)-1-(isopropylsulfonyl)pyrrolidinyl]methyl}amino)acetyl]-2-pyrrolidinecarbonitrile.

Compound D (200 mg, 0.5 mmol) was dissolved in 5 mL acetonitrile and then 500 mg (3.6 mmol) of potassium carbonate was added to the solution. The mixture was stirred for 3 hours at 20° C. and then filtered. The filtrate was concentrated under reduced pressure and the residue was chromatographed on silica gel (5% methanol in methylene chloride) to obtain 177 mg of compound E (yield: 97%).

$^1$H NMR (CDCl$_3$) 400 MHz δ 5.40 (dt, J=3.5, 51.1 Hz, 1H), 4.92 (d, J=9.3 Hz, 1H), 3.85 (m, 1H), 3.66 (m, 1H), 3.50 (m, 3H), 3.38 (m, 3H), 3.20 (m, 2H), 2.55–2.80 (m, 2H), 2.40 (m, 1H), 2.05 (m, 1H), 1.75 (s(br), 1H), 1.68 (m, 1H), 1.32 (dd, J=2.2, 6.8 Hz, 6H) ppm.

Example 20

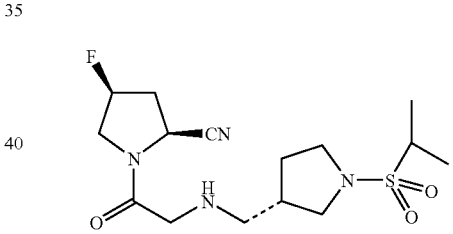

(2S,4S)-4-Fluoro-1-[({[(3S)-1-(isopropylsulfonyl)
pyrrolidinyl]methyl}amino)acetyl]-2-pyrrolidinecarbonitrile and hydrochloride The compound was synthesized exactly as described for their diastereomers' synthesis except (R)-pyrrolidine-3-methanol (*J.Med.Chem.* 1987, 30, 1711) was used as starting material instead of the (S)-enantiomer.

A. [(3R)-1-(Isopropylsulfonyl)pyrrolidinyl]methanol.

$^1$H NMR (CDCl$_3$) 400 MHz δ 4.22 (dd, J=6.2, 10.2 Hz, 1H), 4.14 (dd, J=7.6, 10.2 Hz, 1H), 3.58 (dd, J=7.2, 10.2 Hz, 1H), 3.55 (m, 1H), 3.43 (m, 1H), 3.16–3.36 (m, 3H), 2.70 (m, 1H), 2.12 (m, 1H), 1.78 (m, 1H), 1.43 (d, J=6.9 Hz, 6H), 1.35 (dd, J=1.8, 6.9 Hz, 6H) ppm.

B. (3S)-3-(Azidomethyl)-1-(isopropylsulfonyl)pyrrolidine.

$^1$H NMR (CDC$_3$) 400 MHz δ 3.56 (dd, J=7.1, 9.8 Hz, 1H), 3.52 (m, 1H), 3.30–3.45 (m, 3H), 3.22 (m, 1H), 3.16 (dd, J=1.7 Hz, 4.8 Hz, 1H), 2.49 (m, 1H), 2.08 (m, 1H), 1.75 (m, 1H), 1.35 (dd, J=2.1, 6.8 Hz, 6H) ppm.

C. [(3S)-1-(Isopropylsulfonyl)pyrrolidinyl]methanamine.

$^1$H NMR (CDC$_3$) 400 MHz δ 3.56 (dd, J=7.4, 9.6 Hz, 1H), 3.52 (m, 1H), 3.38 (m, 1H), 3.22 (m, 1H), 3.13 (dd, J=7.3, 9.7 Hz, 1H), 2.75 (m, 1H), 2.32 (m, 1H), 2.07 (m, 1H), 1.65 (m, 3H), 1.34 (dd, J=2.2, 6.9 Hz, 6H) ppm.

D. (2S,4S)-4-Fluoro-1-[({[(3)-1-(isopropylsulfonyl)pyrrolidinyl]methyl}amino) acetyl]-2-pyrrolidinecarbonitrile.hydrochloride.

$^1$H NMR (DMSO-d$_6$) 400 MHz δ 9.20 (s(br), 2H), 5.51 (d, J=51.8 Hz, 1H), 5.04 (d, J=8.8 Hz, 1H), 4.20 (d, J=16.7 Hz, 1H), 3.95 (m, 2H), 3.70 (m, 1H), 3.55 (m, 2H), 3.35 (m, 4H), 3.08 (m, 2H), 3.00 (s(br), 1H), 2.60 (m, 1H), 2.06 (m, 1H), 1.70 (m, 1H), 1.22 (m, 6H) ppm.

E. (2S,4)-4-Fluoro-1-[({[(3S)-1-(isopropylsulfonyl)pyrrolidinyl]methyl}amino)acetyl]-2-pyrrolidinecarbonitrile.

$^1$H NMR (CDCl$_3$) 400 MHz δ 5.41 (dt, J=3.5, 51.1 Hz, 1H), 4.95 (d, J=9.4 Hz, 1H), 3.88 (m, 1H), 3.70 (m, 1H), 3.50 (m, 3H), 3.38 (m, 1H), 3.20 (m, 2H), 2.60–2.80 (m, 2H), 2.40 (m, 1H), 2.20 (s(br), 1H), 2.09 (m, 1H), 1.70 (m, 1H), 1.33 (dd, J=2.2, 7.0 Hz, 6H) ppm.

Example 21

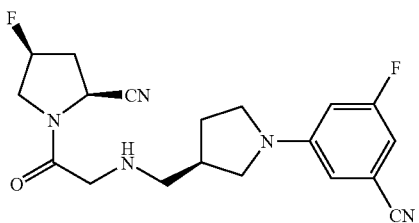

(2S,4S)-1-[({[(3R)-1-(3-Cyano-5-fluorophenyl)pyrrolidinyl]methyl}amino)acetyl]-4-fluoro-2-pyrrolidinecarbonitrile hydrochloride A. 3-Fluoro-5-[(3S)-3-(hydroxymethyl)pyrrolidinyl]benzonitrile.

A stirred solution of (3R)-pyrrolidinylmethanol (808 mg, 8 mmol) (J.Med.Chem. 1987, 30, 1711) and 3,5 difluorobenzonitrile (1.28 g, 12 mmol) in 6 mL of anhydrous DMSO was warmed to 105° C. for two hours and then allowed to cool to room temperature. Ether (200 mL) was added and the solution was extracted with 50 mL H$_2$O (3×). The organic phase was dried with anhydrous magnesium sulfate, filtered and concentrated under reduced pressure. The residue was chromatographed (hexanes-EtOAc 1:1) to obtain 720 mg (yield: 41%) compound A.

$^1$H NMR (CDCl$_3$) 400 MHz δ 6.59 (d, J=8.0 Hz, 1H), 6.53 (s, 1H), 6.40 (dt, J=11.9, 2.2 Hz, 1H), 3.73 (dd, J=6.3, 10.5 Hz, 1H), 3.65 (dd, J=7.1, 10.4 Hz, 1H), 3.42 (dd, J=7.8, 9.5 Hz, 1H), 3.35 (m, 2H), 3.12 (dd, J=6.5, 9.6 Hz, 1H), 2.60 (m, 1H), 2.18 (m, 1H), 1.58 (s(br), 1H) ppm.

B. 3-Fluoro-5-[(3S)-3-(iodomethyl)pyrrolidinyl]benzonitrile.

Iodine (1.02 g, 4 mmol) was added to a stirred solution of 440 mg (2 mmol) of compound A and 2.1 g (8 mmol) of triphenyl phosphine. The mixture was stirred at room temperature for six hours and then filtered. The filtrate was concentrated under reduced pressure and then a mixture of hexanes-EtOAc (3:1) was added. The resulting precipitate was filtered and then the residue was transferred to a silica gel packed column and purified by chromatography (hexanes-EtOAc 5:1) to obtain 580 mg of compound B (yield: 87%).

$^1$H NMR (CDCl$_3$) 400 MHz δ 6.62 (d, J=7.9 Hz, 1H), 6.53 (s, 1H), 6.39 (dt, J=11.7, 2.3 Hz, 1H), 3.50 (dd, J=7.4, 9.4 Hz, 1H), 3.44 (m, 1H), 3.36 (m, 1H), 3.28 (dd, J=6.3, 9.8 Hz, 1H), 3.22 (m, 1H), 3.05(dd, J=7.6, 9.5, 1H), 2.68 (m, 1H), 2.28 (m, 1H), 1.86 (m, 1H) ppm.

C. 3-[(3S)-3-(Azidomethyl)pyrrolidinyl]-5-fluorobenzonitrile.

Sodium azide (200 mg, 3.07 mmol) was added to a stirred solution of compound B (550 mg, 1.66 mmol) in 5 mL DMF. The mixture was stirred for 12 hours and then it was diluted with 100 mL of ethyl acetate. The mixture was extracted with 25 mL water (3×) and then the organic phase was dried with anhydrous magnesium sulfate, filtered, and concentrated under reduced pressure to obtain 390 mg (yield: 96%) of compound C.

$^1$H NMR (CDCl$_3$) 400 MHz δ 6.62 (d, J=7.8 Hz, 1H), 6.53 (s, 1H), 6.39 (dt, J=11.7, 2.2 Hz, 1H), 3.40 (m, 5H), 3.05 (dd, J=6.7, 9.4 Hz, 1H), 2.63 (m, 1H), 2.22 (m, 1H), 1.86 (m, 1H) ppm.

D. 3-[(3R)-3-(Aminomethyl)pyrrolidinyl]-5-fluorobenzonitrile.

Compound C (390 mg, 1.59 mmol) was dissolved in 10 mL of ethanol and then 200 mg of 10% Pd/C was added to the solution. The mixture was stirred for one hour under 1 atm hydrogen at 20° C. The mixture was filtered to remove the catalyst and the filtrate was concentrated under reduced pressure to obtain 350 mg (Yield: 100%) of compound D.

$^1$H NMR (DMSO-d$_6$) 400 MHz δ 6.85 (d, J=8.3 Hz, 1H), 6.71 (s, 1H), 6.39 (d, J=12.6 Hz, 1H), 3.20–3.45 (m, 5H), 3.04 (dd, J=6.7, 9.8 Hz, 1H), 2.69 (d, J=7.1 Hz, 1H), 2.40 (m, 1H), 2.07 (m, 1H), 1.74 (m, 1H) ppm.

E. (2S,4S)-1-[({[(3R)-1-(3-Cyano-5-fluorophenyl)pyrrolidinyl]methyl}amino)acetyl]4-fluoro-2-pyrrolidinecarbonitrile.

A solution of 1-N-bromoacetyl-(2S)-cyano-(4S)-fluoropyrrolidine (236 mg, 1.0 mmol) in 5 mL acetonitrile was added to a stirred solution of compound D (350 mg, 1.59 mmol) and N,N-diisopropylethylamine (258 mg, 2 mmol) in 5 mL acetonitrile at 50° C. The mixture was stirred at 50° C. for one hour then cooled to room temperature. The solvent was evaporated under reduced pressure and the compound E was obtained by crystallization from 1 mL dichloromethane at 0° C. (67 mg, yield: 18%).

$^1$H NMR (DMSO-d$_6$) 400 MHz δ 9.05 (s(br), 2H), 6.90 (d, J=8.2 Hz, 1H), 6.74 (s, 1H), 6.62 (d, J=12.3 Hz, 1H), 5.53 (d, J=51.7 Hz, 1H), 5.06 (d, J=8.8 Hz, 1H), 4.24 (d, J=16.5 Hz, 1H), 4.0 (m, 2H), 3.70 (m, 1H), 3.46 (t, J=9.6 Hz, 1H), 3.30 (m, 2H), 3.12 (t, J=6.9 Hz, 1H), 3.00 (m, 2H) 2.70 (m, 1H), 2.20 (m, 1H), 1.82 (m, 1H) ppm.

Example 22

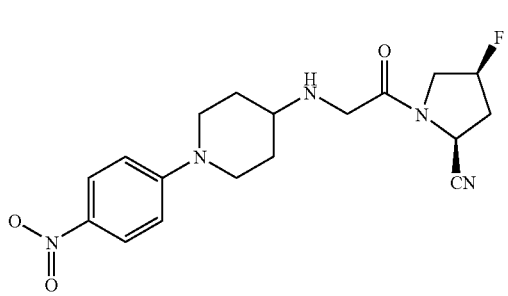

(2S,4S)-4-Fluoro-1-({[1-(4-nitrophenyl)piperidin-4-yl]amino}acetyl)pyrrolidine-2-carbonitrile A. 1-(4-Nitrophenyl)piperidin-4-amine hydrochloride.

Tert-butyl piperidin-4-ylcarbamate (1.0 g, 5.0 mmol) was mixed with 4-bromonitrobenzene (2.0 g, 10.0 mmol), triethylamine (2.0 mL) and DMF (20 mL). The reaction mixture was stirred at 100° C. for a period of 2.0 hours and allowed to cool to RT. The reaction mixture was partitioned between EtOAc and saturated $NaHCO_3$ and the organics were then washed with saturated NaCl. The organics were dried over anhydrous $MgSO_4$ and concentrated to dryness. The resulting crude orange solid was mixed with 1,4-dioxane (5.0 mL) and 4.0 N HCl in 1,4-dioxane (25 mL). The reaction stirred at RT for a period of 16.0 hours followed by concentrating to dryness. The bright yellow solid was triturated using ether and the resulting solid was filtered. After drying under high vacuum the reaction yielded a total of 953 mg of pure hydrochloride salt.

$^1$H NMR ($D_2O$) 400 MHz δ 8.02 (d, 2H, J=8.8 Hz), 6.93 (d, 2H, J=8.8 Hz), 4.00–3.92 (m, 2H), 3.43–3.32 (m, 1H), 3.03–2.91 (m, 2H), 2.02–1.95 (m, 2H), 1.61–1.50 (m, 2H) ppm.

B. (2S,4S)-4-Fluoro-1-({[1-(4-nitrophenyl)piperidin-4-yl]amino}acetyl)pyrrolidine-2-carbonitrile A round bottom flask was mixed compound A (493 mg, 1.91 mmol), (2S4S)-1-(bromoacetyl)-4-fluoropyrrolidine-2-carbonitrile (300 mg, 1.28 mmol), N,N-diisopropylethylamine (1.0 mL) and acetonitrile (10 mL). The reaction mixture was allowed to stir at RT for 17.0 hours. The reaction mixture was concentrated to dryness. The reaction mixture was partitioned between EtOAc and saturated $NaHCO_3$ and the organics were dried over $MgSO_4$. The organics were concentrated to dryness and dried in vacuo. The resulting crude solid was purified using silica gel chromatography (99% $CH_2Cl_2$/1% MeOH, with 1.7% $NH_3$) to yield 200 mg of pure solid.

$^1$H NMR ($D_4$MeOH) 400 MHz δ 8.08 (d, 2H, J=9.0 Hz), 6.95 (d, 2H, J=9.0 Hz), 5.45 (d(br), 1H, J=50.4 Hz), 4.96 (d(br), 1H, J=8.0 Hz), 4.10–3.41 (m, 6H), 3.10–2.98 (m, 2H), 2.87–2.74 (m, 1H), 2.70–2.33 (m, 2H), 2.08–1.97 (m, 2H), 1.51–1.39 (m, 2H) ppm.

Example 23

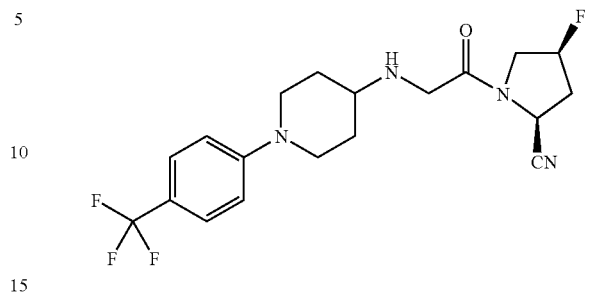

(2S,4S)-4-Fluoro-1-[({1-[4-(trifluoromethyl)phenyl]piperidin-4-yl}amino)acetyl]pyrrolidine-2-carbonitrile hydrochloride A. Tert-butyl 1-[4-(trifluoromethyl)phenyl]piperidin-4-ylcarbamate.

A 100 mL round bottom flask was mixed with 4-triflouromethylbromobenzene (3.2 g, 15.0 mmol), triisopropylphosphine (10.0 mg, 0.062 mmol), Pd(OAc)$_2$ (3.0 mg, 0.013 mmol) and xylenes (50 mL). The reaction mixture was allowed to heat at 110° C. for a period of 30 min at which it was mixed with tert-butyl piperidin-4-ylcarbamate (1.0 g 5.0 mmol). The reaction mixture stirred at 120° C. for 4.0 hours and then cooled to RT. The reaction mixture was partitioned between EtOAc and saturated $NaHCO_3$. The organics were dried over $MgSO_4$ and concentrated to a crude oil. The oil was purified using silica gel chromatography (90% hexanes/10% EtOAc) to yield a total of 472 mg of mostly pure solid.

$^1$H NMR (CDCl$_3$) 400 MHz δ 7.44 (d, 2H, J=8.3 Hz), 6.92 (d, 2H, J=8.3 Hz), 3.81–3.68 (m, 2H), 2.96–2.83 (m, 2H), 2.12–1.84 (m, 2H), 1.60–1.09 (m, 12H), ppm.

B.1-[4-(Trifluoromethyl)phenyl]piperidin-4-amine hydrochloride.

A round bottom flask was mixed with tert-butyl 1-[4-(trifluoromethyl)phenyl]piperidin-4-ylcarbamate (472 mg, 1.42 mmol) and a solution of 4.0 N HCl in 1,4-dioxane (20 mL). The reaction mixture was allowed to stir at RT for a period of 17.0 hours. After 17.0 hours the reaction mixture was concentrated to dryness to afford a crude solid. The resulting solid was triturated with ether and filtered to give a total of 377 mg of desired product (92% yield). The product was used without further purification.

$^1$H NMR (d$_6$-DMSO) 400 MHz δ 7.57–7.44 (m, 2H, J=8.8 Hz), 7.07 (d, 2H, J=8.8 Hz), 3.96–3.82 (m, 2H), 3.65–3.57 (m, 1H), 2.98–2.85 (m, 2H), 2.02–1.95 (m, 2H), 1.62–1.42 (m, 2H) ppm.

C. (2S,4S)-4-Fluoro-1-[({1-[4-(trifluoromethyl)phenyl]piperidin-4-yl}amino)acetyl]pyrrolidine-2-carbonitrile hydrochloride.

A round bottom flask was mixed with 1-[4-(trifluoromethyl)phenyl]piperidin-4-amine hydrochloride (337 mg, 1.34 mmol), (2S,4S)-1-(bromoacetyl)-4-fluoropyrrolidine-2-carbonitrile (316 mg, 1.34 mmol), trietylamine (408 mg, 04.03 mmol) and acetonitrile (20 mL). The reaction mixture was allowed to stir at RT for 17.0 hours. The reaction mixture was concentrated to dryness. The reaction mixture was partitioned between EtOAc and saturated $NaHCO_3$ and the organics were dried over $MgSO_4$. The organics were concentrated to dryness and dried in vacuo. The resulting crude solid was purified using silica gel chromatography (99% CH$_2$Cl$_2$/1% MeOH, with 1.7% NH$_3$) to yield a pure solid. The solid was dissolved into a 1/1 acetone/ether solution and mixed with several drops of 4.0 N HCl in 1,4-dioxane. The resulting solid was filtered and dried in vacuo to give a total of 277 mg of pure solid.

$^1$H NMR (CDCl$_3$) 400 MHz δ 7.45 (d, 2H, J=8.4 Hz), 6.93 (d, 2H, J=8.4 Hz), 5.42 (d(br), 1H, J=50.8 Hz), 4.97 (d(br), 1H, J=9.2 Hz), 3.98–3.77 (m, 1H), 3.80–3.61 (m, 2H), 3.50 (m, 2H), 2.96–2.80 (m, 2H) 2.78–2.64 (m, 2H), 2.56–2.22 (m, 1H), 2.17–1.77 (m, 4H), 1.61–1.47 (m, 2H) ppm.

Example 24

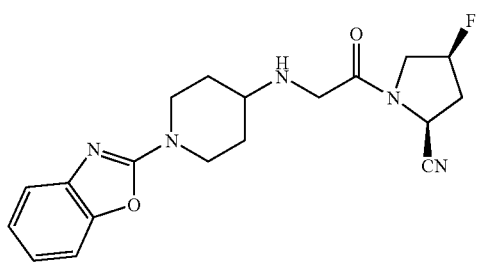

(2S,4S)-1-({[1-(1,3-Benzoxazol-2-yl)piperidin-4-yl] amino}acetyl)-4-fluoropyrrolidine-2-carbonitrile hydrochloride A. 1-(1,3-Benzoxazol-2-yl)piperidin-4-amine hydrochloride.

A sealed tube reactor was mixed with tert-butyl piperidin-4-ylcarbamate (1.0 g, 5.0 mmol) and 2-chlorobenzoxazole (2.3 g, 15.0 mmol). The reactor was sealed and the tube was heated while stirring at a temperature of 100° C. for 2.0 hours. The tube was cooled to RT and the resulting oily solid was dissolved in 4.0 N HCl in 1,4 dioxane (25 mL). The reaction stirred over 16.0 hours and was concentrated to dryness. The resulting solid was triturated with ether and filtered. The product was washed with ether and dried to give 1.1 g of crude solid.

B. (2S,4S)-1-({[1-(1,3-Benzoxazol-2-yl)piperidin-4-yl] amino}acetyl)-4-fluoropyrrolidine-2-carbonitrile hydrochloride.

A round bottom flask was mixed with compound A (1.1 g, 4.25 mmol), (2S,4S)-1-(bromoacetyl)-4-fluoropyrrolidine-2-carbonitrile (described earlier) (500 mg, 2.13 mmol), triethylamine (1.0 mL) and acetonitrile (10 mL). The reaction mixture was allowed to stir at RT for 17.0 hours. The reaction mixture was concentrated to dryness. The reaction mixture was partitioned between EtOAc and saturated NaHCO$_3$ and the organics were dried over MgSO$_4$. The organics were concentrated to dryness and dried in vacuo. The resulting crude solid was purified using silica gel chromatography (99% CH$_2$Cl$_2$/1% MeOH, with 1.7% NH$_3$) to yield a pure solid (111 mg). The solid was dissolved into a 1:1 acetone/ether solution and mixed with several drops of 4.0 N HCl in 1,4-dioxane. The resulting solid was filtered and dried in vacuo to give a total of 78 mg of compound A.

$^1$H NMR (d$_4$MeOH) MHz δ 7.62 (d, 1H, J=7.9 Hz), 7.50–7.38 (d, 3H), 5.50 (d(br), 1H, J=52 Hz), 5.07 (d(br), 1H, J=9.2 Hz), 4.64–3.52 (m, 9H), 2.77–2.36 (m, 4H), 2.08–1.89 (m, 2H) ppm.

Example 25

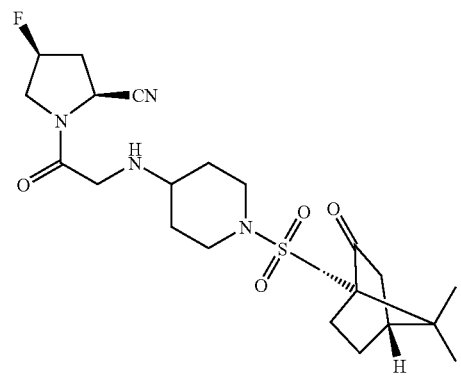

(2S,4S)-1-({[1-({[(1R,4R)-7,7-dimethyl-2-oxobicyclo[2.2.1]hept-1-yl]methyl}sulfonyl)piperidin-4-yl] amino}acetyl)-4-fluoropyrrolidine-2-carbonitrile hydrochloride A. Tert-butyl 1-({[(1S,4S)-7,7-dimethyl-2-oxobicyclo [2.2.1]hept-1-yl]methyl}sulfonyl)piperidin-4-ylcarbamate.

4-N—BOC-amino-piperidine (0.334 g, 1.67 mmol) was dissolved in 5 mL of dry dichloromethane. N,N-diisopropylethylamine (0.873 mL, 4.98 mmol) was added followed by the addition of (1R)-(−)-camphorsulfonyl chloride (0.50 g, 2.0 mmol) and the resulting mixture was stirred at RT for 18 hours. The solvent was then removed in vacuo and the resulting residue was dissolved in 15 ml of ethyl acetate. 15 mL of a solution of saturated sodium bicarbonate was added and the reaction was extracted with ethyl acetate. The combined organic extracts were washed with saturated NaCl. The organics were dried over MgSO$_4$ and concentrated to dryness to give 0.664 g (96% yield) of compound A that was carried on without further purification.

$^1$H NMR (CDCl$_3$) 400 MHz δ 4.64–4.39 (m, 1H) 3.91–3.70 (d, 2H), 3.69–3.50 (m, 1H), 3.13–2.85 (m, 2H) 2.63–2.25 (m, 2H), 2.21–1.89 (m, 6H), 1.65 (s, 6H) 1.42 (s, 9H) ppm B. (1S,4S)-1-{[(4-Aminopiperidin-1-yl)sulfonyl]methyl}-7, 7-dimethylbicyclo[2.2.1]heptan-2-one4-methylbenzenesulfonate Compound A (0.664 g, 1.60 mmol) was dissolved in 5 mL of acetonitrile. To this stirring solution was added p-toluenesulfonic acid monohydrate (0.305 g, 1.60 mmol) and the resulting mixture was stirred for a period of 24 hours at RT. A white precipitate formed during the course of the reaction, which was removed by filtration. The filtrate was washed 3 times with 10 mL of ethyl acetate. The filtrate was dried on high vacuum to give 0.780 g (99% yield) of compound B.

$^1$H NMR (CDCl$_3$) 400 MHz δ 7.49 (d, 2H, J=7.3 Hz), 7.16 (d, 2H, J=7.3 Hz), 4.15 (m, 1H), 3.93–3.72 (m, 2H), 3.69–3.50 (m, 1H), 3.13–2.85 (m, 2H), 2.64–2.26 (m, 2H), 2.21 (s, 3H), 2.21–1.89 (m, 6H), 1.64 (s, 6H) ppm.

C. (2R,4R)-1-({[1-({[(1S,3S)-3-Ethyl-1,2,2-trimethyl-5-oxocyclopentyl]methyl}sulfonyl)piperidin-4-yl]amino}acetyl)-4-fluoropyrrolidine-2-carbonitrile.

Compound B (0.729 g, 1.5 mmol) was dissolved in dry acetonitrile (3 mL). N,N-diisopropylethylamine (1.3 mL, 7.5 mmol) was added and the mixture was warmed to 50° C. (2S,4S)-1-(2-Bromoacetyl)-4-fluoro-pyrrolidine-2-carbonitrile (described earlier) (0.352 g, 1.5 mmol) in 2 mL dry acetonitrile was then added and the mixture dropwise over 10 min. The mixture was stirred at 50° C. for 1 hour. The solvent was then removed in vacuo and the resulting residue was dissolved in methylene chloride and the resulting solution was cooled to 0° C. A white precipitate formed after a few minutes and was filtered off. The precipitate was washed 3 times with 5 mL methylene chloride and dried under high vacuum for 3 hours to afford 0.50 g of compound C (71% yield).

$^1$H NMR (CDCl$_3$) 400 MHz δ 5.56 (d, 1H, J=50.1 Hz), 4.96 (d, 1H, J=9.3 Hz), 4.53 (s, 1H), 3.69–3.30 (m, 7H), 3.40–3.35 (m, 4H), 3.23–3.05 (m, 2H), 2.76–2.52 (m, 2H), 2.49–2.36 (m, 2H), 2.28–1.62 (m, 6H), 1.42 (s, 6H), 1.32–1.24 (m, 2H) ppm.

D. (2S,4S)-1-{[(1-{[(7,7-Dimethyl-2-oxobicyclo[2.2.1]hep-1-yl)methyl]sulfonyl}piperidin-4-yl)amino]acetyl}-4fluoropyrrolidine-2-carbonitrile hydrochloride.

Compound C (0.500 g, 1.1 mmol) was combined with 5 mL of 2.0 M HCl in ether. The mixture was stirred at RT for 30 min. The solvent was removed in vacuo to give 0.553 g of compound D.

$^1$H NMR (CDCl$_3$) 400 MHz δ 5.47 (d, 1H, J=50.1 Hz), 4.98 (d, 1H, J=9.3 Hz), 4.54 (s, 1H), 3.69–3.32 (m, 7H), 3.39–3.34 (m, 4H), 3.22–3.06 (m, 2H), 2.76–2.52 (m, 2H), 2.49–2.36 (m, 2H), 2.29–1.63 (m, 6H), 1.42 (s, 6H), 1.33–1.25 (m, 2H) ppm.

Example 26

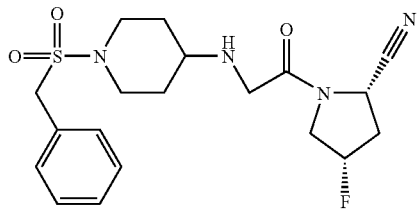

(2S,4S)-1-({[1-(Benzylsulfonyl)piperidin-4-yl]amino}acetyl)-4-fluoropyrrolidine-2-carbonitrile hydrochloride A. (1-Phenylmethanesulfonyl-piperidin-4-yl)-carbamic acid tert-butyl ester.

4-N—BOC-amino-piperidine (2.0 g, 9.90 mmol) was dissolved in 15 mL of dry dichloromethane. N,N-diisopropylethylamine (3.4 mL, 19.80 mmol) was added followed by the addition of benzylsulfonyl chloride (2.1 g, 10.9 mmol) and the resulting mixture was stirred at RT for 18 hours. The solvent was then removed in vacuo and the resulting residue was dissolved in 25 mL of ethyl acetate. Saturated sodium bicarbonate (65 mL) was added and the reaction was extracted with ethyl acetate. The combined organic extracts were washed with saturated NaCl. The organics were dried over MgSO$_4$ and concentrated to dryness to give 3.19 g (94% yield) of compound A that was carried on without further purification.

$^1$H NMR (CDCl$_3$) 400 MHz δ 7.45–7.24 (m, 5H), 4.46 (s, 2H), 3.48–3.22 (m, 2H), 3.24–3.00 (m, 1H), 2.90–2.58 (m, 2H), 2.02–1.81 (m, 2H), 1.67–1.27 (s, 11H) ppm.

B. (1-Phenylmethanesulfonyl)-piperidin-4-ylamine p-toluene sulfonate

Compound A (1.0 g, 2.82 mmol) was dissolved in 15 mL of acetonitrile. To this stirring solution was added p-toluenesulfonic acid monohydrate (0.590 g, 3.10 mmol) and the resulting mixture was stirred for a period of 24 hours at RT. A white precipitate formed during the course of the reaction, which was removed by filtration. The filtrate was washed 3 times with 15 mL of ethyl acetate. The filtrate was dried on high vacuum to give 1.2 g (99% yield) of compound B.

$^1$H NMR (CDCl$_3$) 400 MHz δ 7.34 (m, 5H) 7.42 (d, J=7.3 Hz, 2H), 7.08 (d, J=7.3 Hz, 2H), 4.46 (s, 2H), 3.48–3.22 (m, 2H), 3.24–3.00 (m, 1H), 2.90–2.58 (m, 2H), 2.24 (s, 3H), 2.02–1.81 (m, 2H), 1.67–1.27 (m, 2H) ppm.

C. (2S,4S)-1-({[1-(Benzylsulfonyl)piperidin-4-yl]amino}acetyl)-4-fluoropyrrolidine-2-carbonitrile.

Compound B (1.0 g, 2.47 mmol) was dissolved in dry acetonitrile (15 mL). N,N-diisopropylethylamine (1.0 mL, 6.15 mmol) was added to the stirring solution and the mixture was allowed to continue stirring until all material was dissolved. Solid (2S,4S)-1-(2-bromoacetyl)-4-fluoropyrrolidine-2-carbonitrile (described previously) (0.290 g, 1.23 mmol) was then added and the mixture was stirred at RT for 18 hours. The solvent was then removed in vacuo and the resulting residue was dissolved in ethyl acetate. 15 mL of 0.1 M NaOH was added to the solution along with 25 mL of saturated NaCl. The mixture was washed 3 times with 25 mL of ethyl acetate and the combined organic extracts were dried over MgSO$_4$ and concentrated in vacuo. The resulting solid was chromatographed on 35 g of silica gel (1% to 50% ethylacetate/99% b to 95% hexanes) to afford 0.524 g of compound C (52% yield).

$^1$H NMR (CDCl$_3$) 400 MHz δ 7.47–7.26 (m, 5H), 5.51 (d, 1H, J=50.1 Hz), 4.95 (d, 1H, J=9.3 Hz), 4.71–4.22 (d, 3H), 3.89–3.23 (m, 4H), 3.24–3.00 (m, 1H), 2.95–2.66 (m, 4H), 2.07–1.86 (m, 2H), 1.59 (s, 2H) ppm.

D. (2S,4S)-1-({[1-(Benzylsulfonyl)piperidin-4-yl]amino}acetyl)-4-fluoropyrrolidine-2-carbonitrile hydrochloride.

Compound C (0.524 g, 1.28 mmol) was combined with 5 mL of 2.0 M HCl in ether. The mixture was stirred at RT for 30 min. The solvent was removed in vacuo to give 0.570 g of compound E.

$^1$H NMR (CDCl$_3$) 400 MHz δ 7.49–7.27 (m, 5H), 5.55 (d, 1H, J=50.1 Hz), 4.97 (d, 1H, J=9.3 Hz), 4.73–4.24 (m, 3H), 3.91–3.25 (m, 4H), 3.25–3.04 (m, 1H), 2.97–2.67 (m, 4H), 2.09–1.88 (m, 2H), 1.59 (s, 2H) ppm.

Example 27

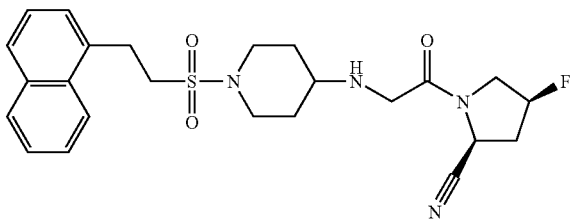

(2S,4S)-4-Fluoro-1-{[(1-{[2-(1-naphthyl)ethyl]
sulfonyl}piperidin-4-yl)amino]acetyl}pyrrolidine-2-
carbonitrile hydrochloride A. [1-(2-Naphthalen-1-yl-ethanesulfonyl)-piperidin-4-yl]-carbamic acid tert-butyl ester.

4-N—BOC-amino-piperidine (0.326 g, 1.63 mmol) was dissolved in 5 mL of dry dichloromethane. N,N-diisopropylethylamine (0.860 mL, 4.91 mmol) was added followed by the addition of 2-(1-naphthyl)ethanesulfonyl chloride (0.50 g, 1.96 mmol) and the resulting mixture was stirred at RT for 18 hours. The solvent was then removed in vacuo and the resulting residue was dissolved in 15 ml of ethyl acetate. 25 mL of a solution of saturated sodium bicarbonate was added and the reaction was extracted with ethyl acetate. The combined organic extracts were washed with saturated NaCl and then the organics were dried over $MgSO_4$ and concentrated to dryness to give 0.630 g (94% yield) of compound A that was carried on without further purification.

hu 1H NMR ($CDCl_3$) 400 MHz δ 8.29–7.33 (m, 7H), 4.53–4.35 (m, 1H), 4.00–3.75 (m, 1H), 3.72–3.48 (m, 3H), 3.44–3.21 (m, 2H), 2.91 (s, 2H), 2.02 (s, 2H), 1.76–1.51 (m, 3H), 1.44 (s, 9H) ppm.

B. 1-(2-Naphthalen-1-yl-ethanesulfonyl)-piperidin-4-ylamine p-toluene sulfonate.

Compound A (0.630 g, 1.51 mmol) was dissolved in 5 mL of acetonitrile. To this stirring solution was added p-toluenesulfonic acid monohydrate (0.287 g, 1.51 mmol) and the resulting mixture was stirred for a period of 24 hours at RT. A white precipitate formed during the course of the reaction, which was removed by filtration. The filtrate was washed 3 times with 10 ml of ethyl acetate. The filtrate was dried on high vacuum to give 0.738 g (99% yield) of compound B.

1H NMR ($CDCl_3$) 400 MHz δ 8.26 (s, 3H), 8.10–7.38 (m, 11H), 3.76–3.59 (m, 2H), 3.55–3.31 (m, 6H), 3.07–2.77 (m, 2H), 2.53 (s, 3H), 1.73–1.41 (m, 2H) ppm.

C. (2S,4S)-4-Fluoro-1-{[(1-{[2-(1-naphthyl)ethyl]sulfonyl}piperidin-4-yl)amino]acetyl}pyrrolidine-2-carbonitrile.

Compound C (0.701 g, 1.43 mmol) was dissolved in dry acetonitrile (5 mL). N,N-diisopropylethylamine (0.625 mL, 3.57 mmol) was added to the stirring solution and the mixture was allowed to continue stirring until all material was dissolved. Solid (2S,4S)-1-(2-bromoacetyl)-4-fluoropyrrolidine-2-carbonitrile (described earlier) (0.167 g, 0.714 mmol) was then added and the mixture was stirred at RT for 18 hours. The solvent was then removed in vacuo and the resulting residue was dissolved in ethyl acetate. 15 mL of 0.1 M NaOH was added to the solution along with 10 mL of saturated NaCl. The mixture was washed 3 times with 15 mL of ethyl acetate and the combined organic extracts were dried over $MgSO_4$ and concentrated in vacuo. The resulting solid was chromatographed on 35 g of silica gel (5% to 10% EtOAc/95% to 90% hexanes) to afford 0.273 g of compound C (40% yield).

1H NMR ($CDCl_3$) 400 MHz δ 8.28–7.20 (m, 7H) 5.38 (d, 1H, J=50.1 Hz), 4.94 (d, 1H, J=9.3 Hz), 4.51–4.27 (m, 1H), 3.96–3.64 (m, 7H), 3.62–3.45 (m, 2H) 3.38–3.29 (m, 2H), 3.29–3.11 (m, 2H) 2.97–2.13 (m, 6H), 1.45 (s, 2H) ppm.

D. (2S,4S)-4-Fluoro-1-{[(1-{[2-(1-naphthyl)ethyl]sulfonyl}piperidin-4-yl)amino]acetyl}pyrrolidine-2-carbonitrile hydrochloride.

Compound C (0.273 g, 0.578 mmol) was combined with 5 mL of 2.0 M HCl in ether. The mixture was stirred at RT for 30 min and then the solvent was removed in vacuo to give 0.293 g of compound D.

1H NMR ($CDCl_3$) 400 MHz δ 8.27–7.21 (m, 7H) 5.38 (d, 1H, J=50.1 Hz), 4.94 (d, 1H, J=9.3 Hz), 4.53–4.29 (m, 1H), 3.98–3.65 (m, 7H), 3.64–3.46 (m, 2H) 3.39–3.29 (m, 2H), 3.31–3.12 (m, 2H) 2.98–2.14 (m, 6H), 1.46 (s, 2H) ppm.

Example 28

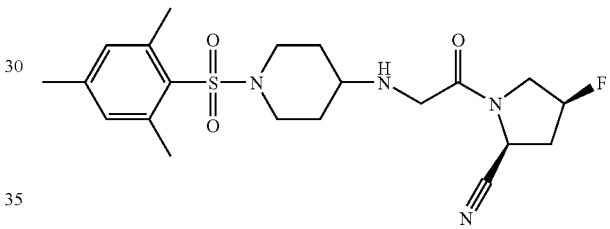

(2S,4S)-4Fluoro-1-({[1-(mesitylsulfonyl)piperidin-4-yl]amino}acetyl)pyrrolidine-2-carbonitrile hydrochloride A. [1-(2,4,6-Trimethyl-benzenesulfonyl)-piperidin-4-yl]-carbamic acid tert-butyl ester.

4-N—BOC-amino-piperidine (0.500 g, 2.49 mmol) was dissolved in 5 mL of dry dichloromethane. N,N-diisopropylethylamine (1.3 mL, 7.47 mmol) was added followed by the addition of 2-mesitylenesulfonyl chloride (0.652 g, 2.99 mmol) and the resulting mixture was stirred at RT for 18 hours. The solvent was then removed in vacuo and the resulting residue was dissolved in 15 ml of ethyl acetate. 25 mL of a solution of saturated sodium bicarbonate was added and the reaction was extracted with ethyl acetate. The combined organic extracts were washed with saturated NaCl. The organics were dried over $MgSO_4$ and concentrated to dryness to give 0.947 g (98% yield) of compound A that was carried on without further purification.

1H NMR ($CDCl_3$) 400 MHz δ 6.98 (s, 2H) 4.56–4.32 (m, 1H), 3.76–3.42 (m, 4H), 3.04–2.69 (m, 2H) 2.64 (s, 6H), 2.21 (s, 3H) 2.04–1.85 (m, 2H), 1.06 (s, 9H) ppm.

B. 1-(2,4,6-Trimethyl-benzenesulfonyl)-piperidin-4-ylamine p-toluenesulfonate.

Compound A (0.947 g, 2.47 mmol) was dissolved in 5 mL of acetonitrile. To this stirring solution was added p-toluenesulfonic acid monohydrate (0.563 g, 2.96 mmol) and the resulting mixture was stirred for a period of 18 hours at RT. A white precipitate formed during the course of the reaction that was removed by filtration. The filtrate was washed 3 times with 10 ml of ethyl acetate and collected into a round bottom flask. The residual ethyl acetate was removed under high vacuum to give 0.525 g (66% yield) of compound B.

$^1$H NMR (CDCl$_3$) 400 MHz δ 8.30 (s, 3H), 7.44 (d, 2H, J=7.2 Hz), 7.10 (d, 2H, J=7.2 Hz), 7.09 (s, 2H) 4.56–4.32 (m, 1H), 3.67–3.32 (m, 4H), 2.94–2.66 (m, 1H) 2.53 (s, 6H), 2.24 (s, 3H) 2.07–1.86 (m, 2H), 1.59 (s, 2H) ppm.

C. (2S,4S)-4-Fluoro-1-({[1-(mesitylsulfonyl)piperidin-4-yl]amino}acetyl)pyrrolidine-2-carbonitrile.

Compound B (0.517 g, 1.6 mmol) was dissolved in dry acetonitrile (5 mL). N,N-diisopropylethylamine (2.0 mL, 11.0 mmol) was added to the stirring solution and the mixture was allowed to continue stirring until all material was dissolved. Solid (2S,4S)-1-(2-bromoacetyl)-4-fluoropyrrolidine-2-carbonitrile (described previously) (0.800 g, 2.5 mmol) was then added and the mixture was stirred at RT for 18 hours. The solvent was then removed in vacuo and the resulting residue was dissolved in ethyl acetate. 15 mL of 0.1 M NaOH was added to the solution along with 10 mL of saturated NaCl. The mixture was washed 3 times with 15 mL of ethyl acetate and the combined organic extracts were dried over MgSO$_4$ and concentrated in vacuo. The resulting solid was chromatographed on 35 g of silica gel (1% MeOH/99% dichloromethane/with 7% NH$_3$) to afford 0.643 g of compound C (67% yield).

$^1$H NMR (CDCl$_3$) 400 MHz δ 7.07 (s, 2H) 5.56 (d, 1H, J=51.2 Hz), 4.98 (d, 1H, J=9.3 Hz), 4.51–4.27 (m, 1H), 4.17–3.43 (m, 6H), 2.95–2.66 (m, 3H) 2.53 (s, 6H), 2.24 (s, 3H) 2.07–1.86 (m, 2H), 1.59 (s, 2H) ppm.

D. (2S,4S)-4-Fluoro-1-({[1-(mesitylsulfonyl)piperidin-4-yl]amino}acetyl)pyrrolidine-2-carbonitrile hydrochloride.

Compound C (0.516 g, 1.6 mmol) was combined with 5 mL of 2.0 M HCl in ether. The mixture stirred at RT for 30 min and then the solvent was removed in vacuo to give desired salt D (0.757 g).

$^1$H NMR (CDCl$_3$) 400 MHz δ 7.09 (s, 2H) 5.56 (d, 1H, J=51.2 Hz), 4.98 (d, 1H, J=9.3 Hz), 4.51–4.27 (m, 1H), 4.17–3.43 (m, 6H), 2.95–2.66 (m, 3H) 2.55 (s, 6H), 2.23 (s, 3H) 2.07–1.86 (m, 2H), 1.59 (s, 2H) ppm.

Example 29

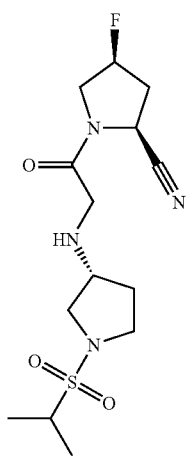

(2S,4S)-4-Fluoro-1-({[(3R)-1-(isopropylsulfonyl)pyrrolidinyl]amino}acetyl)-2-pyrrolidinecarbonitrile hydrochloride A. Tert-butyl (3R)-1-(isopropylsulfonyl)pyrrolidinylcarbamate.

To a solution of isopropylsulfonyl chloride (0.30 mL, 2.67 mmol) in dichloromethane (7 mL) was added a solution of tert-butyl (3S)-pyrrolidinylcarbamate (510 mg, 2.74 mmol) and triethylamine (0.375 mL, 2.69 mmol) in dichloromethane (9 mL). After stirring for 20 min the mixture was poured into water and washed with water and with brine. The organic layer was dried over MgSO$_4$ and the solvent evaporated in vacuo. The crude mixture was chromatographed on silica gel (5% MeOH/95% CHCl$_3$) to yield 740 mg of compound A as a light yellow solid (94% yield).

$^1$H NMR (CDCl$_3$) 300 MHz δ 4.76 (s, 1H), 4.28 (s, 1H), 3.61 (m, 2H), 3.38 (m, 1H), 3.35 (m, 1H), 3.26 (m, 1H), 2.21 (m, 1H), 1.94 (m, 1H), 1.48 (s, 9H), 1.40 (d, J=7 Hz, 6H) ppm.

B. (3R)-1-(Isopropylsulfonyl)-3-pyrrolidinamine hydrochloride.

To a solution of compound A (524 mg, 1.79 mmol) in dioxane (2 mL) was added 4.0 N HCl in dioxane (4 mL, 16 mmol). After stirring overnight the solvent was evaporated in vacuo and the resulting solid taken up in toluene, which was then evaporated in vacuo yielding 348 mg of compound B as a white solid which was used without further manipulation.

$^1$H NMR (d$_6$-DMSO) 300 MHz δ 8.46 (s, 3H), 4.10–3.20 (m, 5H), 2.24 (m, 1H), 2.01 (m, 1H), 1.30 (d, J=7 Hz, 6H).

C. (2S,4S)-4-fluoro-1-({[(3R)-1-(isopropylsulfonyl)pyrrolidinyl]amino}acetyl-2-pyrrolidinecarbonitrile hydrochloride.

To a solution in acetonitrile (10 ml) of (2S,4S)-1-(bromoacetyl)-4-fluoro-2-pyrrolidinecarbonitrile (described earlier) (211 mg, 0.9 mmol) and compound B (348 mg, 1.79 mmol) was added N,N,-diisopropylethylamine (1 mL, 5.8 mmol). After stirring for c.a. 30 h, 1.0 N NaOH (ca. 20 ml) was added and the mixture poured into water and extracted with ethyl acetate. The combined organic layers were dried over MgSO$_4$ and the solvent evaporated in vacuo. The residue was chromatographed on silica gel (1% MeOH/99% CH$_2$Cl$_2$ then 5% MeOH/95% CH$_2$Cl$_2$) to afford an impure solid. The solid was chromatographed again on silica gel (10% MeOH/10% EtOAc) to yield 234 mg of an oil which was taken up in diethyl ether (ca. 4.5 mL) and acetone (ca. 2.5 mL). Then 1.0 M HCl in ether (ca. 7 mL) was added to precipitate a white solid which was filtered and dried in vacuo to afford 127 mg of compound C as an off-white solid (41% yield).

$^1$H NMR (d$_6$-DMSO, 100° C.) 300 MHz δ 5.51 (d, J=52 Hz, 1H), 4.96 (m, 1H), 4.00–3.28 (m, 10H), 3.18–2.98 (m, overlapping with H$_2$O), 2.62–2.31 (m, overlapping with DMSO), 2.04 (m, 1H), 1.81 (m, 1H), 1.29 (d, J=7 Hz, 6H).

Example 30

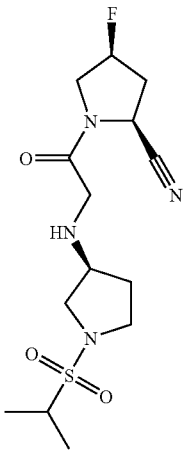

(2S,4S)-4-Fluoro-1-({[(3S)-1-(isopropylsulfonyl)pyrrolidinyl]amino}acetyl)-2-pyrrolidinecarbonitrile hydrochloride A. Tert-butyl (3S)-1-(isopropylsulfonyl)pyrrolidinylcarbamate.

To a solution of isopropylsulfonyl chloride (0.30 mL, 2.67 mmol) in dichloromethane (7 mL) was added a solution of tert-butyl (3S)-pyrrolidinylcarbamate (510 mg, 2.74 mmol) and triethylamine (0.40 mL, 2.87 mmol) in dichloromethane (9 mL). After stirring for 20 min the mixture was poured into water and washed with water and with brine. The organic layer was dried over $MgSO_4$ and the solvent evaporated in vacuo. The crude mixture was chromatographed on silica gel (5% MeOH/95% $CHCl_3$) to yield 676 mg of compound A as a light yellow solid (2.31 mmol, 94% yield).

$^1$H NMR ($d_6$-DMSO) MHz δ 7.22 (m, 1H), 4.01 (m, 1H), 3.51–3.29 (m, overlap with $H_2O$), 3.11 (m, 1H), 2.06 (m, 1H), 1.80 (m, 1H), 1.41 (s, 9H), 1.24 (d, J=7 Hz, 6H)

B. (3S)-1-(Isopropylsulfonyl)-3-pyrrolidinamine hydrochloride.

To a solution of compound A (676 mg, 2.31 mmol) in dioxane (2.5 mL) was added 4.0 N HCl in dioxane (5.2 mL, 20.8 mmol). After stirring overnight, the solvent was evaporated in vacuo and the resulting solid taken up in toluene, which was then evaporated in vacuo yielding 430 mg of compound B as a white solid which was used without further manipulation.

$^1$H NMR ($d_6$-DMSO) 300 MHz δ 8.46 (s, 3H), 3.84 (s, 1H), 3.67–3.50 (m, 4H), 3.39 (m, overlap with $H_2O$), 2.24 (m, 1H), 2.01 (m, 1H), 1.27 (d, J=7 Hz, 6H)

C. (2S,4S)-4-Fluoro-1-({[(3S)-1-(isopropylsulfonyl)pyrrolidinyl]amino}acetyl)-2-pyrrolidinecarbonitrile hydrochloride.

To an $CH_3CN$ solution (10 mL) containing (2S,4S)-1-(bromoacetyl)-4-fluoro-2-pyrrolidinecarbonitrile (described earlier) (200 mg, 0.85 mmol) and compound B (196 mg, 0.86 mmol) was added N,N,-diisopropylethylamine (1 mL, 5.84 mmol). After stirring for 30 hr. 1.0 N NaOH (20 mL) was added and the mixture poured into water and extracted with ethyl acetate. The combined organic layers were dried over $MgSO_4$ and the solvent evaporated in vacuo. The residue was initially chromatographed on silica gel (1% MeOH/99% $CH_2Cl_2$ then 5% MeOH in $CH_2Cl_2$) to afford an impure solid. The solid was chromatographed on silica gel (10% MeOH/90% EtOAc) to yield 234 mg of an oil that was taken up in diethyl ether (ca. 4.5 mL) and acetone (ca. 2.5 mL). Then 1.0 M HCl in ether (ca. 7 mL) was added to precipitate a white solid which was filtered and dried in vacuo to afford 58 mg of compound B as a white solid (0.15 mmol, 18% yield).

$^1$H NMR ($d_6$-DMSO, 100° C.) 300 MHz δ 5.56 (d, J=52 Hz, 1H), 5.04 (m, 1H), 4.19–3.30 (m, 11H), 3.29–2.90 (m, overlapping with $H_2O$), 2.60–2.40 (m, overlapping with DMSO), 2.32 (m, 1H), 2.19 (m, 1H), 1.31 (d, J=7 Hz, 6H).

Example 31

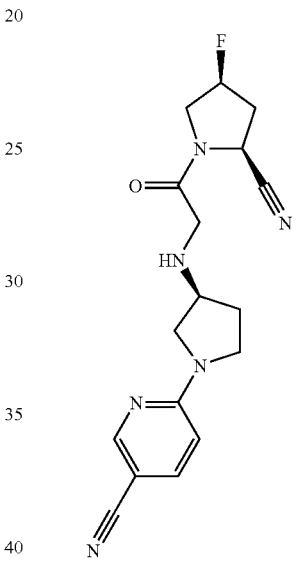

6-[(3S)-3-({2-[(2S,4S)-2-Cyano-4-fluoropyrrolidin-1-yl]-2-oxoethyl}amino)pyrrolidin-1-yl]nicotinonitrile bis(trifluoroacetate)

A. Tert-butyl (3S)-1-(5-cyanopyridin-2-yl)pyrrolidin-3-yl-carbamate.

To a solution of 6-chloronicotinonitrile (277 mg, 2.0 mmol) and N-t-(BOC)-(3S)-3-amino pyrrolidine. (375 mg, 2.0 mmol) in dry ethanol (20 mL) was added potassium carbonate (850 mg, 6.2 mmol). The solution was stirred at reflux for 18 hr. The ethanol was evaporated in vacuo and the residue taken up in ethyl acetate. The mixture was filtered and the ethyl acetate was evaporated. The resulting residue was purified on silica gel (2% MeOH/98% $CHCl_3$) to yield 213 mg of compound A as a white solid (37% yield).

$^1$H NMR ($d_6$-DMSO) 400 MHz δ 8.48 (s, 1H), 7.82 (d, J=9 Hz, 1H), 7.26 (m, 1H), 6.56 (d, J=9 Hz, 1H), 4.15 (m, 1H), 3.58 (m, 3H), 2.15 (m, 1H), 1.92 (m, 1H), 1.41 (s, 9H) ppm.

B. 2-[(3S)-3-Ammoniopyrrolidin-1-yl]-5-cyanopyridinium bis(trifluoroacetate).

To a stirred solution of compound A (333 mg, 1.15 mmol) in dichloromethane (10 mL) was added neat trifluoroacetic acid (0.720 mL, 9.35 mmol). The stirring was continued for 3 hr and starting material was noted, so additional trifluoroacetic acid (2.2 mL, 28.6 mmol) was added. After 4 hr of total reaction time, the dichloromethane was evaporated in vacuo and the residue taken up in dichloromethane. The solvent was then evaporated in vacuo to yield compound B as a yellow oil which was carried on without further manipulation (100% yield).

$^1$H NMR (d$_6$-DMSO) 400 MHz δ 8.49 (s,1H), 8.05 (s(br), 3H), 7.85 (d, J=9 Hz, 1H), 6.60 (d, J=9 Hz, 1H), 3.94–3.57 (m, H$_2$O overlap), 2.30 (m, 1H), 2.08 (m, 1H), ppm.

C. 6-[(3S)-3-({2-[(2S,4S)-2-Cyano-4-fluoropyrrolidin-1-yl]-2-oxoethyl}amino)pyrrolidin-1-yl]nicotinonitrile bis(trifluoroacetate).

Compound B (1.06 g, 2.55 mmol) was dissolved in CH$_3$CN (19 mL) and the solution was warmed slightly. Then N,N-diisopropylethylamine (1.8 mL, 10.5 mmol) was added and the solution was further stirred at 50° C. Then (2S,4S)-1-(bromoacetyl)-4-fluoropyrrolidine-2-carbonitrile (described earlier) in CH$_3$CN (19 mL) was added dropwise over a period of ca. 7 minutes and the mixture was allowed to stir at 50° C. for 1.5 hours. The CH$_3$CN was then removed in vacuo and the residue dissolved in ethyl acetate and was washed with saturated aqueous NaHCO$_3$ followed by brine. The organic layer was dried over MgSO$_4$ and the solvent was evaporated in vacuo. The resulting residue was chromatographed on silica gel (15% MeOH/85% CHCl$_3$) to afford a white powder. The free base was dissolved in enough CH$_2$Cl$_2$ to make it 0.1 M followed by addition of 2.2 equiv. of trifluoroacetic acid. The solution was concentrated in vacuo to afford 521 mg of compound C as a white solid (72% yield).

$^1$H NMR (d$_6$-DMSO) 400 MHz δ 9.39 (brs, 2H), 8.50 (s, 1H), 7.87 (d, J=9 Hz, 1H), 6.58 (d, J=9 Hz, 1H), 5.54 (d, J=52 Hz, 1H), 5.05 (d, J=9 Hz, 1H), 4.06–3.48 (m, 7H), 2.39 (m, 2H) ppm.

Example 32

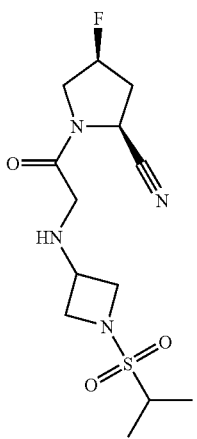

2S,4S)-4-Fluoro-1-({[1-(isopropylsulfonyl)azetidin-3-yl]amino}acetyl)pyrrolidine-2-carbonitrile trifluoroacetate A. 1-(Tert-butoxycarbonyl)azetidine-3-carboxylic acid.

Azetidine-3-carboxylic acid (960 mg, 9.49 mmol) was dissolved in 1,4-dioxane (25 mL), water (11 mL) and 1.0 N NaOH (14 mL). Solid di-t-butyl dicarbonate was added and the mixture was stirred at RT for 5 hours. KHSO$_4$ was added to make the pH 2 and then the dioxane was evaporated in vacuo followed by extraction of the aqueous layer with ethyl acetate. The combined organic layers were dried over MgSO$_4$ and the solvent evaporated in vacuo to yield 1.50 g of compound A as a white solid which was used without further purification (94% yield).

$^1$H NMR (d$_6$-DMSO) 400 MHz δ 3.96 (m, 2H), 3.83 (m, 2H), 3.30 (m, 1H), 1.35 (s, 9H) ppm.

B. Tert-butyl 3-({[2-(trimethylsilyl)ethoxy]carbonyl}amino)azetidine-1-carboxylate.

To a solution of compound A (1.00 g, 4.98 mmol) in toluene (30 mL) was added triethylamine (0.85 mL, 6.10 mmol). Whilst stirring at RT, diphenylphosphorylazide (1.18 mL, 5.48 mmol) was added followed by warming to 80° C. After 1 hr, 2-trimethylsilylethanol (1.5 mL, 9.96 mmol) was added and the mixture was allowed to stir for 31 hr. The mixture was then washed with saturated NaHCO$_3$, dried over MgSO$_4$ and concentrated. The residue was chromatographed on silica gel (25% EtOAc75% hexanes) to afford compound B as a white solid (61% yield).

$^1$H NMR (d$_6$-DMSO) 400 MHz δ 7.65 (1, 1H), 4.19 (m, 1H), 4.01 (m, 1H), 3.64 (m, 2H), 1.34 (s, 9H), 0.88 (m, 2H), 0.00 (s, 7H) ppm.

C. 2-(Trimethylsilyl)ethyl azetidin-3-ylcarbamate tosylate.

To a solution of compound B (783 mg, 2.47 mmol) in diethyl ether (1.5 mL) was added a solution of p-toluenesulfonic acid hydrate (472 mg, 2.48 mmol) in ethanol (3 mL). The solution was mixed at 60–65° C. at ca. 500 mbar. The ether evaporated and the resulting ethanolic solution was mixed for 4 hr. The ethanol was evaporated in vacuo to yield 919 mg of compound C as a white solid (96% yield).

$^1$H NMR (d$_6$-DMSO) 400 MHz δ 8.51 (s, 2H), 7.78 (s, 1H), 7.46 (d, J=8 Hz, 2H), 7.09 (d, J=8 Hz, 2H), 4.39 (m, 1H), 4.04 (m, 4H), 3.90 (m, 2H), 2.26 (s, 3H), 0.90 (m, 2H), 0.00 (s, 7H) ppm.

D. 2-(Trimethylsilyl)ethyl1-(isopropylsulfonyl)azetidin-3-ylcarbamate.

To a solution of compound C (3.11 g, 8.00 mmol) in acetonitrile (50 mL) was added triethylamine (3.4 mL, 24.4 mmol). The mixture was stirred while cooling to 0° C. Isopropylsulfonyl chloride (1.0 mL, 8.91 mmol) was added and the solution was stirred while warming to RT. The reaction was allowed to proceed for 1 hr after which the acetonitrile was removed in vacuo and the resulting residue taken up with dichloromethane and washed with saturated aqueous NaHCO$_3$, then brine. The organic layer was dried over MgSO$_4$ and concentrated in vacuo. The resulting residue was chromatographed on silica gel (25% EtOAc/75% hexanes) to afford 1.89 g of compound D as an oil which solidified into a white solid (73% yield).

$^1$H NMR (d$_6$-DMSO) 400 MHz δ 7.76 (m, 1H), 4.26 (m, 1H), 4.02 (m, 2H), 3.89 (m, 2H), 3.79 (m, 2H), 3.19 (m, 1H), 1.19 (d, J=7 Hz, 6H), 0.89 (m, 2H), 0.00 (s, 7H) ppm.

E. 1-(Isopropylsulfonyl)azetidin-3-amine trifluoroacetate.

To a solution of compound D (412 mg, 1.28 mmol) in dichloromethane (25 mL) at 0° C. was added trifluoroacetic acid (0.75 mL, 9.74 mmol). The mixture was stirred at 0° C. for 3 hr and then allowed to warm to RT and stir for 16 hr. Additional trifluoroacetic acid (3.0 mL) was added and the mixture was stirred for an additional 3 hr. The dichloromethane and trifluoroacetic acid were removed in vacuo.

The residue was free-based with triethylamine (1.1 equiv.) and then chromatographed on silica gel (10% MeOH/90% CHCl₃) to afford 192 mg of compound E as a yellow oil (62% yield).

¹H NMR (d₆-DMSO) 400 MHz δ 4.07 (br. m, 1H), 3.80 (m, 2H), 3.57 (m, 3H), 3.16 (m, 1H), 2.26 (m(br) 2H), 1.18 (d, J=7 Hz, 6H) ppm.

F. (2S,4S)-4Fluoro-1-({[1-(isopropylsulfonyl)azetidin-3-yl]amino}acetyl)pyrrolidine-2-carbonitrile trifluoroacetate.

To a solution of compound E (200 mg, 1.12 mmol) and N,N-diisopropylethylamine (0.50 mL, 2.92 mmol) in acetonitrile (5 mL) at 50° C. is added (2S,4S)-1-(bromoacetyl)-4-fluoropyrrolidine-2-carbonitrile (described earlier) in acetonitrile (5 mL) dropwise over 7 minutes. The mixture is stirred for 1 hr after which the acetonitrile was removed in vacuo and the resulting residue taken up in ethyl acetate. After washing with saturated aqueous NaHCO₃, the organic layer was dried over MgSO₄ and concentrated in vacuo. The residue was chromatographed on silica gel (10% MeOH/90% EtOAc) and the resulting product taken up in dichloromethane and acidified with trifluoroacetic acid (1.1 eq). The solution was concentrated in vacuo to afford 39 mg of compound F an off-white solid (15% yield).

¹H NMR (d₆-DMSO) 400 MHz δ 9.70 (m, 1H), 8.28 (m, 1H), 5.53 (m, d, J=52 Hz, 1H), 5.04 (d, J=9 Hz, 1H), 4.21–3.59 (m, 10H), 3.23 (m, 1H), 1.20 (d, J=7 Hz, 6H) ppm.

Example 33

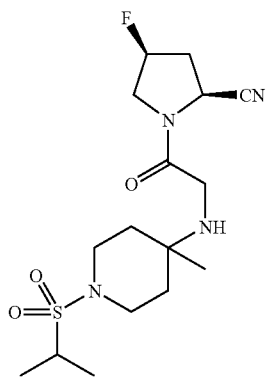

(2S,4S)-4-Fluoro-1-({[1-(isopropylsulfonyl)-4-methyl-4-piperidinyl]amino}acetyl)-2-pyrrolidinecarbonitrile hydrochloride A. 1-(Isopropylsulfonyl)-4-methyl-4-piperidinamine.

Isopropylsulfonyl chloride (713 mg, 5 mmol) was added to a stirred solution of 4-methyl-4-piperidinamine dihydrochloride (930 mg, 5 mmol) (prepared as described by Himmelbasch, Frank et al., WO 9732880) and potassium carbonate (2.07 g, 15 mmol) at 0° C. The mixture was stirred vigorously for 12 hours and then filtered. The solid was washed with 10 mL methylene chloride and the filtrate extracted with 50 mL of methylene chloride (3×). The organic phases were combined, dried (MgSO₄), and concentrated in vacuo to obtain 230 mg (yield: 21%) of compound A.

¹H NMR (CDCl₃) 400 MHz δ 3.40–3.30 (m, 4H), 3.15 (m, 1H), 1.65–1.55 (m, 2H), 1.48–1.40 (m, 2H), 1.31 (d, J=7.8 Hz, 6H), 1.14 (s, 3H) ppm.

B. (2S,4S)-4-fluoro-1-({[1-(Isopropylsulfonyl)-4-methyl-4-piperidinyl]amino}acetyl)-2-pyrrolidinecarbonitrile hydrochloride.

A solution of compound A (200 mg, 0.91 mmol), 1-N-bromoacetyl-2-(S)-cyano-4-(S)-fluoro-pyrrolidine (200 mg, 0.85 mmol) and N,N-diisopropylethylamine (200 mg, 1.55 mmol) stirred at 50° C. for 2 hours in 5 mL acetonitrile. The mixture was concentrated in vacuum, dissolved in 10 mL methylene chloride and filtered through a silica gel plug. Ether (10 mL) was added to the filtrate, then the solution was acidified with 2.0 M HCl (in ether). The white precipitate was filtered and washed with 2 mL of ether to obtain 165 mg (yield: 47%) compound B.

¹H NMR (DMSO-d₆) 400 MHz δ 9.10 (s (broad), 2H), 5.55 (d, J=51.7 Hz, 1H), 5.07 (d, J=8.4 Hz, 1H), 4.30–3.00 (m, 9H), 1.90–1.60 (m, 6H), 1.36 (s, 3H), 1.21 (d, J=6.9 Hz, 6H) ppm.

Comparative Examples

Compounds of the present invention were tested against non-fluorinated counterpart compounds to determine relative potency, duration, and selectivity. The results of such comparative testing illustrate several surprising and unexpected benefits. More specifically, the comparative tests indicate that the fluorinated compounds of the present invention demonstrate: (i) increased potency, as characterized by DPP-IV inhibition activity measured from plasma; (ii) increased selectivity; and/or (iii) increased duration.

When compounds of the present invention were tested in vivo at time periods ranging from 0 to 10 hours, the compounds of the present invention demonstrated a significant increase in DPP-IV inhibition over the non-fluorinated counterparts. Thus, the compounds of the present invention provide an unexpected potency that was not heretofore appreciated.

Biological Data

Materials:

H-Ala-Pro-pNA.HCl was purchased from BACHEM Bioscience Inc. (product no. L-1115). A 500 mM stock solution was prepared with dimethylsulfoxide and stored at −20° C. Gly-Pro-AMC was purchased from Enzyme System Products (product no. AMC-39) and stored at −20° C. as a 10 mM stock solution in dimethylsulfoxide. Test compounds were dissolved to 10 mM in dimethylsulfoxide and this was used as a stock solution for DPP-IV titration assays. Athens Research and Technology, Inc prepared the purified human DPP-IV. The material was isolated from human prostasomes using the method of DeMeester et al., *J. Immunol Methods* 189, 99–105. (1996).

DPP-IV Assay:

Two-fold serial dilutions of test compounds in 100% dimethylsulfoxide were performed in 96-well polystyrene flat bottom plates (Costar, #9017). The average enzymatic activity from wells containing dimethylsulfoxide but lacking test compound was used as a control value for calculating percent inhibition. DPP-IV (20 ng/mL) was mixed in microtiter plates with test compounds, substrate and assay buffer to yield 100 μM H-Ala-Pro-pNA.HCl in 25 mM Tris, pH 7.5, 10 mM KCl, 140 mM NaCl. The intact peptide contains a p-nitrophenylanilide which, when hydrolyzed by DPP-IV, releases the absorbant p-nitrophenylaniline. The absorbency was monitored in 20 minutes intervals at a wavelength of 387 nm using a Molecular Devices SpectraMax 250 absorbency plate reader. The enzymatic activity was determined by estimating the best linear fit to the data. Values for enzymatic activity were taken directly from the linear fit determined by the software on the plate reader.

Data Analysis: The enzymatic activity was determined by estimating the best linear fit to the data. Data reduction was performed using the Microsoft Excel RoboSage.

Determination of $IC_{50}$ values: The enzymatic activity was plotted against the concentration of test compound, including [1]=0, and the $IC_{50}$ determined from a fit of equation 2 to the data.

$$\text{RATE} = V_{max}/(1+([1]/IC_{50})) \qquad (2)$$

$V_{max}$ was the best fit estimate of the maximal enzymatic activity.

Determination of $K_i$ values: $K_i$ values were calculated from $IC_{50}$ values using equation 3 assuming a competitive model.

$$K_i = IC_{50} * \left[1 - \frac{S}{(S+K_m)}\right] \qquad (3)$$

The apparent pKi values were >5.0 for each of the examples.

DPP-II Assay:

The intermediate plate contained 5.3 µL of test compound in 2-fold serial dilutions across the plate. A volume of 209 µL of buffer (100 mM sodium acetate pH 5.5) containing substrate (H-Lys-Ala-pNA.2HCl; product no. L-2085; BACHEM Bioscience Inc.:) was added to each well of the intermediate plate, then mixed. The reaction was initiated with the transfer of 180 µL of the substrate/test compound solution to the assay plate containing 20 µL of enzyme. Final concentrations in the assay were 100 nM enzyme and 1000 µM substrate in 100 mM NaOAc, pH 5.5. 2.5% DMSO in a final volume of 200 µL The absorbance was monitored every 20 minutes for 5 hours at 387 nm using a Molecular Devices SpectraMax 250 absorbance plate reader.

Data Analysis: The enzymatic activity was determined by estimating the best linear fit to the data. Data reduction was performed using the Microsoft Excel RoboSage.

Determination of $IC_{50}$ values: The enzymatic activity was plotted against the concentration of test compound, including [1]=0, and the $IC_{50}$ determined from a fit of equation 2 to the data.

$$\text{RATE} = V_{max}/(1+([1]/IC_{50})) \qquad (2)$$

$V_{max}$ was the best fit estimate of the maximal enzymatic activity.

Determination of $K_i$ values: $K_i$ values were calculated from $IC_{50}$ values using equation 3 assuming a competitive model.

$$K_i = IC_{50} * \left[1 - \frac{S}{(S+K_m)}\right] \qquad (3)$$

Certain compounds of the present invention showed activity for DPP-II, for example pKi values >6.0, while others demonstrated selectivity for DPP-IV, discussed hereinabove.

In vivo Studies:

Age and weight matched male CD1 mice were housed individually at 72° F. and 50% relative humidity with a 12 h light/dark cycle. Animals were dosed by oral gavage with 10 ml/kg vehicle (0.5% methylcellulose (HPMC) with 0.1% Tween 80) or 1 mg/kg test compound in vehicle. The animals were anesthetized with isofluorane for blood collection at the specified times (0–6 hours). Plasma DPP-IV activity was measured using the fluorogenic substrate Gly-Pro-AMC (50 µM) according to the manufacturers specification (Enzyme System Products, Livermore Calif.). The substrate was mixed with 50 mM Tris, pH 7.8 and 20% plasma. The samples were incubated for 20 min at 30° C. and fluorescence measured using a cytofluor spectrofluorometer with the filters set at 360 nm excitation and 460 nm emission.

All research complied with the principles of laboratory animal care (NIH publication No. 85–23, revised 1985) and GlaxoSmithKline policy on animal use.

Although specific embodiments of the present invention have been illustrated and described in detail, the invention is not limited thereto. The above detailed description of preferred embodiments is provided for example only and should not be construed as constituting any limitation of the invention. Modifications will be obvious to those skilled in the art, and all modifications that do not depart from the spirit of the invention are intended to be included within the scope of the appended claims.

What is claimed is:

1. A compound of formula (I):

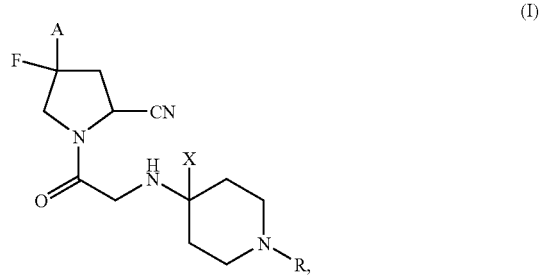

wherein A is H or F, X is H or alkyl and R is selected from isopropylsulfonyl, benzylsulfonyl, naphthylethylsulfonyl, mesitylsulfonyl, optionally substituted cycloalkylsulfonyl, benzoxazolyl, or optionally substituted aryl.

2. The compound of claim 1 wherein said aryl is substituted one or more times with cyano, halogen, nitro, or haloalkyl.

3. The compound of claim 1 wherein said aryl is phenyl or benzyl.

4. The compound of claim 1 wherein said cycloalkylsulfonyl is substituted one or more times with oxo or alkyl.

5. The compound of claim 1 wherein said cycloalkylsulfonyl is dimethyl-oxo-bicyclo[2.2.1]-heptyl methyl sulfonyl.

6. The compound of formula (II):

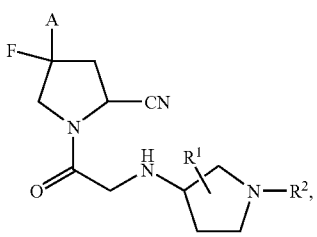

wherein A is H or F, R¹ is H or oxo, and R² is alkylsulfonyl, optionally substituted aryl, optionally substituted heteroaryl.

7. The compound of claim 6 wherein R¹ is oxo.

8. The compound of claim 6 wherein R² is optionally substituted phenyl.

9. The compound of claim 6 wherein said aryl is substituted one or more times with halogen.

10. The compound of claim 6 wherein R¹ is H.

11. The compound of claim 6 wherein said alkylsulfonyl is $C_1$–$C_6$ alkylsulfonyl.

12. The compound of claim 11 wherein said alkylsulfonyl is isopropylsulfonyl.

13. The compound of claim 6 wherein R² is optionally substituted pyridyl.

14. The compound of claim 6 wherein said heteroaryl is substituted one or more times with cyano.

15. A compound of formula (III):

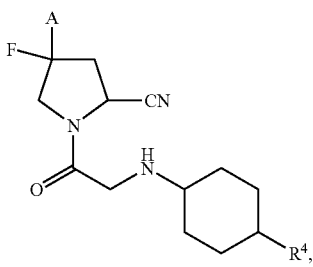

wherein A is H or F, R⁴ is selected from optionally substituted aryl or alkyl.

16. The compound of claim 15 wherein said alkyl is $C_1$–$C_6$ alkyl.

17. The compound of claim 16 wherein said alkyl is t-butyl.

18. The compound of claim 15 wherein said aryl is substituted one or more times with halogen or haloalkyl.

19. The compound of claim 15 wherein said aryl is phenyl.

20. A compound of formula (IV):

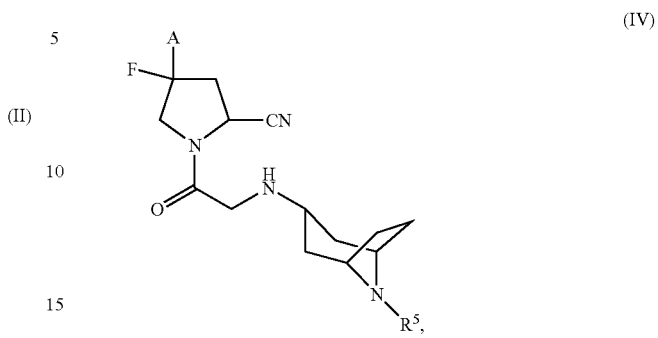

wherein A is H or F, R⁵ is alkoxycarbonyl.

21. The compound of claim 20 wherein R⁵ is $C_1$–$C_6$ alkoxycarbonyl.

22. The compound of claim 21 wherein R⁵ is ethyloxycarbonyl.

23. A compound of formula (V):

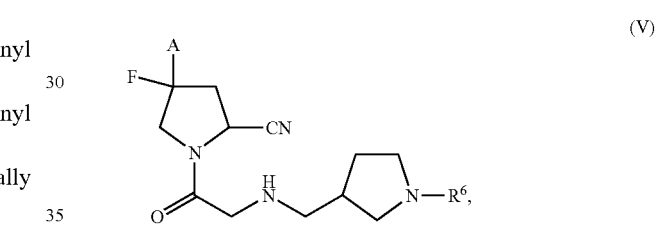

wherein A is H or F, R⁶ is alkylsulfonyl or optionally substituted aryl.

24. The compound of claim 23 wherein said alkylsulfonyl is $C_1$–$C_6$ alkylsulfonyl.

25. The compound of claim 23 wherein said alkylsulfonyl is isopropylsulfonyl.

26. The compound of claim 23 wherein said aryl is substituted one or more times with halogen or cyano.

27. The compound of claim 23 wherein said aryl is phenyl.

28. A compound of formula (VI):

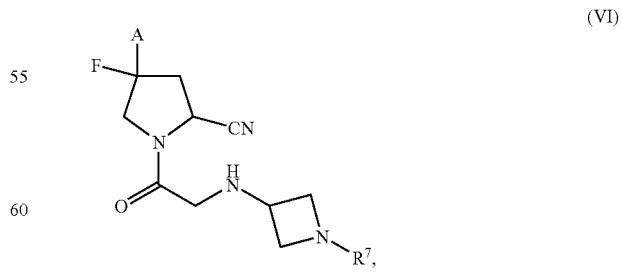

wherein A is H or F, R⁷ is alkyl sulfonyl.

29. The compound of claim 28 wherein R⁷ is $C_1$–$C_6$ alkylsulfonyl.

30. The compound of claim 29 wherein $R^7$ is isopropylsulfonyl.

31. A compound selected from:

(2S,4S)-4-Fluoro-1-({[1-(isopropylsulfonyl)-4-piperdinyl]amino}acetyl)-2-pyrrolidinecarbonitrile hydrochloride;

(2S)-4,4-Difluoro-1-({[1-(isopropylsulfonyl)-4-piperidinyl]amino}acetyl)-2-pyrrolidinecarbonitrile;

(2S,4S)-4-Fluoro-1-({[(3S)-1-(4-fluorophenyl)-2-oxopyrrolidinyl]amino}acetyl)-2-pyrrolidinecarbonitrile hydrochloride;

(2S,4S)-4-Fluoro-1-({[(3S)-1-(4-fluorobenzyl)-2-oxopyrrolidinyl]amino}acetyl)-2-pyrrolidinecarbonitrile hydrochloride;

(2S,4S)-1-{[(1-Benzylpiperidin-4-yl)amino]acetyl}-4-fluoropyrrolidine-2-carbonitrile hydrochloride;

(2S,4S)-4-Fluoro-1-({[1-(4-fluorophenyl)piperidin-4-yl]amino}acetyl)pyrrolidine-2-carbonitrile hydrochloride;

(2S,4S)-1-({[1-(4-Cyanophenyl)piperidin-4-yl]amino}acetyl)-4-fluoropyrrolidine-2-carbonitrile hydrochloride;

(2S,4S)-1-({[1-(4-Cyano-3-fluorophenyl)piperidin-4-yl]amino}acetyl)-4-fluoropyrrolidine-2-carbonitrile hydrochloride;

(2S,4S)-1-({[1-(4-Cyano-3,5-difluorophenyl)piperidin-4-yl]amino}acetyl)-4-fluoropyrrolidine-2-carbonitrile hydrochloride;

(2S,4S)-1-({[1-(3-Cyano-5-fluorophenyl)piperidin-4-yl]amino}acetyl)-4-fluoropyrrolidine-2-carbonitrile hydrochloride;

(2S,4S)-1-({[1-(3,5-Difluorophenyl)piperidin-4-yl]amino}acetyl)-4-fluoropyrrolidine-2-carbonitrile hydrochloride;

(2S,4S)-4-Fluoro-1-{[(4-phenylcyclohexyl)amino]acetyl}pyrrolidine-2-carbonitrile hydrochloride;

Ethyl 3-({2-[(2S,4S)-2-cyano-4-fluoropyrrolidin-1-yl]-2-oxoethyl}amino)-8-azabicyclo[3.2.1]octane-8-carboxylate hydrochloride;

(2S,4S)-4-Fluoro-1-({[4-(4-fluorophenyl)cyclohexyl]amino}acetyl)pyrrolidine-2-carbonitrile hydrochloride;

(2S,4S)-4-Fluoro-1-[({4-[4-(trifluoromethyl)phenyl]cyclohexyl}amino)acetyl]pyrrolidine-2-carbonitrile hydrochloride;

(2S,4S)-4-Fluoro-1-{[(4-pyridin-2-ylcyclohexyl)amino]acetyl}pyrrolidine-2-carbonitrile hydrochloride (cis & trans);

(2S,4S)-1-{[(4-Tert-butylcyclohexyl)amino]acetyl}-4-fluoropyrrolidine-2-carbonitrile hydrochloride;

(2S,4S)-4-Fluoro-1-[({[(3R)-1-(isopropylsulfonyl)pyrrolidinyl]methyl}amino)acetyl]-2-pyrrolidinecarbonitrile and hydrochloride;

(2S,4S)-4-Fluoro-1-[({[(3S)-1-(isopropylsulfonyl)pyrrolidinyl]methyl}amino)acetyl]-2-pyrrolidinecarbonitrile and hydrochloride;

(2S,4S)-1-[({[(3R)-1-(3-Cyano-5-fluorophenyl)pyrrolidinyl]methyl}amino)acetyl]-4-fluoro-2-pyrrolidinecarbonitrile hydrochloride;

(2S,4S)-4-Fluoro-1-({[1-(4-nitrophenyl)piperidin-4-yl]amino}acetyl) pyrrolidine-2-carbonitrile;

(2S,4S)-4-Fluoro-1-[({1-[4-(trifluoromethyl)phenyl]piperidin-4-yl}amino)acetyl]pyrrolidine-2-carbonitrile hydrochloride;

(2S,4S)-1-({[1-(1,3-Benzoxazol-2-yl)piperidin-4-yl]amino}acetyl)-4-fluoropyrrolidine-2-carbonitrile hydrochloride;

(2S,4S)-1-({[1-({[(1R,4R)-7,7-dimethyl-2-oxobicyclo[2.2.1]hept-1-yl]methyl}sulfonyl)piperidin-4-yl]amino}acetyl)-4-fluoropyrrolidine-2-carbonitrile hydrochloride;

(2S,4S)-1-({[1-(Benzylsulfonyl)piperidin-4-yl]amino}acetyl)-4-fluoropyrrolidine-2-carbonitrile hydrochloride;

(2S,4S)-4-Fluoro-1-{[(1-{[2-(1-naphthyl)ethyl]sulfonyl}piperidin-4-yl)amino]acetyl}pyrrolidine-2-carbonitrile hydrochloride;

(2S,4S)-4-Fluoro-1-({[1-(mesitylsulfonyl)piperidin-4-yl]amino}acetyl)pyrrolidine-2-carbonitrile hydrochloride;

(2S,4S)-4-Fluoro-1-({[(3R)-1-(isopropylsulfonyl)pyrrolidinyl]amino}acetyl)-2-pyrrolidine hydrochloride;

(2S,4S)-4-Fluoro-1-({[(3S)-1-(isopropylsulfonyl)pyrrolidinyl]amino}acetyl)-2-pyrrolidine hydrochloride;

6-[(3S)-3-({2-[(2S,4S)-2-Cyano-4-fluoropyrrolidin-1-yl]-2-oxoethyl}amino)pyrrolidin-1-yl]nicotinonitrile bis(trifluoroacetate); and (2S,4S)-4-Fluoro-1-({[1-(isopropylsulfonyl)azetidin-3-yl]amino}acetyl)pyrrolidine-2-carbonitrile trifluoroacetate.

32. The compound of claim 1 wherein X is H.

33. The compound of claim 1 wherein X is $C_1$–$C_6$ alkyl.

34. The compound of claim 1 wherein X is methyl.

35. A pharmaceutical formulation comprising a compound a claim 31.

36. The pharmaceutical formulation of claim 35 further comprising a pharmaceutically acceptable carrier.

37. A method for the treatment of diabetes, HIV infection, allergies, arthritis, and transplant rejection, comprising administering an effective amount of a compound of claim 31.

38. The method of claim 37 wherein a therapeutically effective amount of a compound of claim 31 is administered for the treatment of diabetes.

* * * * *

UNITED STATES PATENT AND TRADEMARK OFFICE
CERTIFICATE OF CORRECTION

PATENT NO. : 7,183,290 B2
APPLICATION NO. : 10/481543
DATED : February 27, 2007
INVENTOR(S) : Haffner et al.

It is certified that error appears in the above-identified patent and that said Letters Patent is hereby corrected as shown below:

Claim 31 (Column 72, Lines 28-31) should read as follows:

(2S,4S)-4-Fluoro-1-({[(3R)-1-(isopropylsulfonyl)pyrro-
lidinyl]amino}acetl)-2-pyrrolidinecarbonitrile hydrochloride;
(2S,4S)-4-Fluoro-1-({[(3S)-1-(isopropylsulfonyl)pyrro-
lidinyl]amino}acetyl)-2-pyrrolidinecarbonitrile hydrochloride;

Claim 37 (Column 72, Lines 45-48) should read as follows:

37. A method for the treatment of diabetes, HIV infection,
arthritis, and transplant rejection, comprising administering
an effective amount of a compound of claim 31.

Signed and Sealed this

Twelfth Day of June, 2007

JON W. DUDAS
*Director of the United States Patent and Trademark Office*